(12) United States Patent
Goto et al.

(10) Patent No.: US 9,293,713 B2
(45) Date of Patent: Mar. 22, 2016

(54) ARYLAMINE COMPOUND

(71) Applicants: Daisuke Goto, Fukuoka (JP); Takuji Katoh, Kanagawa (JP); Satoshi Yamamoto, Kanagawa (JP); Masataka Mohri, Kanagawa (JP); Satoshi Miyagawa, Kanagawa (JP); Hajime Nakanotani, Kanagawa (JP)

(72) Inventors: Daisuke Goto, Fukuoka (JP); Takuji Katoh, Kanagawa (JP); Satoshi Yamamoto, Kanagawa (JP); Masataka Mohri, Kanagawa (JP); Satoshi Miyagawa, Kanagawa (JP); Hajime Nakanotani, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

(21) Appl. No.: 13/779,880

(22) Filed: Feb. 28, 2013

(65) Prior Publication Data

US 2013/0225858 A1 Aug. 29, 2013

(30) Foreign Application Priority Data

Feb. 28, 2012 (JP) ................................. 2012-041114

(51) Int. Cl.
| | | |
|---|---|---|
| C07C 69/76 | (2006.01) | |
| H01L 51/00 | (2006.01) | |
| C07C 219/32 | (2006.01) | |
| C09B 57/00 | (2006.01) | |
| H01L 51/50 | (2006.01) | |

(52) U.S. Cl.
CPC ............ *H01L 51/006* (2013.01); *C07C 219/32* (2013.01); *C09B 57/008* (2013.01); *H01L 51/0059* (2013.01); *C07C 2101/16* (2013.01); *C07C 2102/10* (2013.01); *C07C 2103/18* (2013.01); *H01L 51/5056* (2013.01)

(58) Field of Classification Search
CPC ...................................................... C07C 69/76
USPC ........................................................ 560/106
See application file for complete search history.

(56) References Cited

U.S. PATENT DOCUMENTS

| | | | |
|---|---|---|---|
| 4,579,800 A * | 4/1986 | Hirose et al. ............... | 430/58.25 |
| 7,166,689 B2 | 1/2007 | Sagisaka et al. | |
| 7,816,674 B2 | 10/2010 | Kato et al. | |
| 2007/0092760 A1 | 4/2007 | Sagisaka et al. | |
| 2009/0206329 A1 | 8/2009 | Yamaga et al. | |
| 2009/0230386 A1 | 9/2009 | Yamamoto et al. | |
| 2010/0279460 A1 | 11/2010 | Yamaga et al. | |
| 2012/0119195 A1 | 5/2012 | Sagisaka et al. | |
| 2012/0153271 A1 | 6/2012 | Goto et al. | |
| 2013/0095605 A1 | 4/2013 | Goto et al. | |

FOREIGN PATENT DOCUMENTS

| | | |
|---|---|---|
| WO | WO 2009/035133 | 3/2009 |
| WO | WO 2009/128559 | 10/2009 |

* cited by examiner

*Primary Examiner* — Scarlett Goon
*Assistant Examiner* — Sonya Wright
(74) *Attorney, Agent, or Firm* — Oblon, McClelland, Maier & Neustadt, L.L.P.

(57) ABSTRACT

An arylamine compound including: a partial structure shown in formula (1-1) or (1-2), wherein either X or Y is one of leaving substituents and the other is a hydrogen atom; either $(X_1, X_2)$ or $(Y_1, Y_2)$ is one of the leaving substituents respectively and the other is the hydrogen atom respectively; each of $Q_1$, $Q_2$, $Q_3$, $Q_4$, $Q_5$, and $Q_6$ is selected from the hydrogen atom, a halogen atom, organic substituents other than the leaving substituents, and an atomic bonding to link with an adjacent arylamine group respectively; and adjacent two substituents selected from $Q_1$, $Q_2$, $Q_3$, $Q_4$, $Q_5$, and $Q_6$ may be linked together to form the ring which may be a part of an arylamine group.

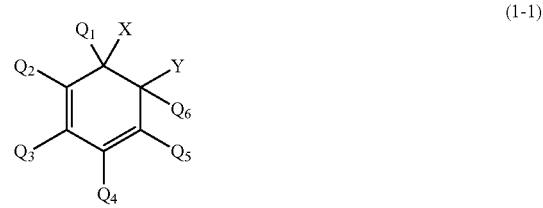

(1-1)

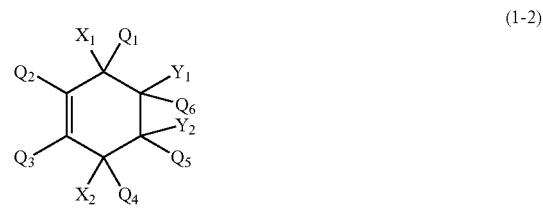

(1-2)

20 Claims, 1 Drawing Sheet

ARYLAMINE COMPOUND

CROSS-REFERENCE TO RELATED APPLICATIONS

This patent application claims priority pursuant to 35 U.S.C. §119 to Japanese Patent Application No. 2012-041114, filed on Feb. 28, 2012, the entire disclosure of which is hereby incorporated by reference herein.

FIELD OF THE INVENTION

An object of the invention pertains to an arylamine compound, an ink, and a method for producing an arylamine compound.

BACKGROUND OF THE INVENTION

Organic EL elements can be divided into two groups of elements on the basis of process for making or property of material. The first elements are made of a material having low molecular weight using a deposition process, and the second elements are made of a material having high molecular weight using a coating process.

The first elements have disadvantages such as expensive production cost, and difficulty to apply for a large substrate or mass production, because it requires a vacuum deposition equipment. Meanwhile, the second elements have advantages such as cheap production cost, and simple manufacturing process, because it is easy to make film, composed of coating liquid, on a substrate, and removing solvent, which is included in the coating liquid.

When the thin film for an organic EL material is made by the coating method, the organic EL material is used to be dissolved into solvent. In this case, generally, the organic EL material having high molecular weight is dissolved into solvent. The solvent includes toluene, xylene, Tetralin®, mesitylene, and cyclohexylbenzene.

Meanwhile, when the organic EL material having low molecular weight is made by the coating method, wherein the organic EL material having low molecular weight is used to be dissolved into solvent, solubility of the organic EL material is important. The organic EL material having low molecular weight should have high solubility such as, for example 0.5 to 1.0% by mass, however most of the organic EL material having low molecular weight of prior art does not have high solubility.

For improving solubility, the method to introduce a soluble substituent, and method to decrease a symmetry of molecule are known (See also Japanese Patent Application Laid-Open (JP-A) No. 2008-166629). However when the soluble substituent is introduced, it is difficult to keep high thermal stability and temporal stability, because of its phase transition due to the soluble substituent such as alkyl groups. When the symmetry of the molecule is decreased, molecular design to ensure appropriate property is limited, because it requires asymmetric structure, bent structure, or bulky structure as a whole.

It is difficult to satisfy both of solubility and flexibility for molecular design.

Meanwhile, it is known that multiple films, wherein each of films has different function, are laminated in the organic EL element to increase its property. The deposition process is relatively suitable for laminating multiple films, because it is the vacuum process. The coating process is not suitable for laminating multiple films, because solvent of the upper film dissolves the lower film in laminating. When organic solvent and water solvent are used in wet coating process, two films can be laminated, but it is difficult to laminate more than three films.

To solve the problem in laminating, U.S. Pat. No. 4,761,006, JP-A No. 2004-505169, international publication No. 2008/038747, and international publication No. 2005/053056, propose high molecular compound having crosslinkable substituent, and also disclose method for laminating, wherein the compound becomes insoluble to organic solvent by its crosslink reaction. However, using this method smooth film is not obtained, or durability of element decreases, by a change of its volume associated with the crosslink reaction.

The method to satisfy all of solubility, flexibility for molecular design, and capability of laminating has not proposed.

BRIEF SUMMARY OF THE INVENTION

The present invention provides an arylamine compound comprising leaving substituent, wherein the arylamin compound has high solubility, and the leaving substituent is eliminated by outer stimulation with changing its solubility.

An arylamine compound of the present invention comprises a partial structure shown in formula (1-1) or (1-2), wherein either X or Y is one of leaving substituents and the other is a hydrogen atom; either ($X_1$, $X_2$) or ($Y_1$, $Y_2$) is one of the leaving substituents respectively and the other is the hydrogen atom respectively; each of $Q_1$, $Q_2$, $Q_3$, $Q_4$, $Q_5$, and $Q_6$ is selected from the hydrogen atom, a halogen atom, organic substituents other than the leaving substituents, and an atomic bonding to link with a carbon atom or a nitrogen atom of an adjacent aryl ring respectively; adjacent two substituents selected from $Q_1$, $Q_2$, $Q_3$, $Q_4$, $Q_5$, and $Q_6$ may be linked together to form a ring.

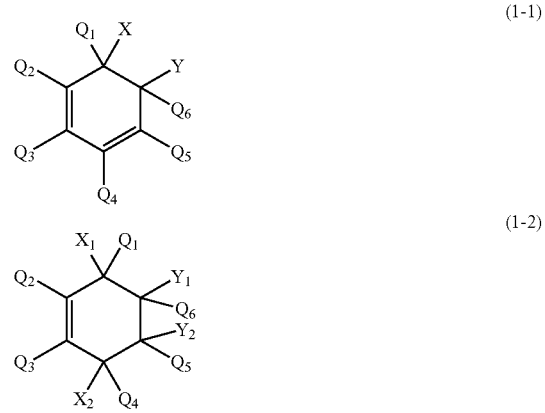

DETAILED DESCRIPTION OF THE INVENTION

Figure 1A:
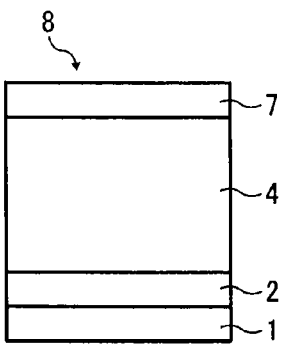
FIGS. 1A to 1E are schematic structural diagrams showing structural examples of an organic EL element.

Next, the present invention will be described referring to specific embodiments, which should not be construed as limiting the present invention thereto. The present invention can be variously made without departing the spirit and scope of the present invention.

In one embodiment of the present invention, an arylamine compound comprises a partial structure shown in formula (1-1) or (1-2), wherein either X or Y is one of leaving substituents and the other is a hydrogen atom; either ($X_1$, $X_2$) or ($Y_1$, $Y_2$) is one of the leaving substituents respectively and the other is the hydrogen atom respectively; each of $Q_1$, $Q_2$, $Q_3$, $Q_4$, $Q_5$, and $Q_6$ is selected from the hydrogen atom, a halogen atom, organic substituents other than the leaving substituents, and an atomic bonding to link with a an adjacent arylamine group respectively; and adjacent two substituents selected from $Q_1$, $Q_2$, $Q_3$, $Q_4$, $Q_5$, and $Q_6$ may be linked together to form the ring which may be a part of an arylamine group.

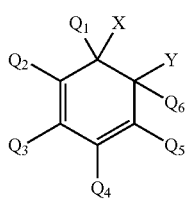

(1-1)

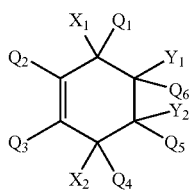

(1-2)

The leaving substituents preferably comprise at least one of ether groups and acyloxy groups.

The arylamine compound is preferably a triarylamine compound.

The partial structure shown in formula (1-1) or (1-2) is preferably selected from aromatic substituents having the atomic bonding to link with the carbon atom or the nitrogen atom of the adjacent aryl ring shown in formula (1-11), (1-12), (1-13), (1-14), (1-15), (1-16), (1-21), (1-22), (1-23), (1-24), and (1-25).

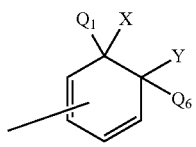

(1-11)

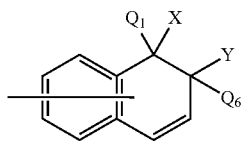

(1-12)

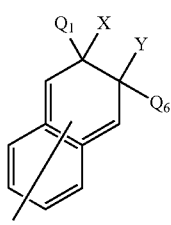

(1-13)

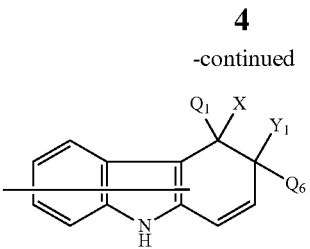

(1-14)

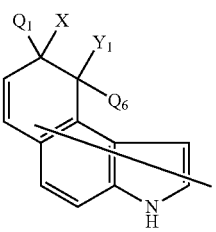

(1-15)

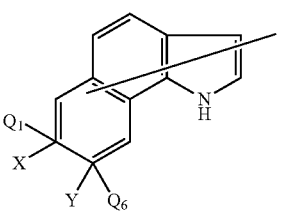

(1-16)

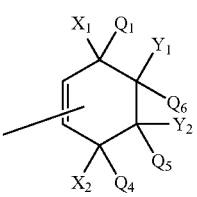

(1-21)

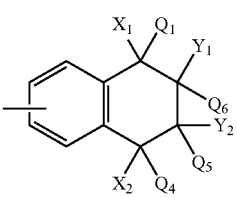

(1-22)

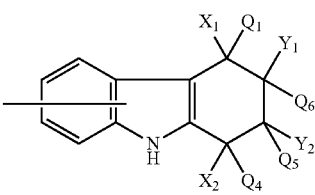

(1-23)

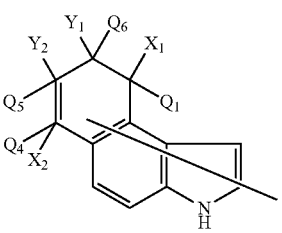

(1-24)

-continued

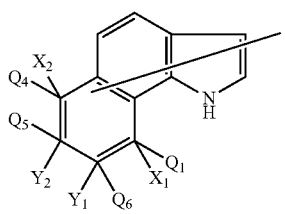
(1-25)

One or two substituents selected from ether groups and acyloxy groups preferably link with a cyclohexenyl group or a cyclohexadienyl group.

One or two pairs of $Q_1$ and $Q_6$, $Q_2$ and $Q_3$, $Q_3$ and $Q_4$, and $Q_4$ and $Q_5$ preferably link together to form multi condensed aryl ring.

The arylamine compound is preferably an organic electroluminescence material.

In one embodiment of the present invention, an ink comprises the arylamine compound.

In one embodiment of the present invention, a method for producing arylamine compound comprises applying external stimulus to a film formed of the arylamine compound, and eliminating the leaving substituent to form double bonding.

In one embodiment of the present invention, the method for producing the arylamine compound comprising applying external stimulus to a film formed of the arylamine compound, and eliminating the leaving substituent to form double bonding.

(Arylamine Compound)

In one embodiment, the arylamine compound has a partial structure shown in formula (1-1) or (1-2).

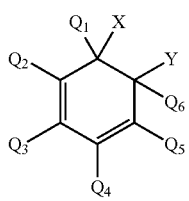
(1-1)

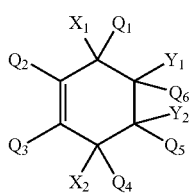
(1-2)

In formula (1-1) and (1-2), each of X, Y, $X_1$, $X_2$, $Y_1$, and $Y_2$ represents a hydrogen atom or a leaving substituent, wherein either $(X_1, X_2)$ or $(Y_1, Y_2)$ is one of the leaving substituents respectively and the other is the hydrogen atom respectively; each of $Q_1$, $Q_2$, $Q_3$, $Q_4$, $Q_5$, and $Q_6$ is selected from the hydrogen atom, a halogen atom, organic substituents other than the leaving substituents, and an atomic bonding to link with an adjacent arylamine group respectively; adjacent two substituents selected from $Q_1$, $Q_2$, $Q_3$, $Q_4$, $Q_5$, and $Q_6$ may be linked together to form the ring. which may be a part of an arylamine group; and $Q_1$, $Q_2$, $Q_3$, $Q_4$, $Q_5$, and $Q_6$ respectively may combine with the nitrogen atom directly or through the intermediary of other atom or ring.

In one embodiment, the arylamine group may be the group which comprises at least two aryl rings and at least one nitrogen atom that links with the aryl rings.

The partial structure shown in formula (1-1) or (1-2) may be an aromatic group selected from cyclohexenyl group shown in formula (1-21), cyclohexadienyl group shown in formula (1-11), benzocyclohexenyl group shown in formula (1-22), benzocyclohexadienyl group shown in formula (1-12) or (1-13), indolino[2,3]cyclohexenyl group shown in (1-23), (1-24), or (1-25), and indolino[2,3]cyclohexadienyl group shown in (1-14), (1-24), and (1-25).

One or two groups linked to the cyclohexenyl ring or the cyclohexadienyl ring may be replaced by an ether group or acyloxy group. Among $Q_1$ to $Q_6$, one or two pair, which is selected from a pair of $Q_1$ and $Q_6$, $Q_2$ and $Q_3$, $Q_3$ and $Q_4$, and $Q_4$ and $Q_5$, may combine together to form multi condensed aryl ring.

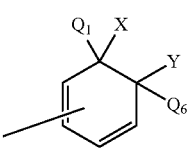
(1-11)

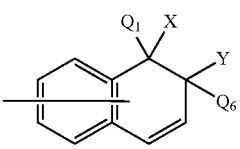
(1-12)

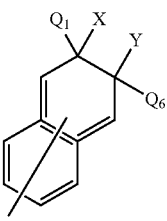
(1-13)

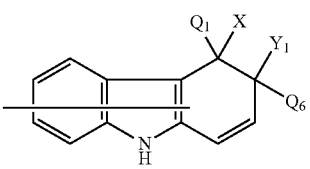
(1-14)

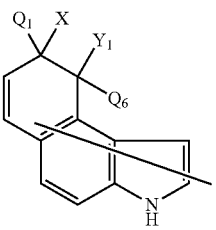
(1-15)

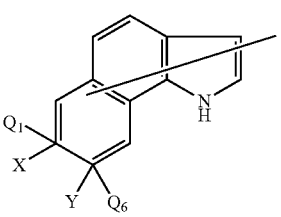
(1-16)

-continued

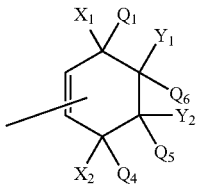
(1-21)

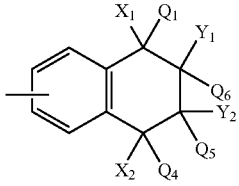
(1-22)

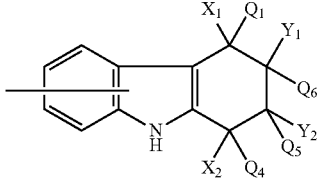
(1-23)

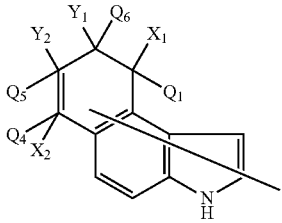
(1-24)

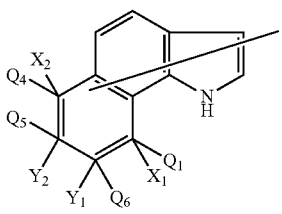
(1-25)

(Substituent Comprising Leaving Substituent)

Next, a substituent having a partial structure shown in formula (1-1) or (1-2) will be explained.

The substituent has a cyclohexenyl skeleton or a cyclohexadienyl skeleton; and a leaving substituent. The cyclohexenyl skeleton or the cyclohexadienyl skeleton; and the leaving substituent may be called as a soluble substituent.

The structure, which comprises the cyclohexenyl skeleton or the cyclohexadienyl skeleton; and the leaving substituent, has low crystallinity, because the soluble substituent is not stiff but bulky. Therefore, a molecule having the structure has excellent solubility. In addition, when a solution which the compound having the leaving substituent is dissolved is used for coating, a film having low crystallinity or an amorphous film may be obtained In Formulas (1-1) and (1-2), X, Y, $X_1$, $X_2$, $Y_1$, and $Y_2$ each represents a hydrogen atom or a leaving substituent, wherein one of X and Y is a leaving substituent and the other is a hydrogen atom; and one of ($X_1$, $X_2$) and ($Y_1$, $Y_2$) is the leaving substituent respectively and the other is the hydrogen atom respectively; $Q_2$ to $Q_5$ each represents the hydrogen atom, the halogen atom, the organic group other than the leaving substituent, or the atomic bonding to combine with the carbon atom or the nitrogen atom of the adjacent aryl ring; $Q_1$ and $Q_6$ each represents the hydrogen atom, the organic group other than the leaving substituent, or the atomic bonding to combine with the carbon atom or the nitrogen atom of the adjacent aryl ring; and $Q_1$ and $Q_6$ may combine with an adjacent group to form a ring.

The group represented by X, Y, $X_1$, $X_2$, $Y_1$, or $Y_2$ is the hydrogen atom or the leaving substituent. Examples of the leaving substituent include a halogen atom, a hydroxyl group, a substituted or unsubstituted ether group, a substituted or unsubstituted acyloxy group, a substituted or unsubstituted sulfonyloxy group, a nitroxy group, a substituted or unsubstituted phosphooxy group, a substituted or unsubstituted alkylamineoxide group, and groups that leaves with eliminating the hydrogen atom present on the β carbon such as substituted or unsubstituted polyalkyl quaternary ammonium salts. From the viewpoints of, for example, storage stability of the compound itself, dissolvability to an organic solvent, and conditions for elimination reaction of the substituent such as presence or absence of a catalyst, reaction temperature, etc., preferred are a substituted or unsubstituted ether group, a substituted or unsubstituted acyloxy group and a substituted or unsubstituted sulfonyloxy group. Particularly preferred are a substituted or unsubstituted ether group and a substituted or unsubstituted acyloxy group.

As described above, at least one of each X and Y; $X_1$ and $X_2$; and $Y_1$ and $Y_2$ is the leaving substituent (i.e., the substituted or unsubstituted ether group or acyloxy group having 1 or more carbon atoms) and the other is the hydrogen atom.

Examples of the substituted or unsubstituted ether group having 1 or more carbon atoms include ether groups derived from alcohols such as substituted or unsubstituted linear or cyclic aliphatic alcohols having 1 or more carbon atoms, and aromatic alcohols having 4 or more carbon atoms. Further examples include ether groups derived from organosiloxane. Further examples include thioether groups obtained by replacing the oxygen atom in the above ethers with a sulfur atom. The number of carbon atoms contained in the above ether group is generally 1 to 38, preferably 2 to 22, more preferably 3 to 18, considering various factors such as solubility and the boiling point of an eliminated component.

Specific examples of the ether group include a methoxy group, an ethoxy group, a propoxy group, a butoxy group, an isobutoxy group, a pivaloyl group, a pentoxy group, a hexyloxy group, a lauryloxy group, a trifluoromethoxy group, a 3,3,3-trifluoropropoxy group, a pentafluoropropoxy group, a cyclopropoxy group, a cyclobutoxy group, a cyclohexyloxy group, a trimethylsilyloxy group, a triethylsilyloxy group, a tert-butyldimethylsilyloxy group and a tert-butyldiphenylsilyloxy group. Further examples include thioethers obtained by replacing the oxygen atom in the ether bonds of the above ether group with a sulfur atom.

Examples of the substituted or unsubstituted acyloxy group having 1 or more carbon atoms include a formyloxy group; and an acyloxy group derived from carboxylic acids or carbonate half esters such as linear or cyclic aliphatic carboxylic acids or half esters thereof having two or more carbon atoms and optionally containing a halogen atom, and aromatic carboxylic acids having 4 or more carbon atoms.

Further examples include thiocarboxylic acids which the oxygen atom in the above carboxylic acids are replaced by the sulfur atom. The number of carbon atoms contained in the above acyloxy group is generally 1 to 38, preferably 2 to 22, more preferably 3 to 18, considering various factors such as solubility and the boiling point of the eliminated component.

Specific examples of the acyloxy group include a formyloxy group, an acetoxy group, a propionyloxy group, a butylyloxy group, an isobutylyloxy group, a pivaloyloxy group, a pentanoyloxy group, a hexanoyloxy group, a lauroyloxy group, a stearoyloxy group, a trifluoroacetyloxy group, 3,3,3-trifluoropropionyloxy group, a pentafluoropropionyloxy group, a cyclopropanoyloxy group, a cyclobutanoyloxy group, a cyclohexanoyloxy group, a benzoyloxy group, p-methoxyphenylcarbonyloxy group and a pentafluorobenzoyloxy group.

Additionally, there are exemplified carbonate esters derived from carbonate half esters in which an oxygen atom or sulfur atom is introduced, in the above acyloxy groups, between their carbonyl groups and their alkyl or aryl groups. Moreover, further examples include acylthioxy groups and thioacyloxy groups which the one or more oxygen atoms in the ether bonds and carbonyl moieties is or are replaced with a sulfur atom.

Next will be given some preferred examples of the leaving substituents X, Y, $X_1$, $X_2$, $Y_1$, or $Y_2$ described above.

TABLE 1

| Structure | No. |
|---|---|
| (No. 1) acetate | No. 1 |
| (No. 2) propanoate | No. 2 |
| (No. 3) isobutyrate | No. 3 |
| (No. 4) pivalate | No. 4 |
| (No. 5) $C_4H_9$ carbonate | No. 5 |
| (No. 6) 3-methylpentanoate | No. 6 |
| (No. 7) 4-methylpentanoate | No. 7 |
| (No. 8) hexanoate | No. 8 |
| (No. 9) heptanoate | No. 9 |

TABLE 1-continued

| Structure | No. |
|---|---|
| 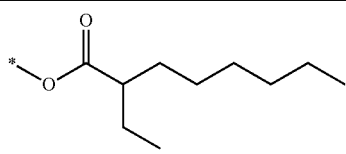 | No. 10 |
| 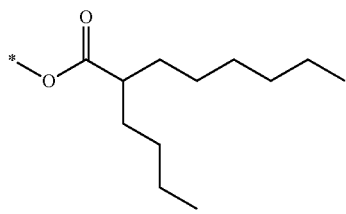 | No. 11 |
| 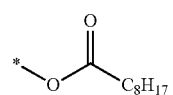 $C_8H_{17}$ | No. 12 |
| 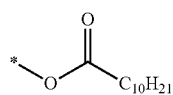 $C_{10}H_{21}$ | No. 13 |
| 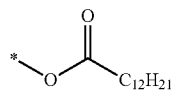 $C_{12}H_{21}$ | No. 14 |
| 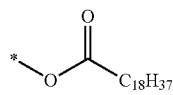 $C_{18}H_{37}$ | No. 15 |
| 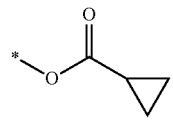 | No. 16 |
| 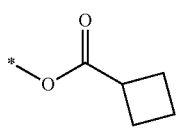 | No. 17 |
| 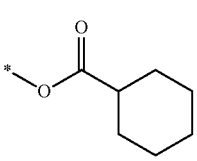 | No. 18 |
| 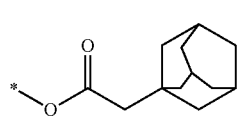 | No. 19 |
| 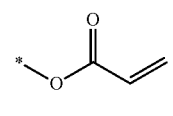 | No. 20 |
| 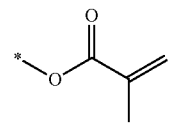 | No. 21 |

TABLE 1-continued
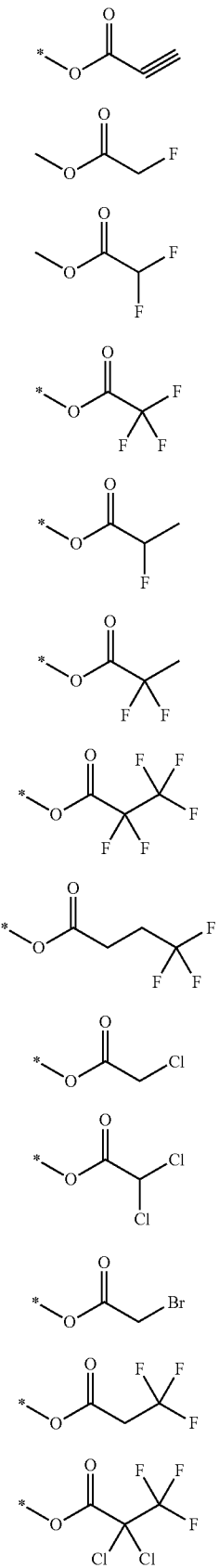
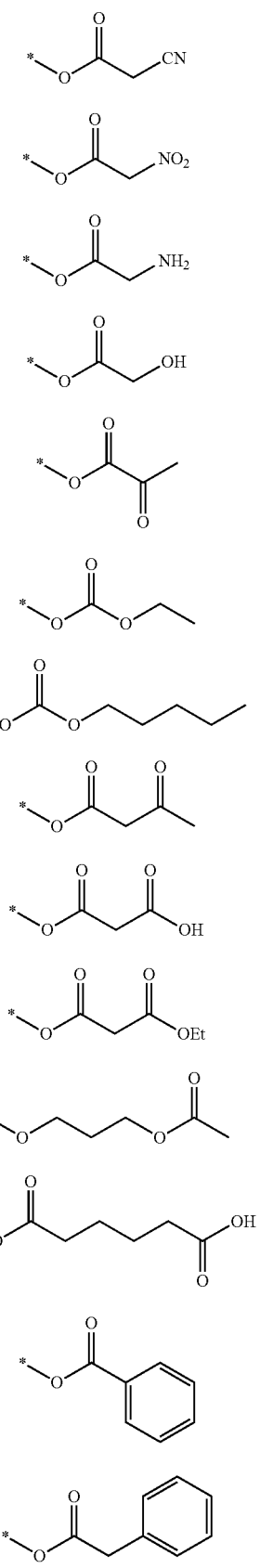

TABLE 1-continued
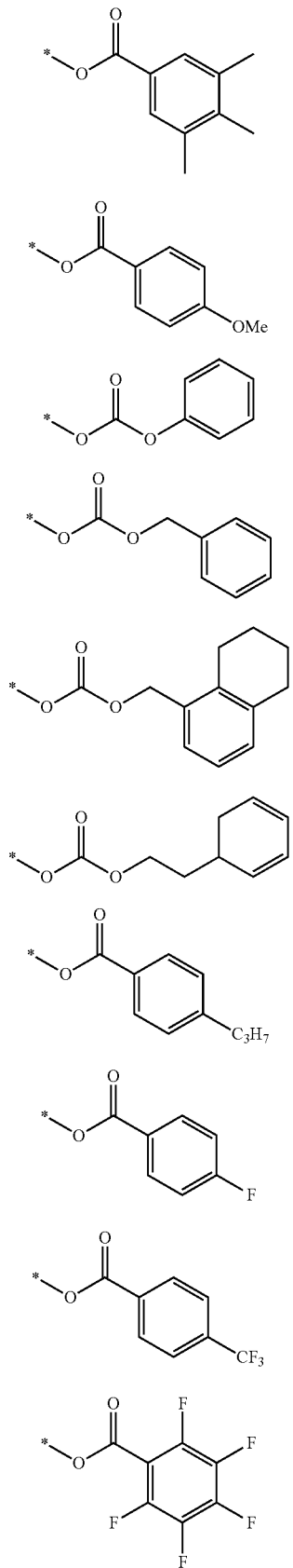
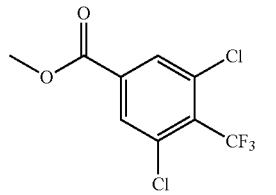 [SMILES: COC(=O)c1cc(Cl)c(C(F)(F)F)c(Cl)c1]
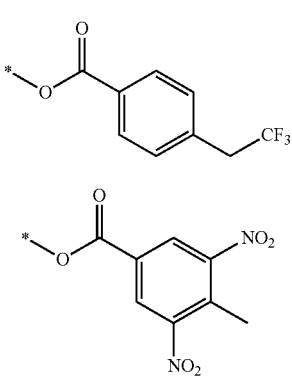

TABLE 1-continued
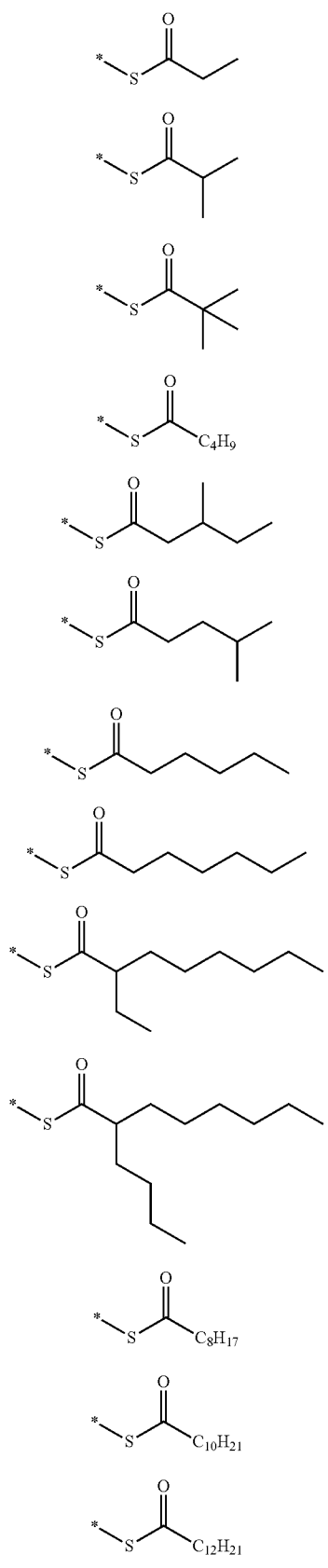
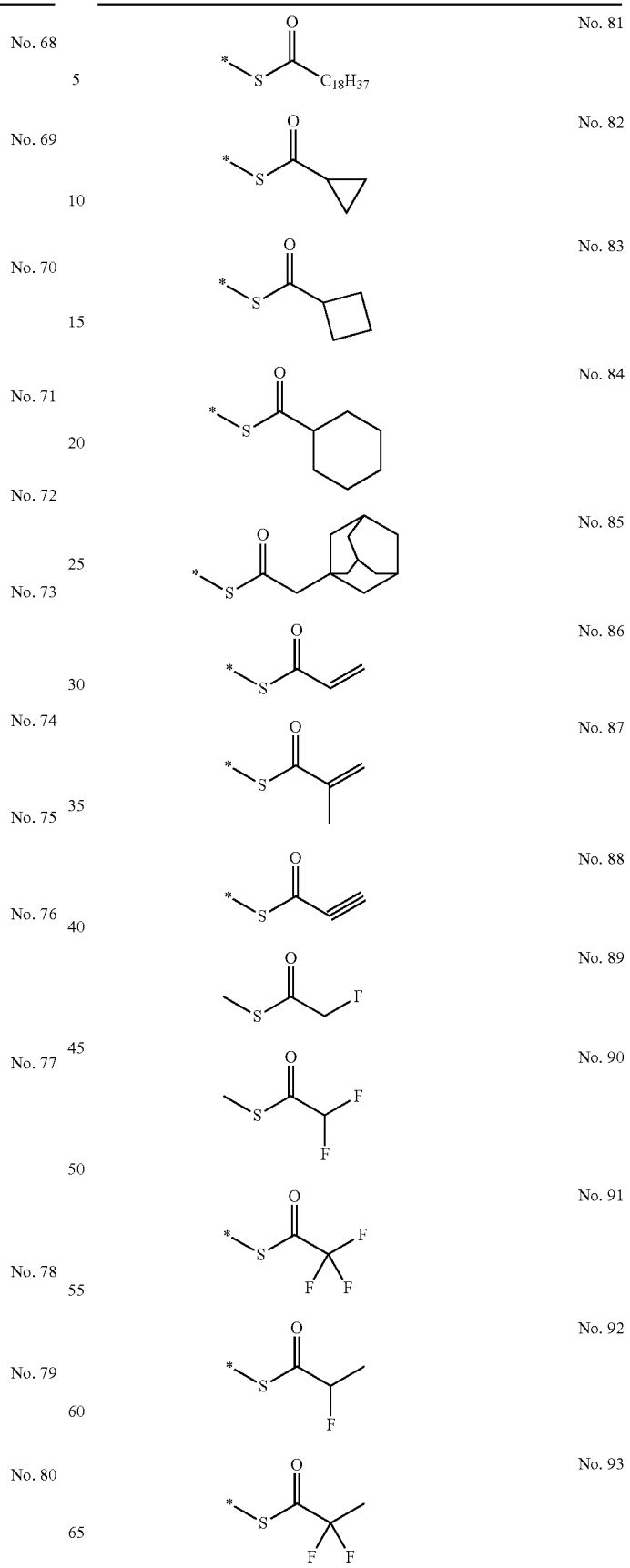

TABLE 1-continued
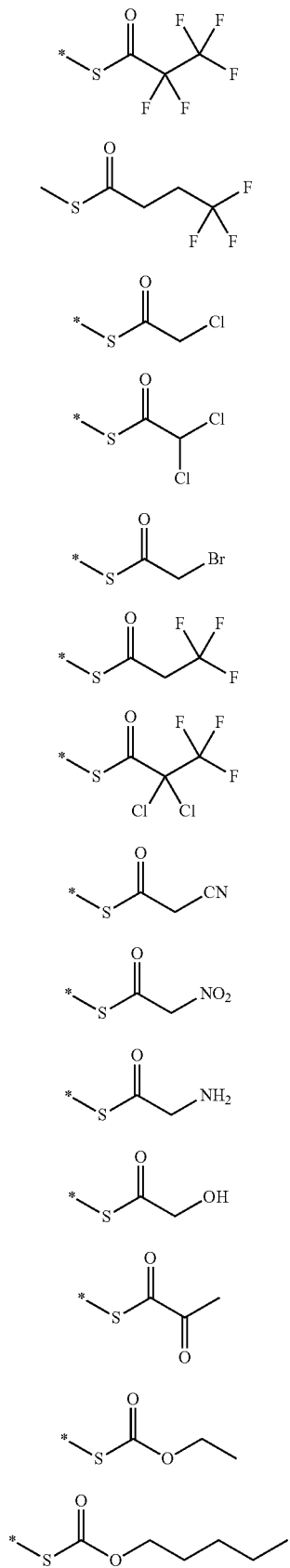
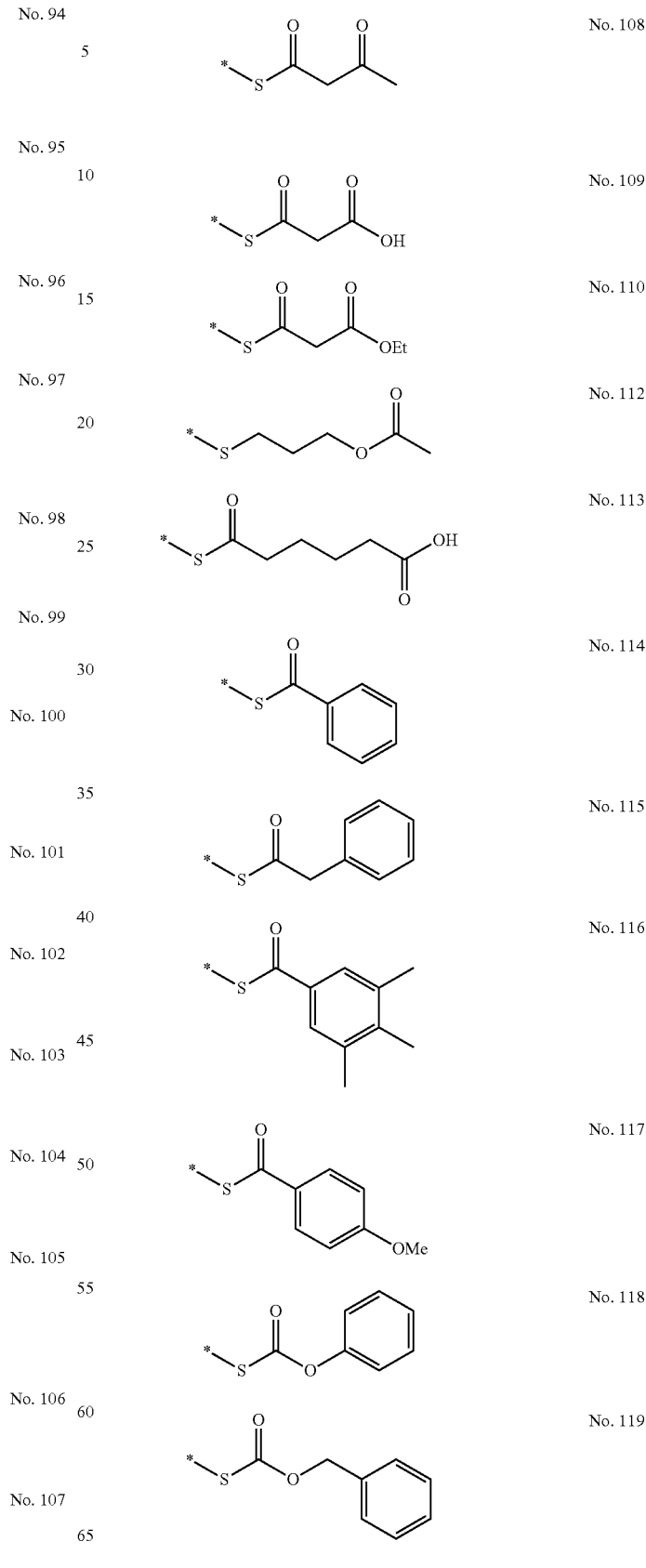

TABLE 1-continued
| | |
|---|---|
| 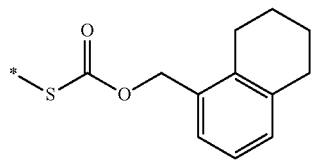 | No. 120 |
| 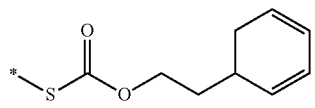 | No. 121 |
| 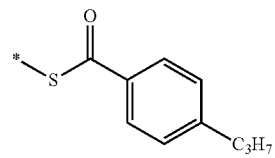 | No. 122 |
| 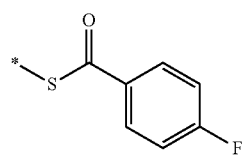 | No. 123 |
| 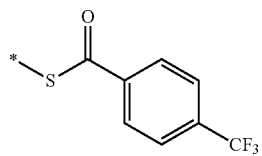 | No. 124 |
| 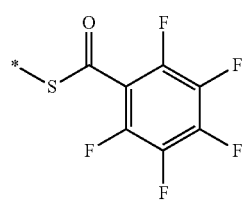 | No. 125 |
| 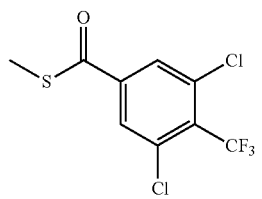 [SMILES: CSC(=O)c1cc(Cl)c(C(F)(F)F)c(Cl)c1] | No. 126 |
| 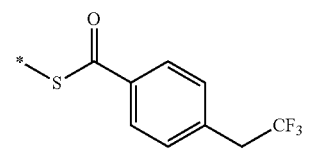 | No. 127 |
| 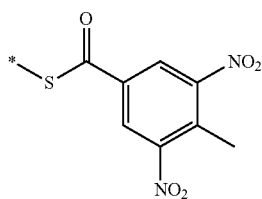 | No. 128 |
| 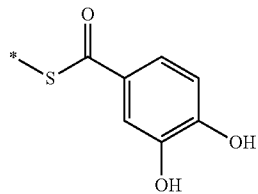 | No. 129 |
| 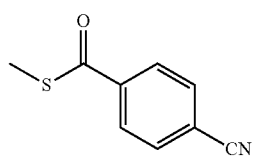 | No. 130 |
| 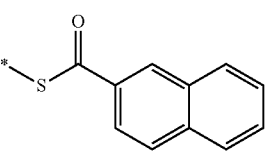 | No. 131 |
| 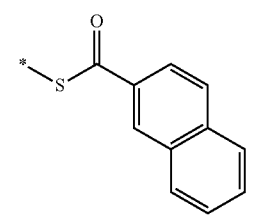 | No. 132 |
| 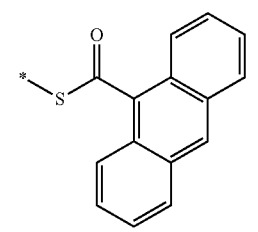 | No. 133 |
| 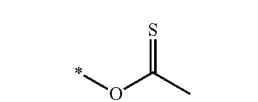 | No. 134 |
| 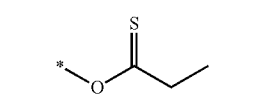 | No. 135 |
| 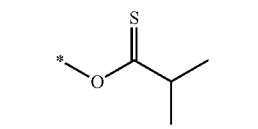 | No. 136 |
| 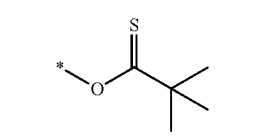 | No. 137 |
| 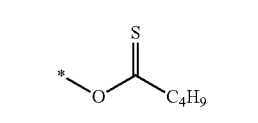 | No. 138 |

TABLE 1-continued
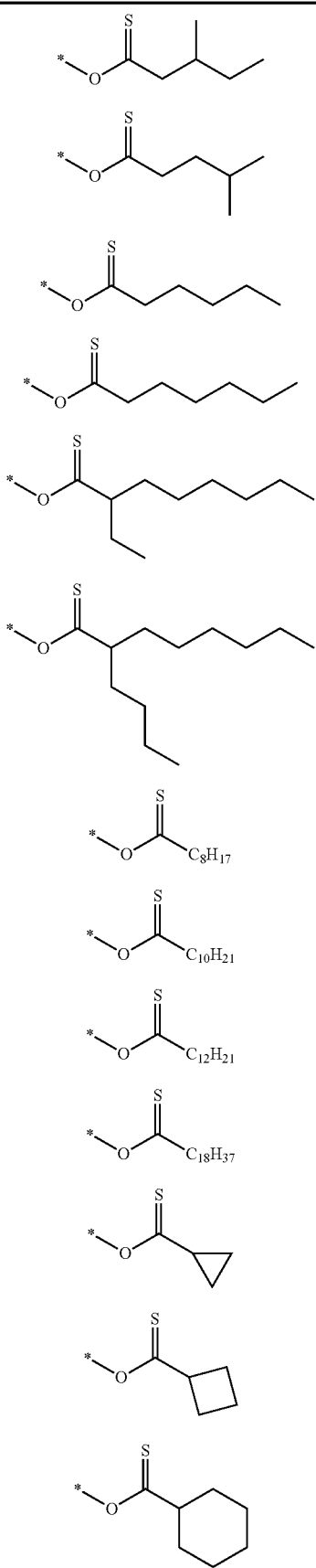
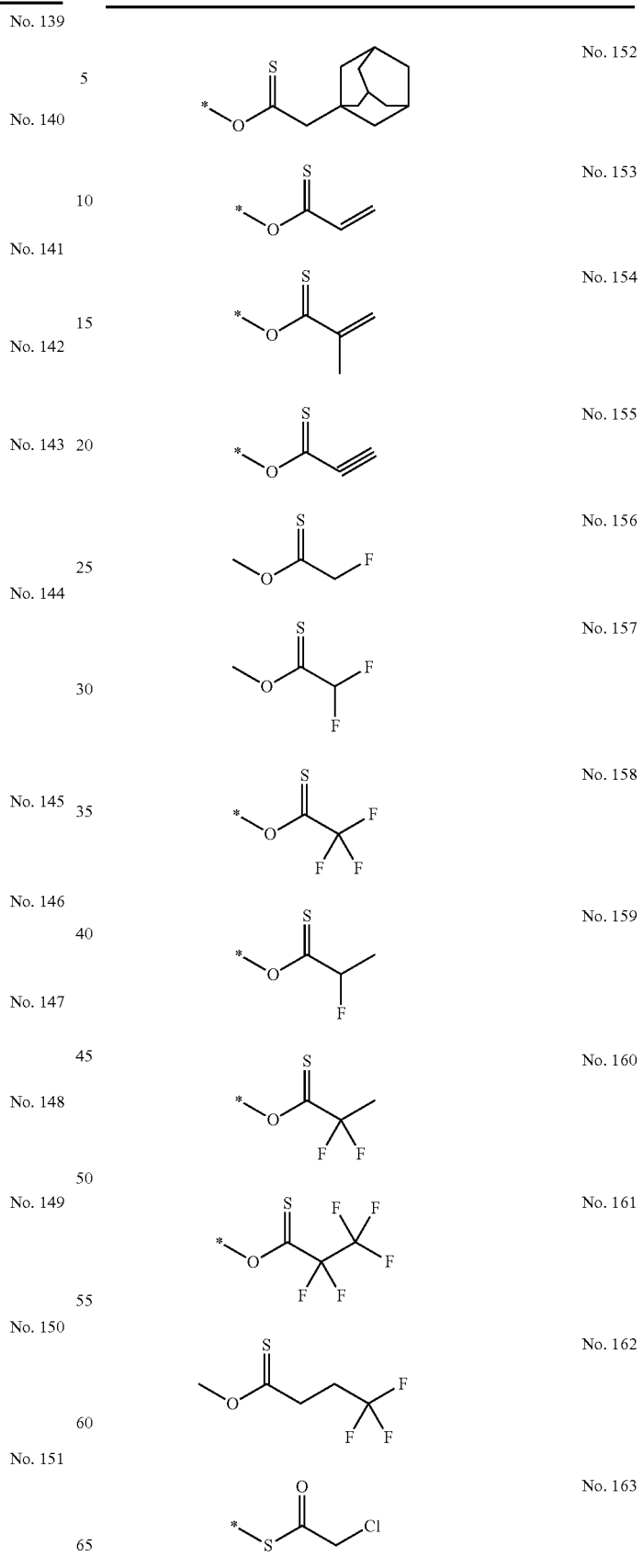

TABLE 1-continued
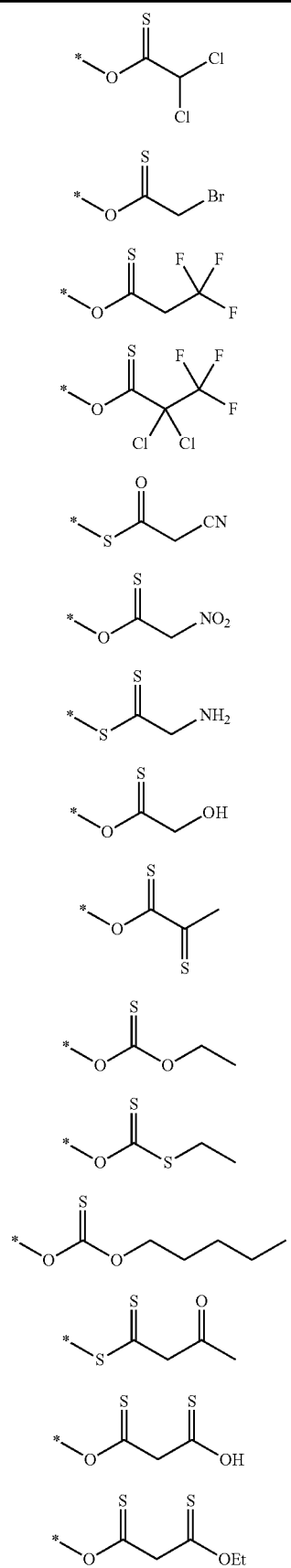
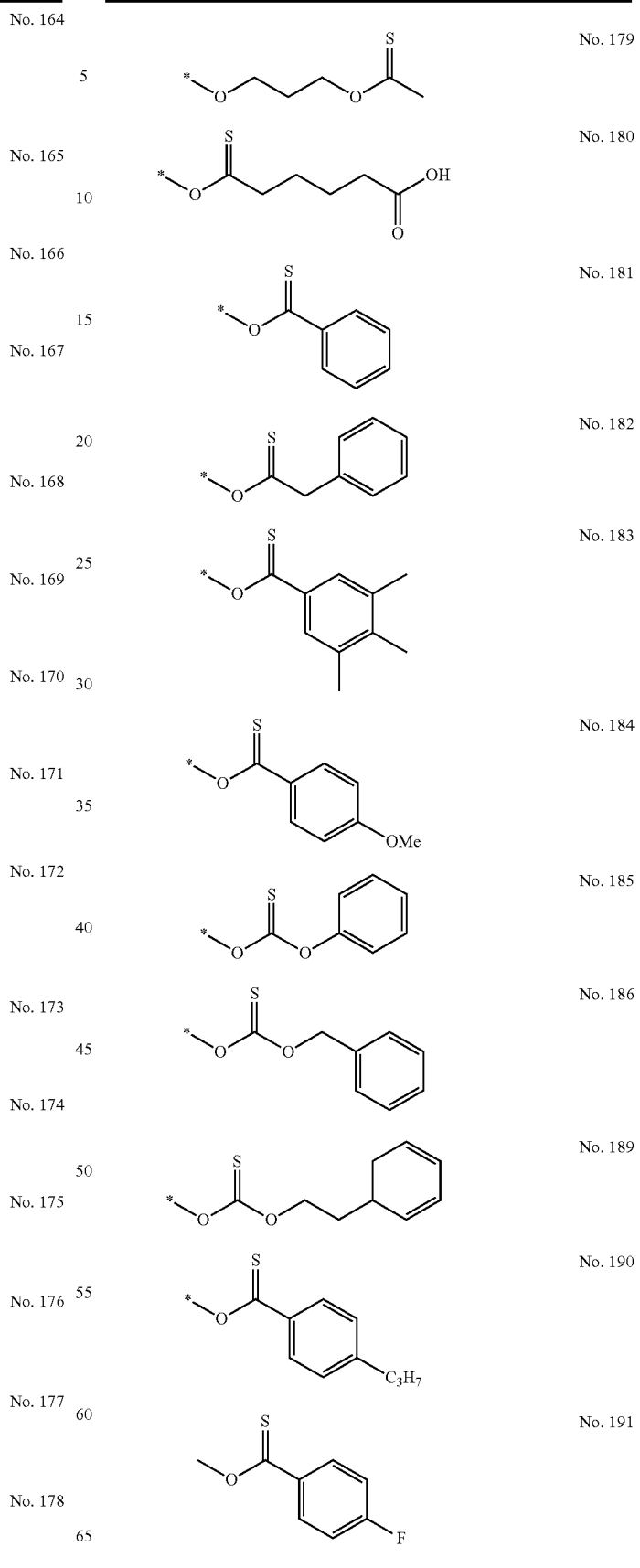

TABLE 1-continued
| | |
|---|---|
| 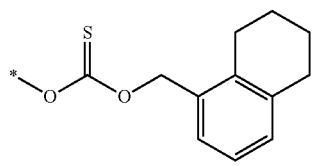 | No. 192 |
| 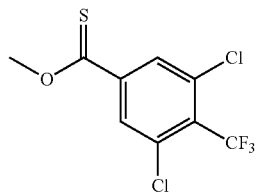 [SMILES: COC(=S)c1cc(Cl)c(C(F)(F)F)c(Cl)c1] | No. 193 |
| 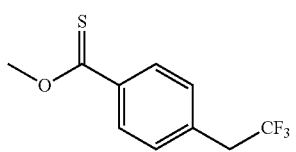 | No. 194 |
| 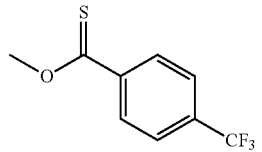 | No. 195 |
| 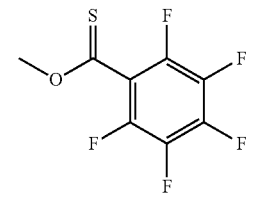 | No. 196 |
| 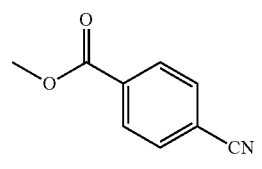 | No. 197 |
| 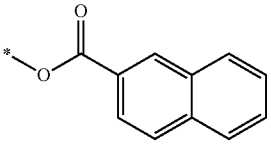 | No. 198 |
| 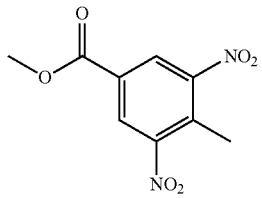 [SMILES: COC(=O)c1cc([N+](=O)[O-])c(C)c([N+](=O)[O-])c1] | No. 199 |
| 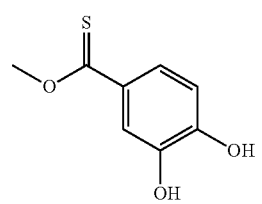 | No. 200 |
TABLE 1-continued
| | |
|---|---|
| 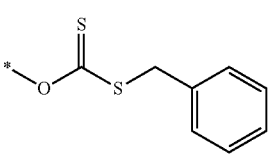 | No. 201 |
| 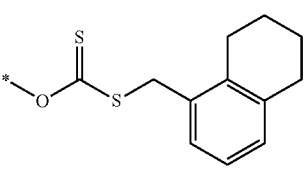 | No. 202 |
| 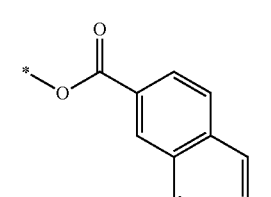 | No. 203 |
| 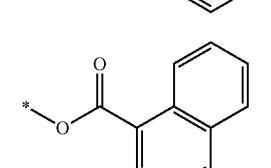 | No. 204 |
| 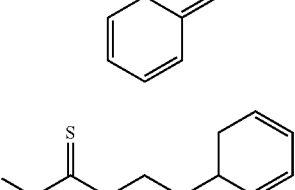 | No. 205 |
| 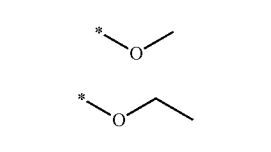 | No. 206 |
| 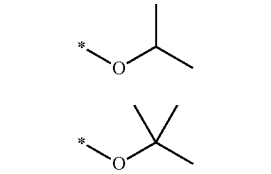 | No. 207 |
| 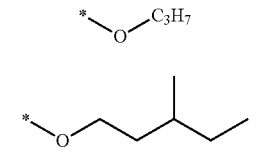 | No. 208 |
| 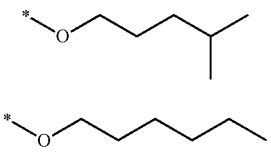 | No. 209 |
| 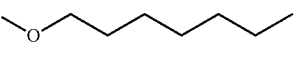 | No. 210 |
|  | No. 211 |
|  | No. 212 |
|  | No. 213 |
| | No. 214 |

TABLE 1-continued
| Structure | No. |
|---|---|
| 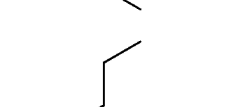 | No. 215 |
| 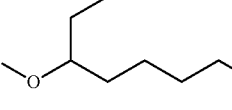 | No. 216 |
| *―O―C₇H₁₅ | No. 217 |
| *―O―C₁₀H₂₁ | No. 218 |
| *―O―C₁₂H₂₅ | No. 219 |
| *―O―C₁₈H₃₇ | No. 220 |
| 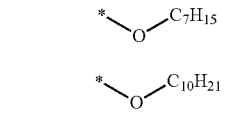 | No. 221 |
| 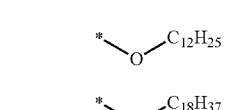 | No. 222 |
| 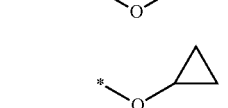 | No. 223 |
| 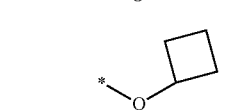 | No. 224 |
| 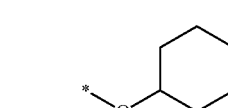 | No. 225 |
| 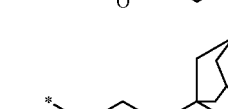 | No. 226 |
| 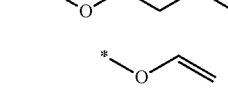 | No. 227 |
| 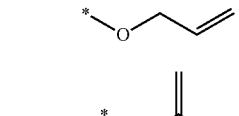 | No. 228 |
| 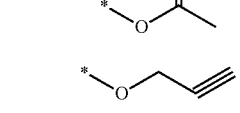 | No. 229 |
| 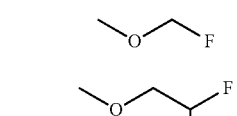 | No. 230 |
| 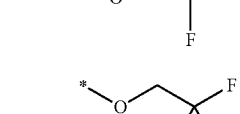 | No. 231 |
| 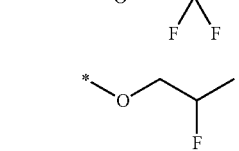 | No. 232 |
TABLE 1-continued
| Structure | No. |
|---|---|
|  | No. 233 |
|  | No. 234 |
| 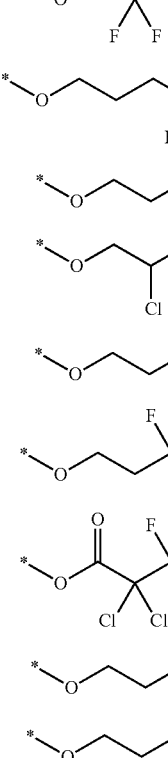 | No. 235 |
| 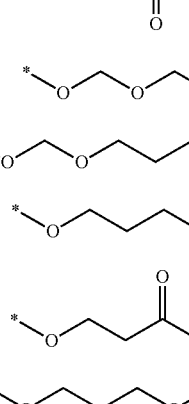 | No. 236 |
| 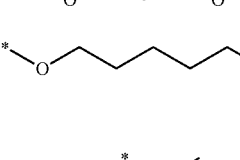 | No. 237 |
| *―O―CH₂CH₂―Br | No. 238 |
| 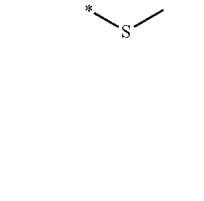 | No. 239 |
| (structure) | No. 240 |
| *―O―CH₂CH₂―CN | No. 241 |
| *―O―CH₂CH₂―NO₂ | No. 242 |
| *―O―CH₂CH₂―NH₂ | No. 243 |
| (structure) | No. 244 |
| (structure) | No. 245 |
| (structure) | No. 246 |
| (structure) | No. 247 |
| (structure) | No. 248 |
| (structure) | No. 249 |
| (structure) | No. 250 |
| *―S―CH₃ | No. 251 |

TABLE 1-continued
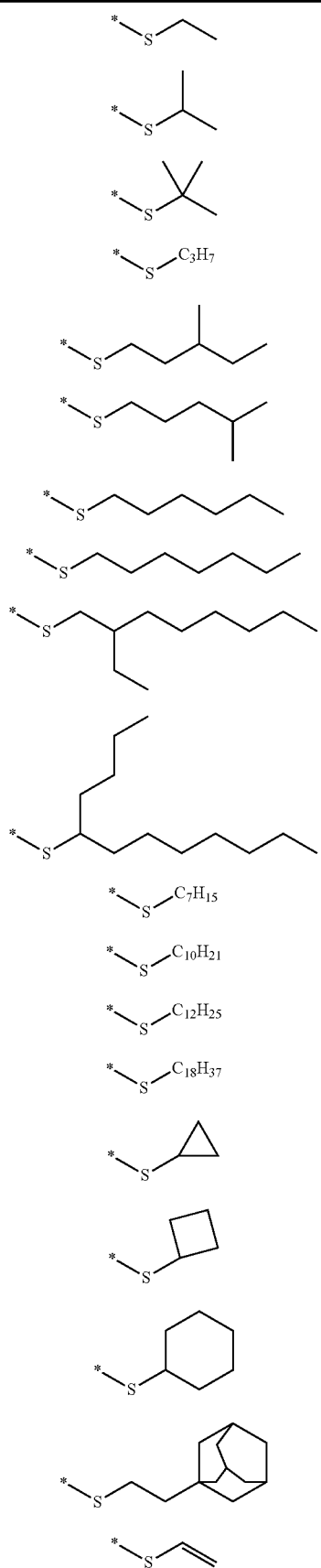
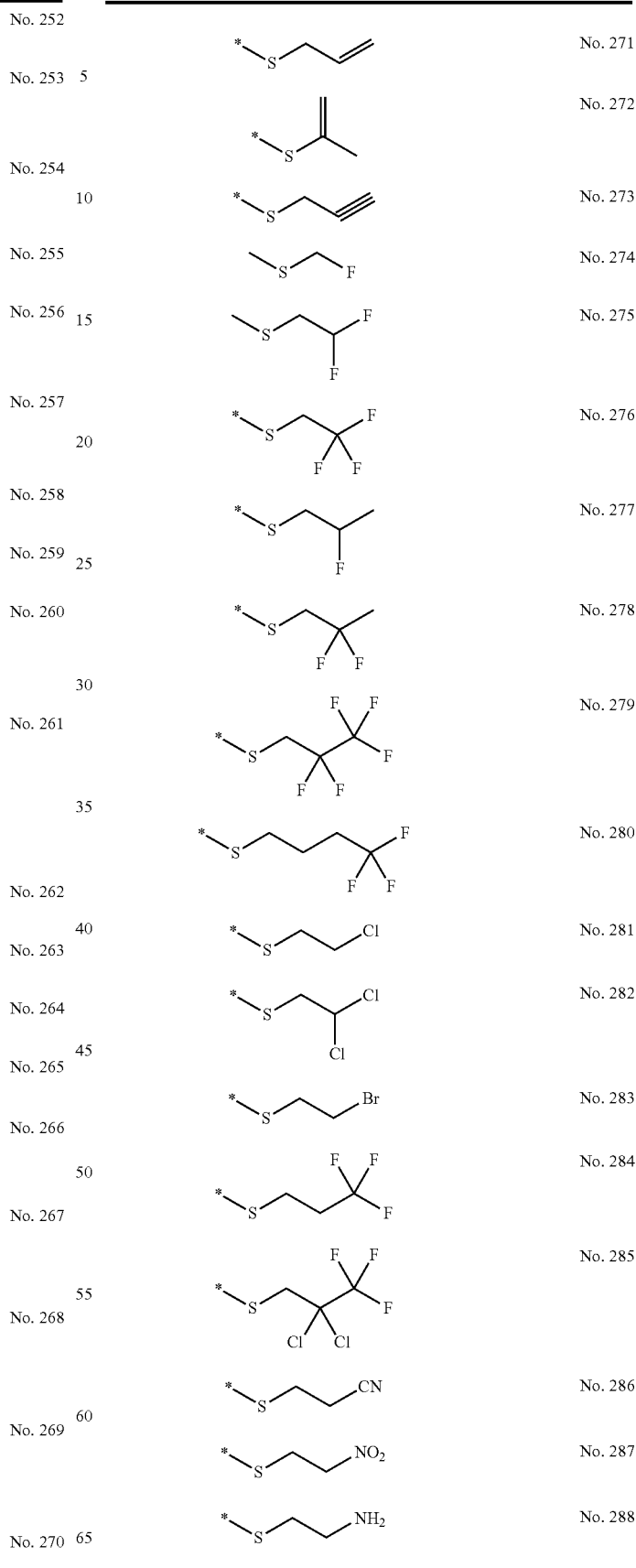

TABLE 1-continued
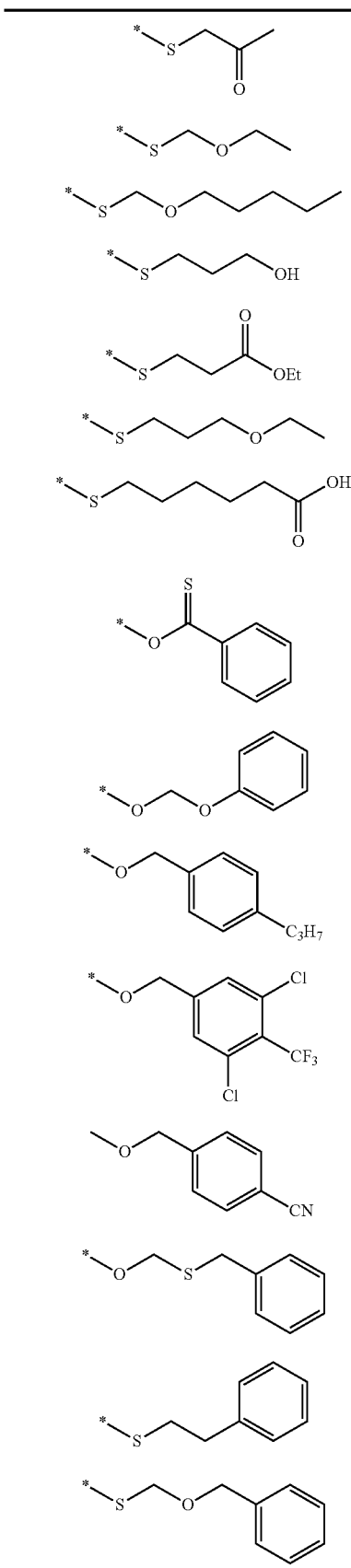
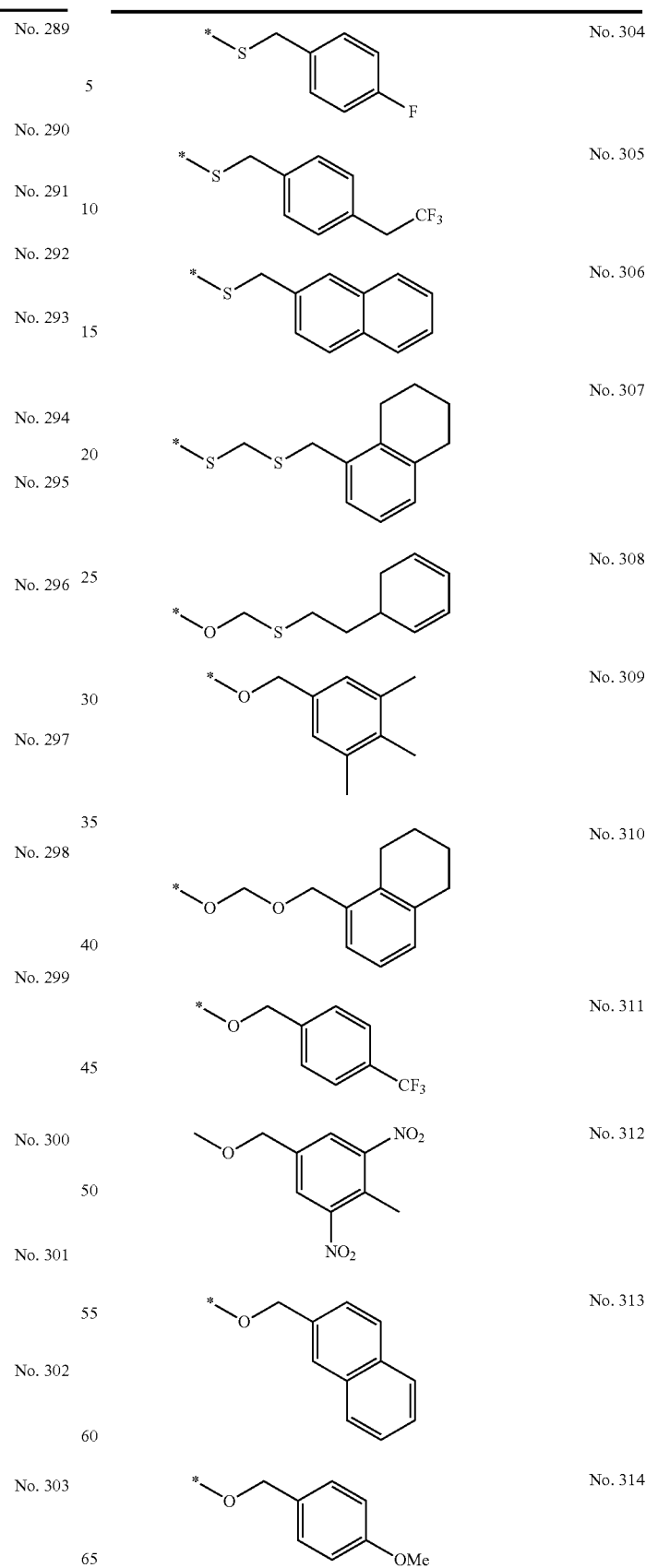

TABLE 1-continued

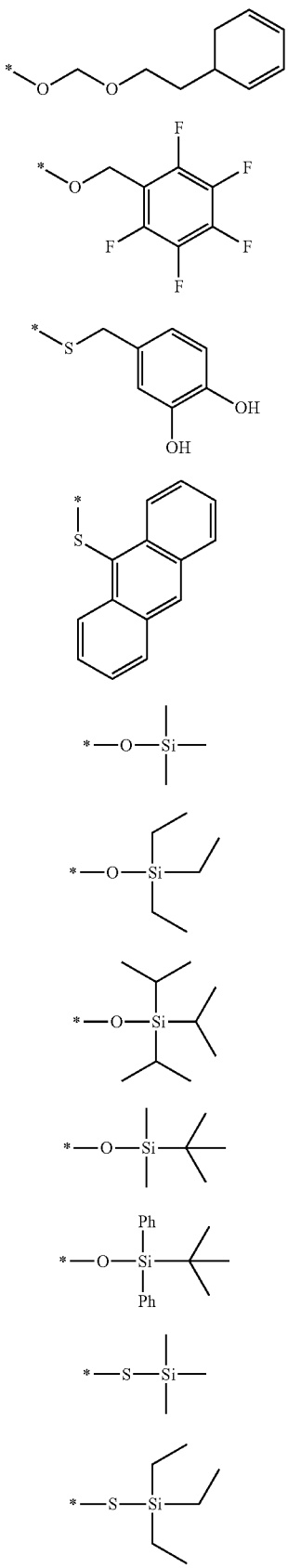

No. 315
No. 316
No. 317
No. 318
No. 319
No. 320
No. 321
No. 322
No. 323
No. 324
No. 325

TABLE 1-continued

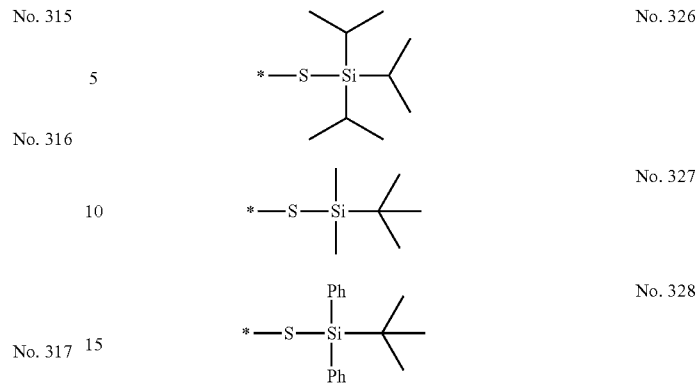

No. 326
No. 327
No. 328

In one embodiment, introduction of the substituted or unsubstituted ether group or acyloxy group having one or more carbon atoms (leaving group) enables the compound to perform elimination reaction of its leaving group by energy (heat) lower than in the conventional compounds while the compound maintains its high dissolvability to an organic solvent and its stability.

As the leaving group, a substituted or unsubstituted sulfonyloxy group having one or more carbon atoms may be used instead of the substituted or unsubstituted ether group or acyloxy group having one or more carbon atoms.

Examples of the above substituted or unsubstituted sulfonyloxy group include sulfonyloxy groups derived from sulfonic acids such as linear or cyclic aliphatic sulfonic acids, having one or more carbon atoms and aromatic sulfonic acids having four or more carbon atoms. Specific examples thereof include a methylsulfonyloxy group, an ethylsulfonyloxy group, an isopropylsulfonyloxy group, a pivaloylsulfonyloxy group, a pentanoylsulfonyloxy group, a hexanoylsulfonyloxy group, a trifluoromethanesulfonyloxy group, a 3,3,3-trifluoropropionylsulfonyloxy group, a phenylsulfonyloxy group and a p-toluenesulfonyloxy group. Further examples include sulfonylthiooxy groups, which the oxygen atom in the ether bond of the above sulfonyloxy groups is replaced with the sulfur atom. The number of carbon atoms contained in the above sulfonyloxy group is generally 1 to 38, preferably 2 to 22, more preferably 3 to 18, considering various factors such as solubility and the boiling point of the eliminated component.

In one embodiment, the groups represented by Q1 to Q6 are, as described above, the hydrogen atom, the halogen atom (e.g., a fluorine atom, a chlorine atom, a bromine atom or an iodine atom), the organic group (provided that Q1 and Q6 are monovalent organic groups other than the substituted or unsubstituted ether group or acyloxy group having one or more carbon atoms), or the atomic bonding to combine with a neighboring carbon atom or nitrogen atom.

Examples of the organic group include alkyl groups, alkenyl groups, alkynyl groups, aryl groups, heteroaryl groups, aralkyl group, alkoxyl groups, thioalkoxyl groups, aryloxy groups, thioaryloxy groups, heteroaryloxy groups, heteroarylthiooxy groups, a cyano group, a hydroxyl group, a nitro group, a carboxyl group, a thiol group and an amino group.

The above alkyl group is a linear, branched or cyclic, substituted or unsubstituted alkyl group.

Examples of the alkyl group include alkyl groups (preferably, substituted or unsubstituted alkyl groups having one or more carbon atoms such as a methyl group, an ethyl group, a n-propyl group, an i-propyl group, a t-butyl group, a s-butyl group, a n-butyl group, an i-butyl group, a pentyl group, a hexyl group, a heptyl group, an octyl group, a nonyl group, a decyl group, an undecyl group, a dodecyl group, a tridecyl group, a tetradecyl group, a pentadecane group, a hexadecyl group, a heptadecyl group, an octadecyl group, a 3,7-dimethyloctyl group, a 2-ethylhexyl group, a trifluoromethyl group, a trifluorooctyl group, a trifluorododecyl group, a trifluorooctadecyl group and a 2-cyanoethyl group), cycloalkyl groups (preferably, substituted or unsubstituted alkyl groups having three or more carbon atoms such as a cyclopentyl group, a cyclobutyl group, a cyclohexyl group and a pentafluorocyclohexyl group), a 1-adamantyl group, and a 2-adamantyl group.

The above alkenyl group is a linear, branched or cyclic, substituted or unsubstituted alkenyl group. Examples of the alkenyl group include alkenyl groups (preferably, substituted or unsubstituted alkenyl groups having two or more carbon atoms obtained by changing one or more carbon-carbon single bonds to a double bond in the above-exemplified alkyl groups having two or more carbon atoms (e.g., an ethenyl group (a vinyl group), a propenyl group (an allyl group), a 1-butenyl group, a 2-butenyl group, a 2-methyl-2-butenyl group, a 1-pentenyl group, a 2-pentenyl group, a 3-pentenyl group, a 1-hexenyl group, a 2-hexenyl group, a 3-hexenyl group, a 1-heptenyl group, a 2-heptenyl group, a 3-heptenyl group, a 4-heptenyl group, a 1-octenyl group, a 2-octenyl group, a 3-octenyl group, a 4-octenyl group and a 1,1,1-trifluoro-2-butenyl group)) and cycloalkenyl groups obtained by changing one or more carbon-carbon single bonds to a double bond in the above-exemplified cycloalkyl groups having two or more carbon atoms (e.g., a 1-cycloallyl group, a 1-cyclobutenyl group, a 1-cyclopentenyl group, a 2-cyclopentenyl group, a 3-cyclopentenyl group, a 1-cyclohexenyl group, a 2-cyclohexenyl group, a 3-cyclohexenyl group, a 1-cycloheptenyl group, a 2-cycloheptenyl group, a 3-cycloheptenyl group, a 4-cycloheptenyl group and a 3-fluoro-1-cyclohexenyl group)). When the alkenyl group has stereoisomers such as a trans (E) form and cis (Z) form, both the stereoisomers may be used, or a mixture containing them at any ratio may be used also.

The above alkynyl group is preferably a substituted or unsubstituted alkynyl group having two or more carbon atoms such as groups obtained by changing one or more carbon-carbon single bonds to a triple bond in the above-exemplified alkyl groups having two or more carbon atoms. Examples thereof include an ethynyl group, a proparygyl group, a trimethylsilylethynyl group and a triisopropylsilylethynyl group.

The above aryl group is preferably a substituted or unsubstituted aryl group having six or more carbon atoms (e.g., a phenyl group, an o-tolyl group, a m-tolyl group, a p-tolyl group, a p-chlorophenyl group, a p-fluorophenyl group, a p-trifluorophenyl group and a naphthyl group).

The above heteroaryl group is preferably 5- or 6-membered substituted or unsubstituted, aromatic or non-aromatic heterocyclic groups (e.g., a 2-furyl group, a 2-thienyl group, a 3-thienyl group, a 2-thienothienyl group, a 2-benzothienyl group and a 2-pyrimidyl group)).

The aralkyl group may have 6 to 49 carbon atoms in its aryl moiety and 1 to 44 carbon atoms in its alkyl moiety. Examples thereof include a benzyl group, a 1-phenylethyl group, a 2-phenylethyl group, 1-phenylisopropyl group, 2-phenylisopropyl group, a phenyl-t-butyl group, α-naphthylmethyl group, 1-α-naphthylethyl group, 2-α-naphthylethyl, 1-α-naphthylisopropyl group, 2-α-naphthylisopropyl group, β-naphthylbethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzil group, m-methylbenzil group, o-methylbenzil group, p-chlorobenzil group, m-chlorobenzil group, o-chlorobenzil group, p-bromobenzil group, m-bromobenzil group, o-bromobenzil group, p-iodobenzil group, m-iodobenzil group, o-iodobenzil group, p-hydroxybenzil group, m-hydroxybenzil group, o-hydroxybenzil group, p-aminobenzil group, m-aminobenzil group, o-aminobenzil group, p-nitrobenzil group, m-nitrobenzil group, o-nitrobenzil group, p-cyanobenzil group, m-cyanobenzil group, o-cyanobenzil group, 1-hydroxy-2-phenylisopropyl group, 1-chloro-2-phenylisopropyl group.

The above alkoxyl group and thioalkoxyl group are preferably substituted or unsubstituted alkoxyl groups and thioalkoxyl groups such as groups obtained by introducing an oxygen atom or a sulfur atom into the binding site of the above-exemplified alkyl, alkenyl and alkynyl groups.

The above aryloxy group and thioaryloxy group are preferably substituted or unsubstituted aryloxy groups and thioaryloxy groups such as groups obtained by introducing an oxygen atom or a sulfur atom into the binding site of the above-exemplified aryl groups.

The above heteroaryloxy group and heterothioaryloxy group are preferably substituted or unsubstituted heteroaryloxy groups and heteroarylthiooxy groups such as groups obtained by introducing an oxygen atom or a sulfur atom into the binding site of the above-exemplified heteroaryl groups.

The above amino group is preferably an amino group, substituted or unsubstituted alkylamino groups, substituted or unsubstituted anilino groups such as an amino group, a methylamino group, a dimethylamino group, an anilino group, an N-methyl-anilino group and a diphenylamino group; an acylamino group (preferably, a formylamino group, a substituted or unsubstituted alkylcarbonylamino group and a substituted or unsubstituted arylcarbonylamino group (e.g., a formylamino group, an acetylamino group, a pivaloylamino group, a lauroylamino group, a benzoylamino group and a 3,4,5-tri-n-octyloxyphenylcarbonylamino group)) and an aminocarbonylamino group (preferably, a carbon-substituted or unsubstituted aminocarbonylamino group (e.g., a carbamoylamino group, an N,N-dimethylaminocarbonylamino group, an N,N-diethylaminocarbonylamino group and a morpholinocarbonylamino group)).

The organic groups represented by $Q_1$ to $Q_6$ may be those described above. Preferably, they are substituted or unsubstituted aryl groups or heteroaryl groups, or form ring structures together with the adjacent groups. More preferably, the ring structures are formed of substituted or unsubstituted aryl groups or heteroaryl groups Examples of forming the bond or condensing the ring structures are expressed by the following I-(1) to I-(42), which are derived from the compound shown in formula (1-2). In addition the compound shown in formula (1-1) may be used similarly.

TABLE 2
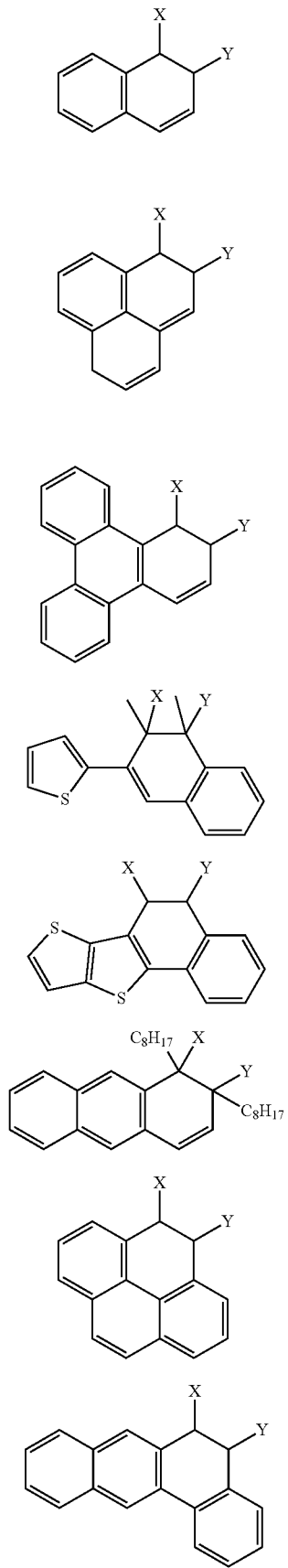
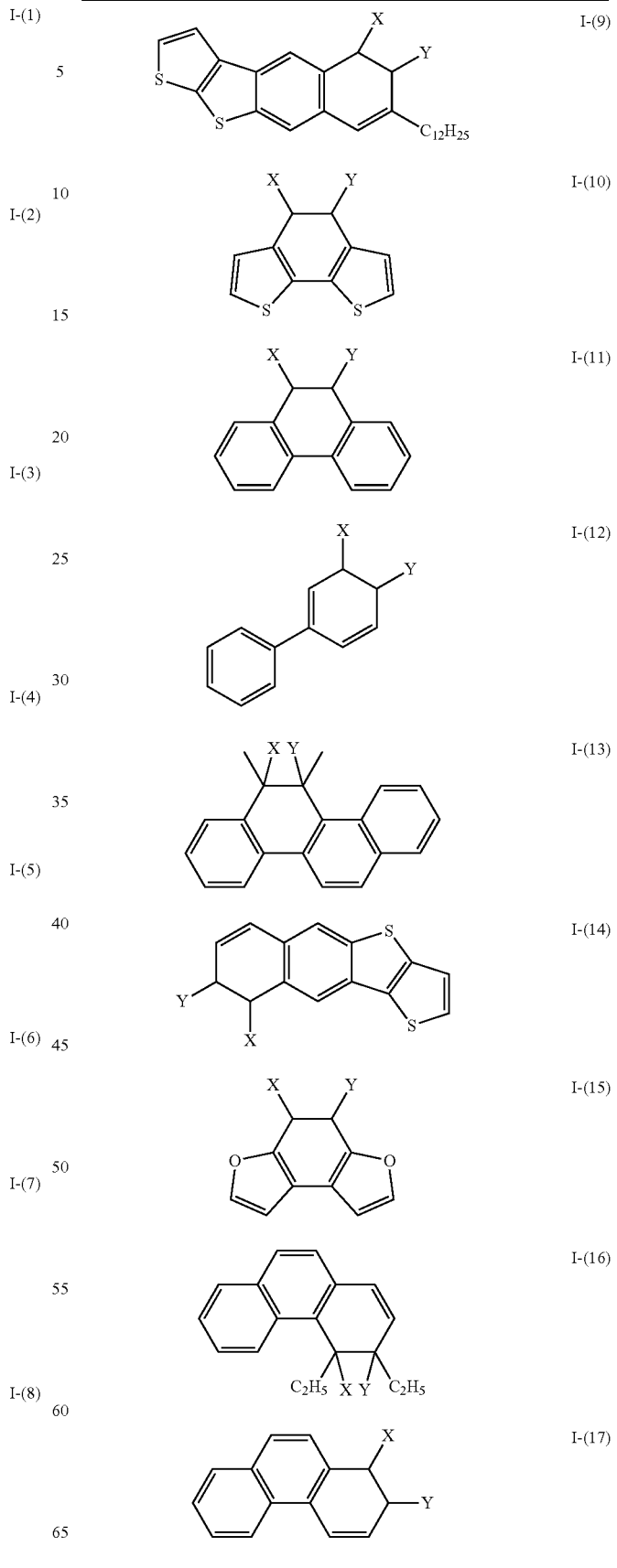

TABLE 2-continued

I-(18)
I-(19)
I-(20)
I-(21)
I-(22)
I-(23)
I-(24)
I-(25)

TABLE 2-continued

I-(26)
I-(27)
I-(28)
I-(29)
I-(30)
I-(31)
I-(32)

TABLE 2-continued

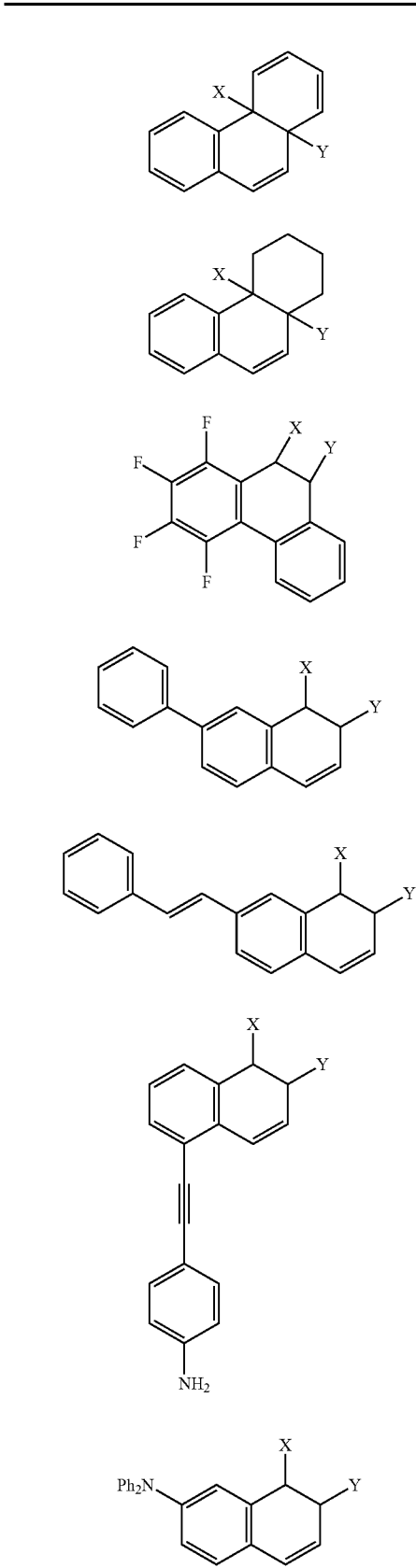

I-(33)
I-(34)
I-(35)
I-(36)
I-(37)
I-(38)
I-(39)

TABLE 2-continued

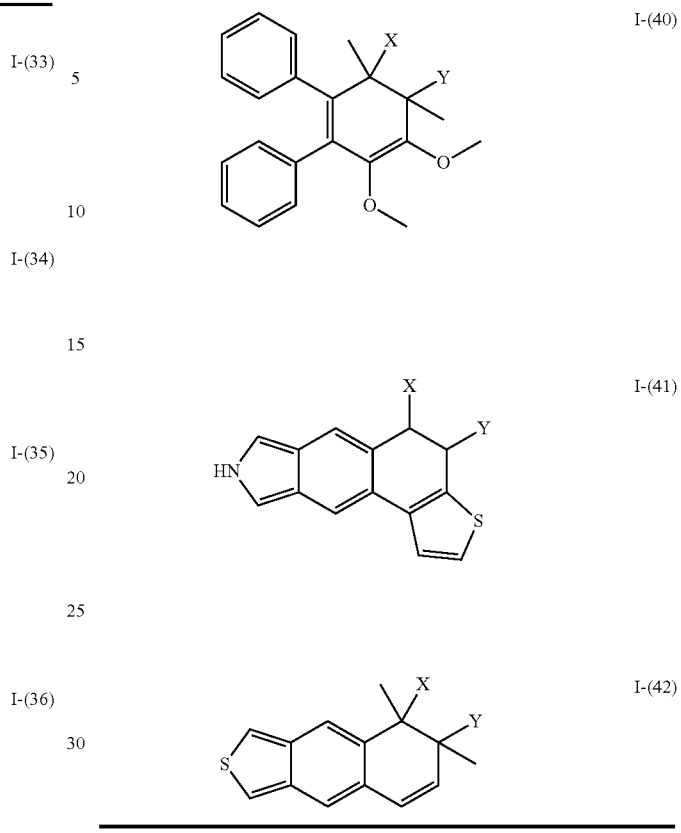

I-(40)
I-(41)
I-(42)

Preferred examples of the substituted or unsubstituted aryl or heteroaryl group include a benzene ring, a thiophene ring, a pyridine ring, a pyrazine ring, a pyrimidine ring, a triazine ring, a pyrrol ring, a pyrazole ring, an imidazole ring, a triazole ring, an oxazole ring, a thiazole ring, a furan ring, a thiophene ring, a selenophene ring and a silole ring. More preferred are (i) compounds in which one or more of the above aryl groups, heteroaryl groups and rings are condensed together and (ii) compounds in which the rings in (i) are linked together via a covalent bond.

Also, preferred is at least one π-electron conjugated compound selected from the group consisting of the compounds in (i) and the compounds in (ii). Further, π-electrons contained in the aromatic hydrocarbon rings or aromatic heterocyclic rings are preferably delocalized across entire the condensed ring or linked ring by the interaction of link through the condensed ring or a covalent bond.

Here, the "covalent bond" may be, for example, a carbon-carbon single bond, a carbon-carbon double bond, a carbon-carbon triple bond, an oxyether bond, a thioether bond, an amide bond and an ester bond, with a single bond, a double bond and a carbon triple bond being preferred.

(Conversion of the Substituent Having the Leaving Group)

The substituent having the leaving group, which may be a soluble substituent, leaves the leaving group to convert its structure.

The soluble substituent shown in formula (Ia or Ib) leaves X—Y (IIIa), or $X_1$—$Y_1$ (IIIb$_1$) and $X_2$—$Y_2$ (IIIb2), which are composed of the leaving group and the hydrogen atom, to convert its structure to a corresponding benzene structure (II).

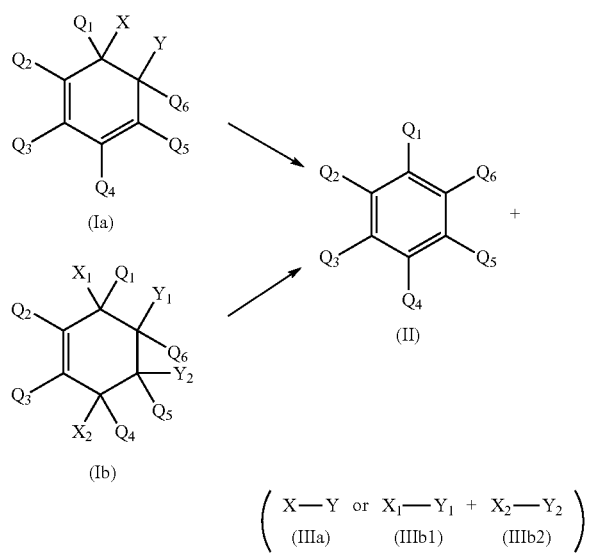

The elimination reaction is caused depending on a structure of its functional group and generally caused by applying an external energy in terms of reaction speed and yield.

Examples of the energie applied for causing the elimination reaction include heat, light and electromagnetic wave. Heat or light is preferred in terms of reactivity, yield or post treatment. Particularly preferred is heat. Alternatively, in the presence of acid or base, the aforementioned energies may be applied.

Examples of heating methods for causing elimination reaction include, but not limited thereto, a method for heating on a support, a method for heating in an oven, a method for irradiation with microwave, a method for heating by converting light to heat using a laser beam, and a method using a photothermal conversion layer.

Heating temperature for causing elimination reaction may be a room temperature (approximately 25° C.) to 500° C. In consideration of thermal stability of the materials and a boiling point of the eliminated components as to the lower limit of the temperature, and in consideration of energy efficiency, percentage of the presence of unconverted molecule, and the sublimation and decomposition of the compound after conversion as to the upper limit of the temperature, the temperature is preferably 40° C. to 500° C. Moreover, in consideration of thermal stability of the leaving group-containing compound during synthesis, the temperature is more preferably 60° C. to 500° C., and particularly preferably 80° C. to 400° C.

When it is applied to an active layer of an organic EL, the heating temperature is preferably lower than a glass-transition temperature and melting point of a corresponding arylamine compound after elimination, to avoid crystallization and melting, and to obtain an amorphous film. In this case, the heating temperature is preferably 30° C. to 250° C., more preferably, 40° C. to 250° C., even more preferably 60° C. to 150° C. However, even if the heating temperature is more than the glass-transition temperature, the film, which is obtained by thermal conversion, keeps amorphous state, i.e. the arylamine compound of this embodiment does not show similar crystallization behavior compare to the case when the film of the corresponding arylamine compound, which has double bonding instead of the leaving group, is heated. It is not known exactly why it is.

As to the heating time, the higher the temperature is, the shorter the reaction time becomes. The lower the temperature is, the longer the time required for elimination reaction becomes. Heating time depends on the reactivity and amount of the aryl amine compound having leaving substituent, and is generally 0.5 min to 120 min, preferably 1 min to 60 min, and particularly preferably 1 min to 30 min.

In the case where light is used as the external energy, for example, infrared lamp or irradiation of light of wavelength absorbed by a compound (for example, exposure to light of wavelength 405 nm or less) may be used. On this occasion, a semiconductor laser may be used. Examples of semiconductor laser beam include a near-infrared region laser beam (generally, a laser beam of wavelength around 780 nm), a visible laser beam (generally, a laser beam of wavelength in the range of 630 nm to 680 nm), and a laser beam of wavelength of 390 nm to 440 nm. Particularly preferable laser beam is a laser beam having a wavelength region of 390 nm to 440 nm and a semiconductor laser beam having a laser emission wavelength of 440 nm or less. Among these semiconductor laser beam, examples of preferable light sources include a bluish-violet semiconductor laser beam having an emission wavelength region of 390 nm to 440 nm (more preferably from 390 nm to 415 nm), and a bluish-violet SHG laser beam having a center emission wavelength of 425 nm that has been converted to a half wavelength of the infrared semiconductor laser beam having a center emission wavelength of 850 nm by using an optical waveguide element.

In the elimination reaction of the leaving substituents, the acid or base serves as a catalyst, and conversion can be caused at lower temperature. A method of using the acid or base is not particularly limited. Examples of the method include a method in which the acid or base may be directly added to the compound having the leaving substituent, a method in which the acid or base is dissolved in any solvent to form a solution, and the solution is added to the compound having the leaving substituent, a method in which the compound having the leaving substituent is heated in the vaporized acid or base, and a method in which a photoacid generator and a photobase generator are used, and followed by light irradiation, to thereby obtain an acid and base in the reaction system.

Examples of the acids include, but not limited thereto, hydrochloric acid, nitric acid, sulfuric acid, acetic acid, trifluoroacetic acid, trifluoromethanesulfonic acid, 3,3,3-trifluoropropionic acid, formic acid, phosphoric acid and 2-butyl octanoic acid.

Examples of the photoacid generators include ionic photoacid generators such as sulfonium salt, and an iodonium salt; and nonionic photoacid generators such as imide sulfonate, oxime sulfonate, disulfonyl diazomethane, and nitrobenzyl sulfonate.

Examples of the bases include, but not limited thereto, hydroxides such as sodium hydrate, potassium hydrate, carbonates such as sodium hydrogen carbonate, sodium carbonate, potassium carbonate, amines such as triethylamine and pyridine, and amidines such as diazabicycloundecene, diazabicyclononene.

Examples of photobase generators include carbamates, acyloximes, and ammonium salts.

The elimination reaction is preferably performed in a volatile acid or base atmosphere from the standpoint of easiness of removal of the acid or base to the outside of the system after reaction.

The elimination reaction can be performed in an ambient atmosphere regardless of the absence or presence of the catalyst. The elimination reaction is preferably performed in an inert gas atmosphere or reduced pressure in order to reduce any influence of side reaction such as oxidation or influence of moisture, and to promote removal of an eliminated component to outside the system.

Examples of the eliminated component X—Y, $X_1$—$Y_1$, $X_2$—$Y_2$ include alcohols, carboxylic acids and carbonate half esters that are obtained by cleaving the —O— or —S— bonding sites of the above substituted or unsubstituted ether groups or acyloxy groups and replacing the ends of the resultant products with hydrogen.

Examples of the alcohol include methanol, ethanol, propanol, isopropanol, butanol, isobutanol, tert-butyl alcohol, pentanol, hexanol, trifluoromethanol, 3,3,3-trifluoropropanol, 3,3,3-trifluoropropoxy group, pentafluoropropanol, cyclopropanol, cyclobutanol, cyclohexanol, trimethylsilanol, triethylsilanol, tert-butyldimethylsilanol and tert-butyldiphenylsilanol. Further examples include thiols obtained by replacing, with a sulfur atom, the oxygen atom in the ether bonds of the above alcohols.

Examples of the carboxylic acid include formic acid, acetic acid, propionic acid, butyric acid, valeric acid, isovaleric acid, pivalic acid, caproic acid, lauric acid, stearic acid, trifluoroacetic acid, 3,3,3-trifluoropropionic acid, pentafluoropropionic acid, cyclopropanecarboxylc acid, cyclobutanecarboxylc acid, cyclohexanecarboxylc acid, benzoic acid, p-methoxybenzoic acid and pentafluorobenzoic acid. Further examples include thiocarboxylic acids obtained by replacing, with a sulfur atom, the oxygen atom in the ether bonds of the above carboxylic acids.

The eliminated component may be decomposed by the thermal energy depending on its stability. In this case, the component changes to a structure having lower boiling point, it is effective to remove the eliminated component.

When the above substituted or unsubstituted sulfonyloxy group is used, sulfonic acids and thiosulfonic acids are obtained by cleaving the —O— or —S— bonding sites of the sulfonyloxy groups and replacing the ends of the resultant products with hydrogen.

Specific examples include methanesulfonic acid, ethanesulfonic acid, isopropylsulfonic acid, pivaloylsulfonic acid, pentanesulfonic acid, hexanoylsulfonic acid, toluenesulfonic acid, phenylsulfonic acid, trifluoromethanesulfonic acid and 3,3,3-trifluoropropionylsulfonic acid. Further examples include thiosulfonic acids obtained by replacing the oxygen atom in the ether bonds of the above sulfonic acids with a sulfur atom.

The following compounds will be given as specific examples of the arylamine compounds. The arylamine compound of the present invention should not be construed as being limited thereto.

TABLE 3

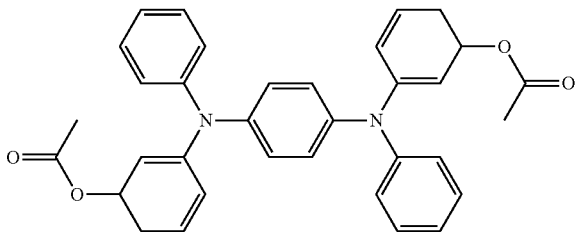 [SMILES: CC(=O)OC1C=C(N(c2ccccc2)c2ccc(N(C3=CC(OC(C)=O)CC=C3)c3ccccc3)cc2)C=CC1]

HTL1

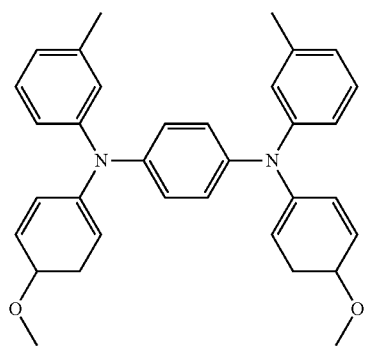 [SMILES: COC1C=CC(N(c2ccc(N(C3=CCC(OC)C=C3)c3cccc(C)c3)cc2)c2cccc(C)c2)=CC1]

HTL2

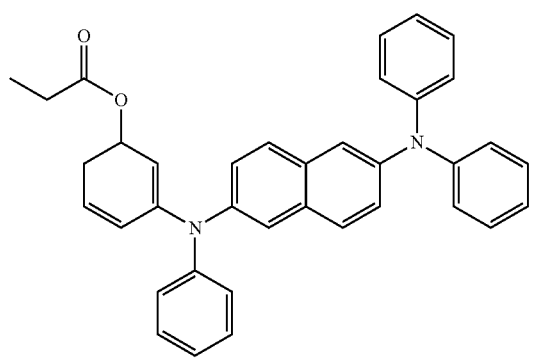 [SMILES: CCC(=O)OC1C=C(N(c2ccccc2)c2ccc3cc(N(c4ccccc4)c4ccccc4)ccc3c2)C=CC1]

HTL3

TABLE 3-continued
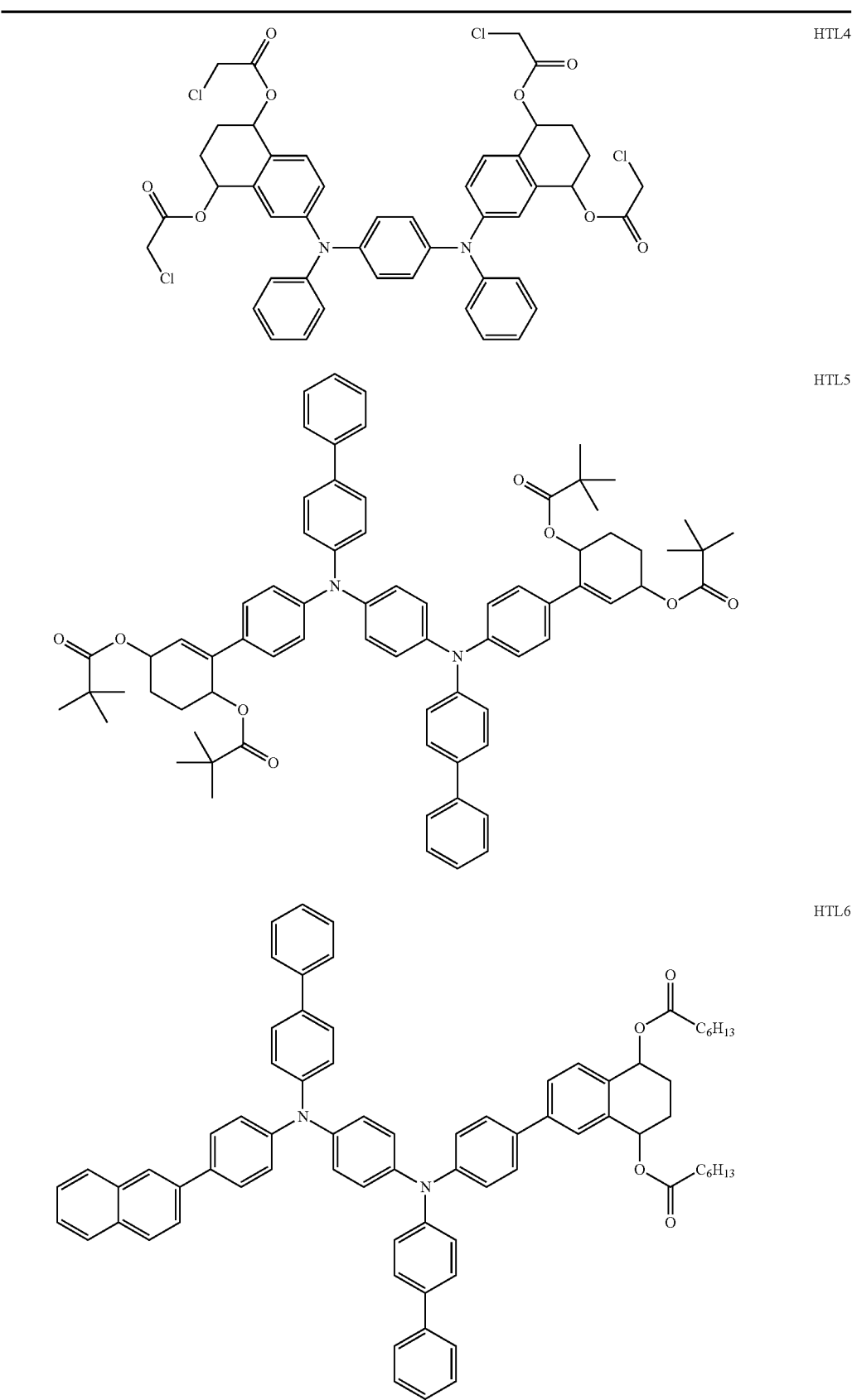

TABLE 3-continued
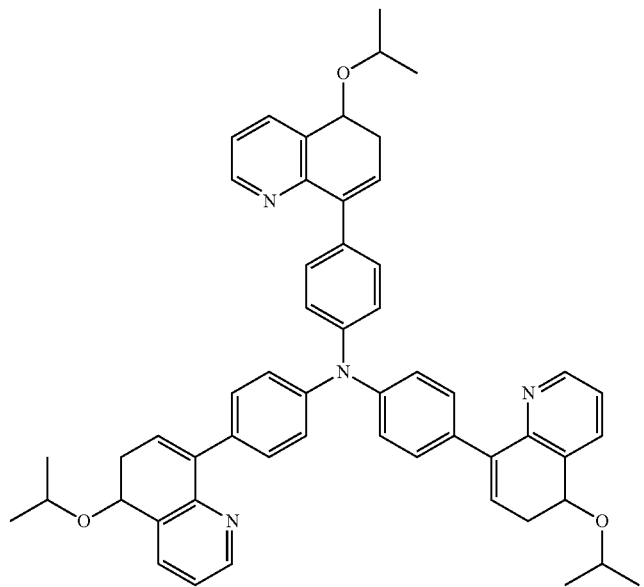 [SMILES: CC(C)OC1CC=C(c2ccc(N(c3ccc(C4=CCC(OC(C)C)c5cccnc54)cc3)c3ccc(C4=CCC(OC(C)C)c5cccnc54)cc3)cc2)c2ncccc21]
HTL7
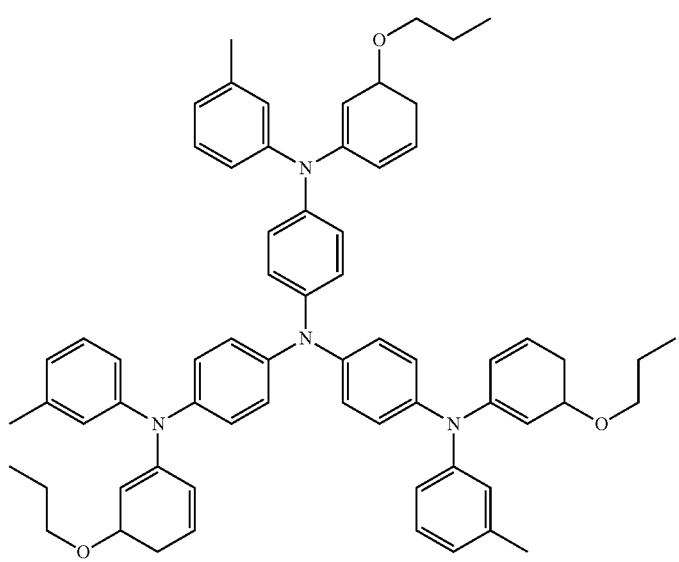 [SMILES: CCCOC1C=C(N(c2ccc(N(c3ccc(N(C4=CC(OCCC)CC=C4)c4cccc(C)c4)cc3)c3ccc(N(C4=CC(OCCC)CC=C4)c4cccc(C)c4)cc3)cc2)c2cccc(C)c2)C=CC1]
HTL8
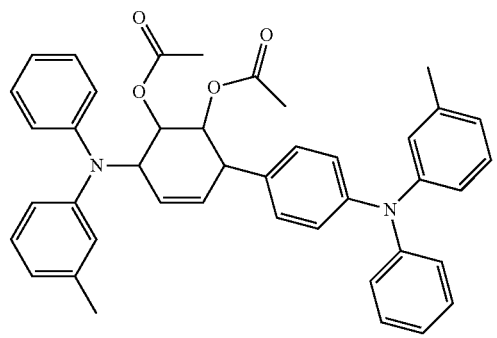 [SMILES: CC(=O)OC1C(c2ccc(N(c3ccccc3)c3cccc(C)c3)cc2)C=CC(N(c2ccccc2)c2cccc(C)c2)C1OC(C)=O]
HTL9

TABLE 3-continued
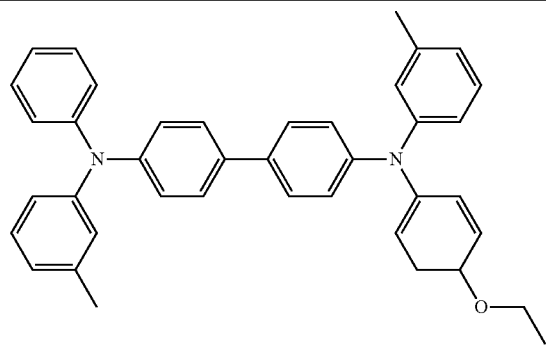
HTL10
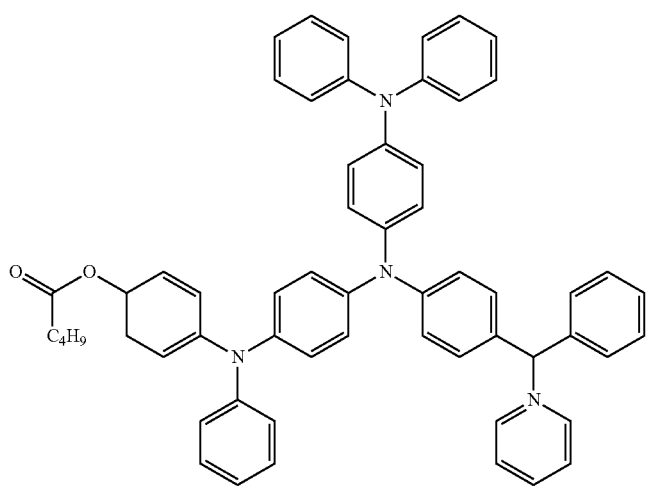
HTL11
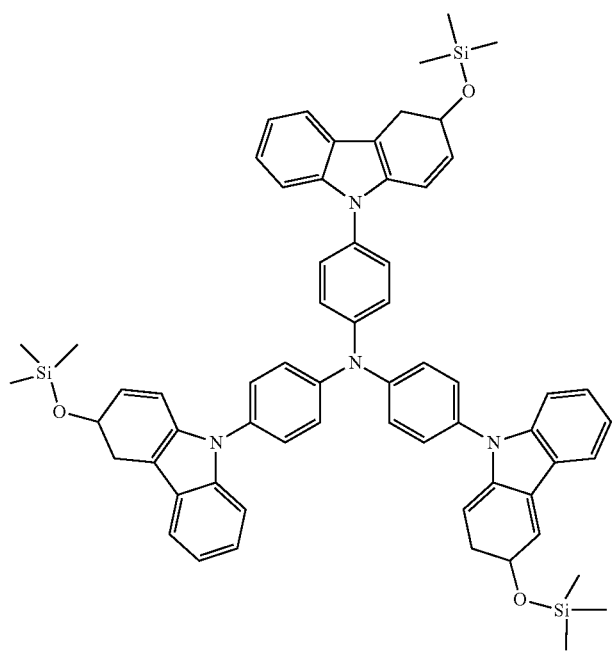 [SMILES: C[Si](C)(C)OC1C=c2c(n(-c3ccc(N(c4ccc(-n5c6c(c7ccccc75)CC(O[Si](C)(C)C)C=C6)cc4)c4ccc(-n5c6c(c7ccccc75)CC(O[Si](C)(C)C)C=C6)cc4)cc3)c3ccccc23)=CC1]
HTL12

TABLE 3-continued
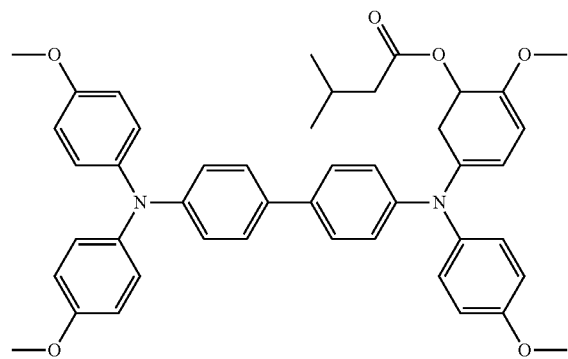
HTL13
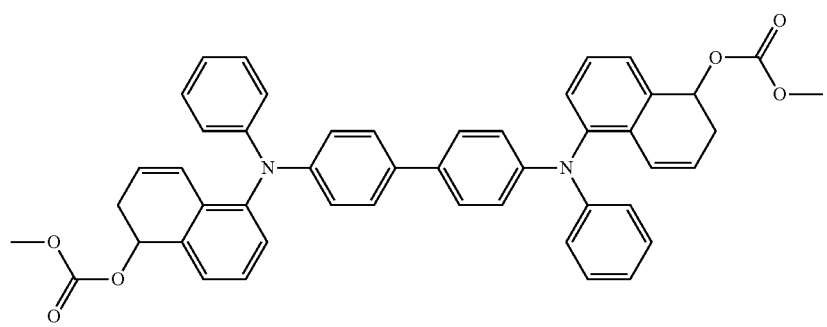
HTL14
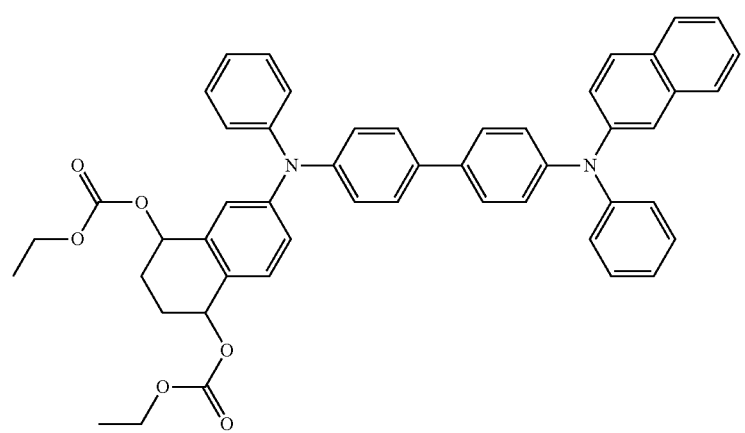 [SMILES: CCOC(=O)OC1CCC(OC(=O)OCC)c2cc(N(c3ccccc3)c3ccc(-c4ccc(N(c5ccccc5)c5ccc6ccccc6c5)cc4)cc3)ccc21]
HTL15
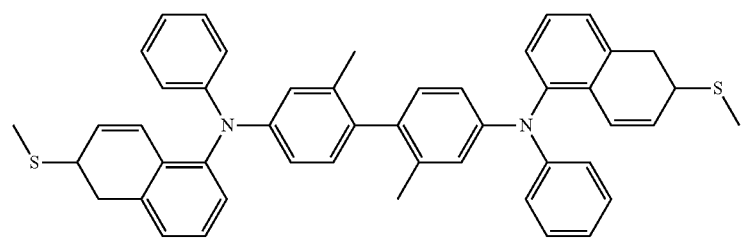
HTL16

TABLE 3-continued
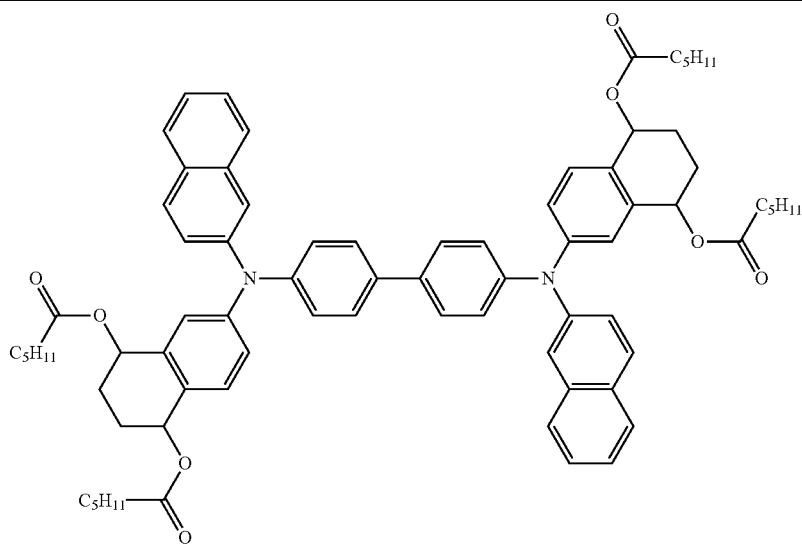
HTL17
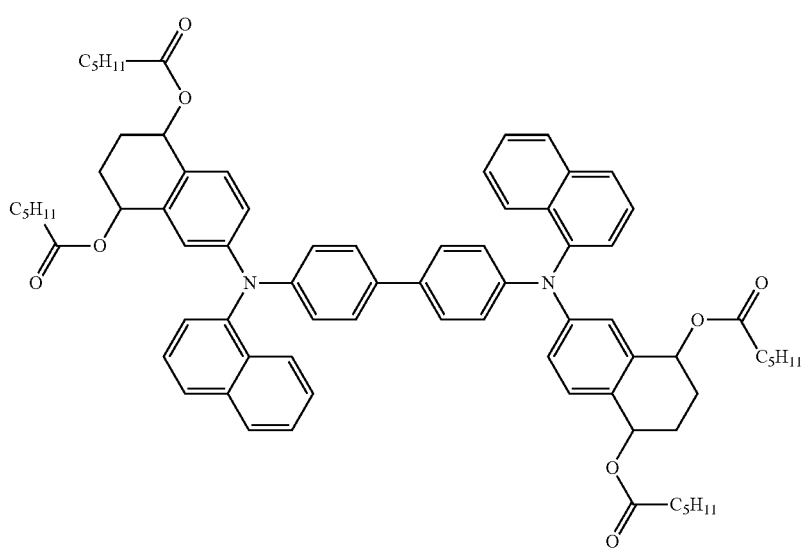
HTL18
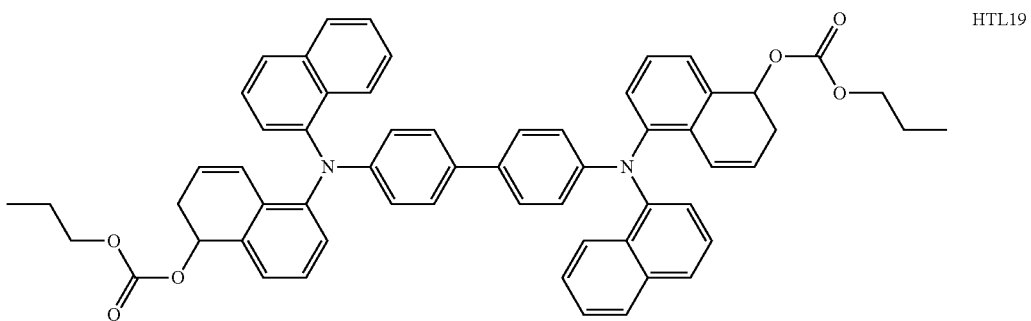
HTL19

TABLE 3-continued
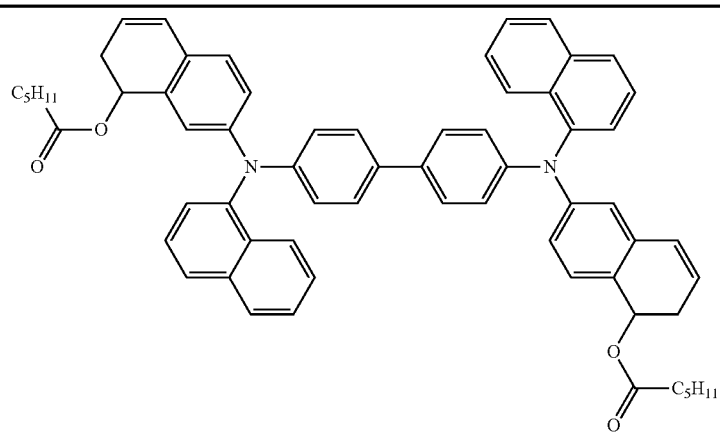
HTL20
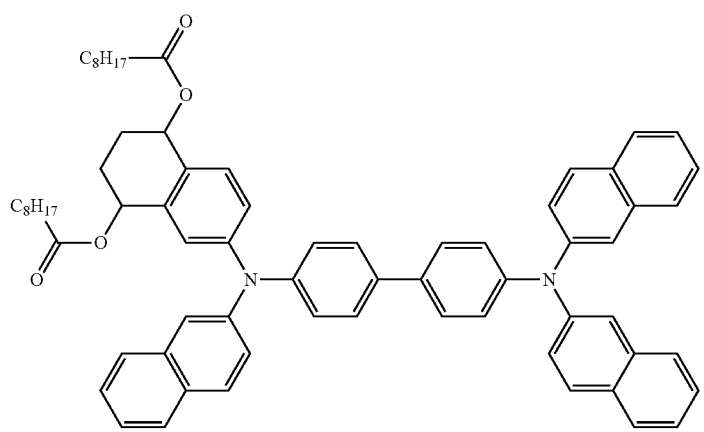
HTL21
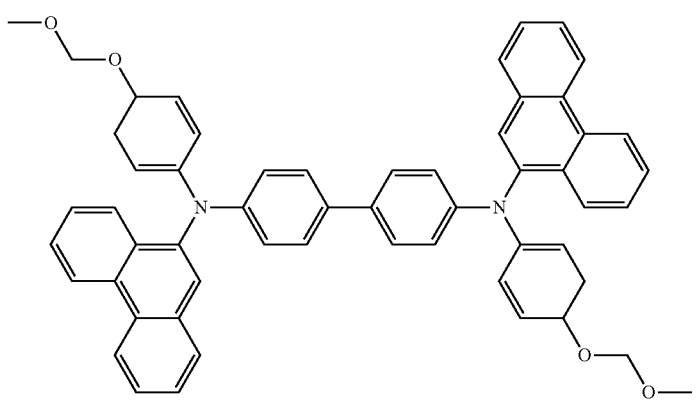
HTL22

TABLE 3-continued
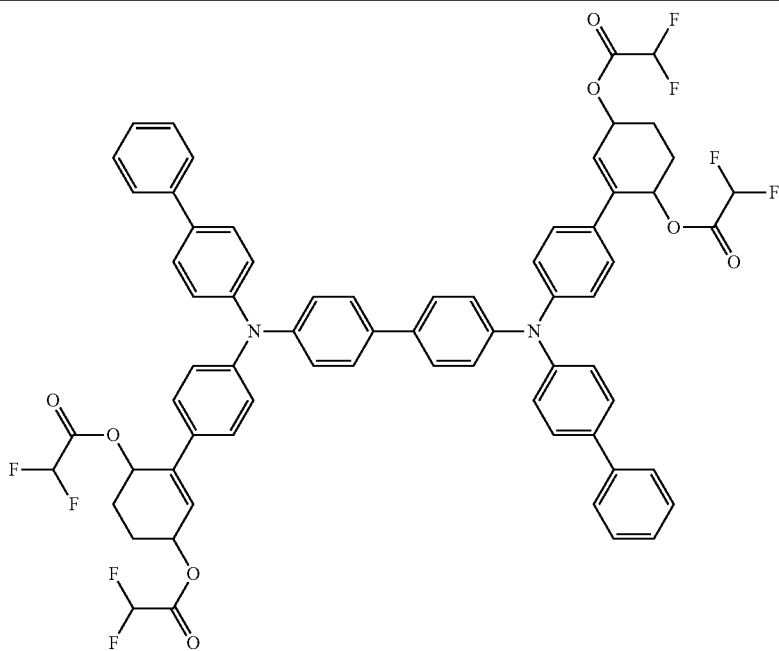
HTL23
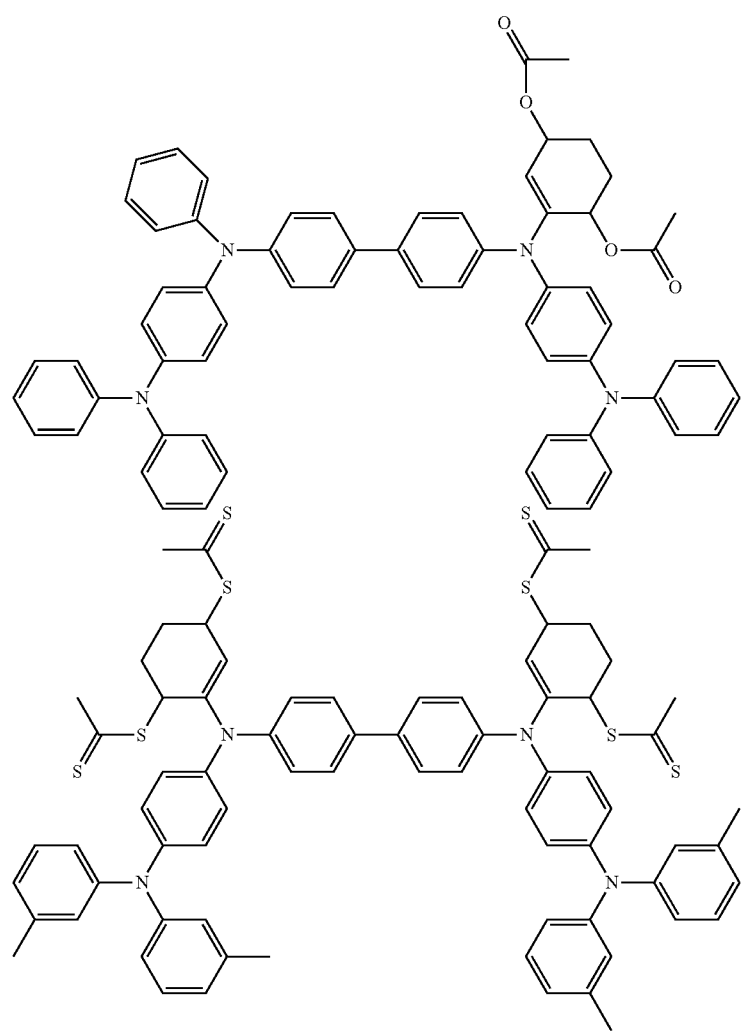
HTL24
HTL25

TABLE 3-continued
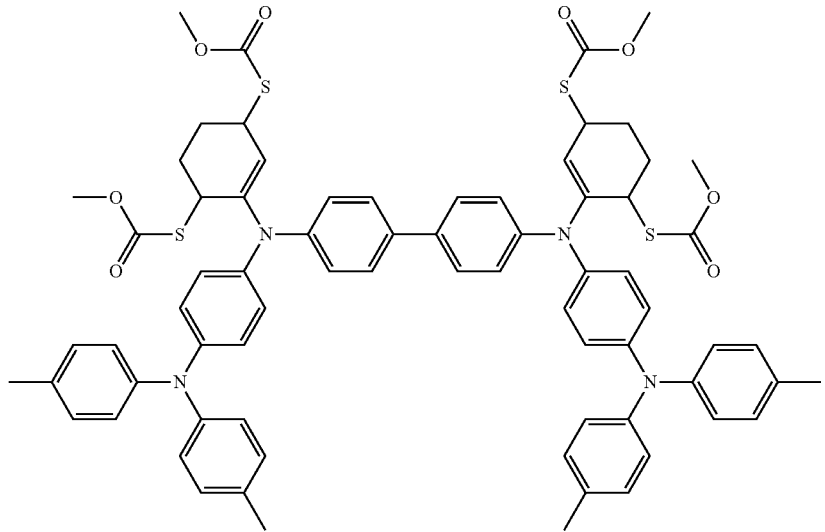
HTL26
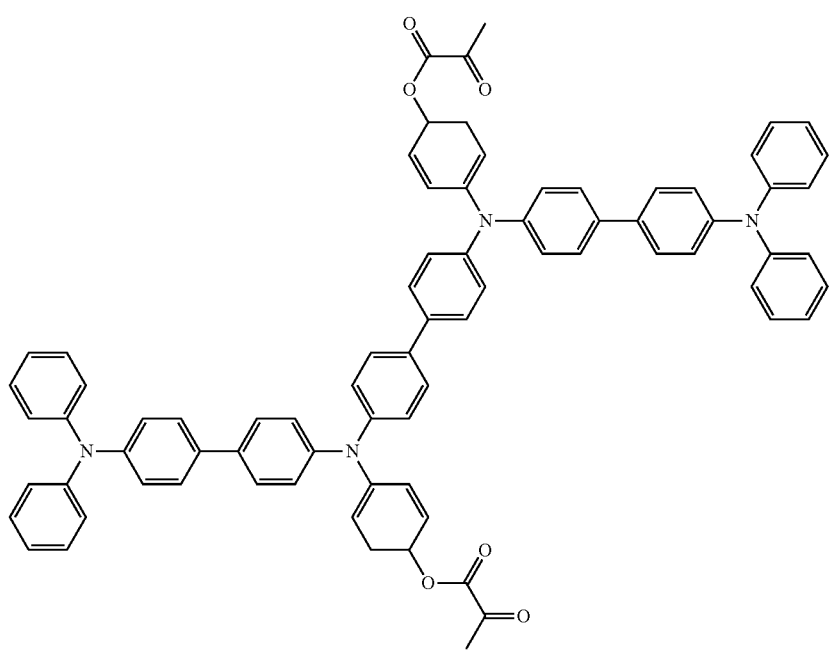 [SMILES: CC(=O)C(=O)OC1C=CC(N(c2ccc(-c3ccc(N(C4=CCC(OC(=O)C(C)=O)C=C4)c4ccc(-c5ccc(N(c6ccccc6)c6ccccc6)cc5)cc4)cc3)cc2)c2ccc(-c3ccc(N(c4ccccc4)c4ccccc4)cc3)cc2)=CC1]
HTL27

TABLE 3-continued
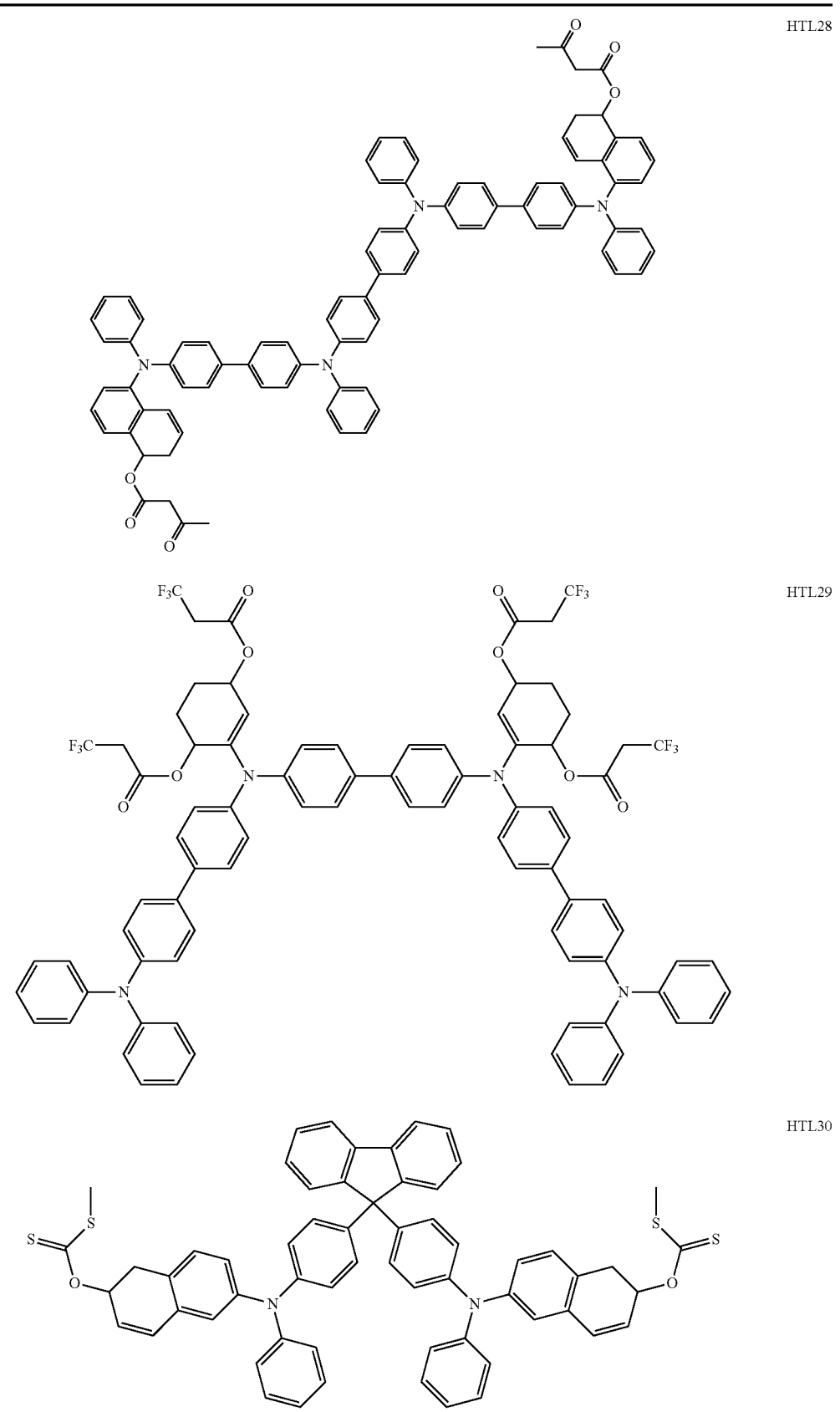
HTL28
HTL29
HTL30

TABLE 3-continued

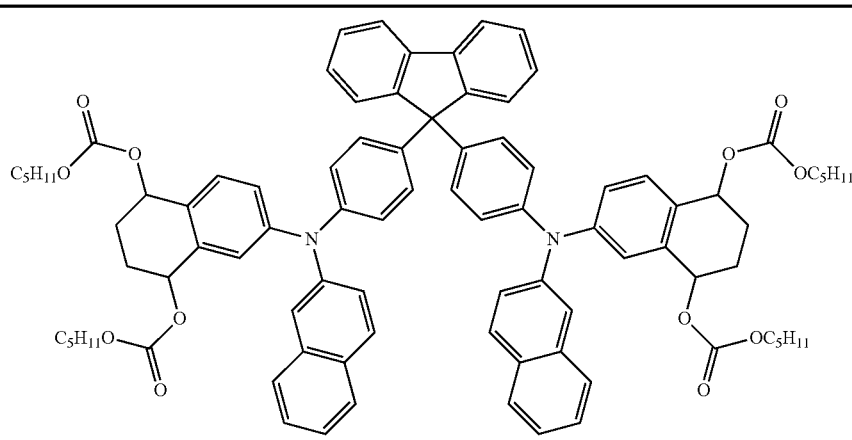

HTL31

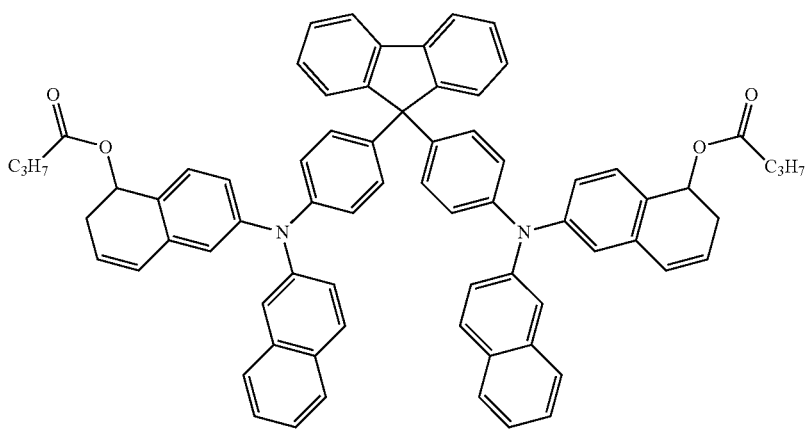

HTL32

Since the above arylamine derivatives have excellent solubility, an ink may be obtained by dissolving the arylamine derivative into variety of solvents. A method for making the ink is described below.

In one embodiment, the solvent is selected from aromatic solvents, halogen solvents and ether solvents. At least one of viscosity control liquid, which is selected from alcohol solvents, ketone solvents, paraffin solvents and alkyl substituted aromatic solvents having at least 4 carbon atoms, is preferably added to the solvent.

The solvent and the viscosity control liquid are explained below.

Examples of the solvent include aromatic solvents such as benzene, toluene, xylene, ethylbenzene, diethylbenzene, anisole, chlorobenzene, dichlorobenzene, chlorotluene, wherein the aromatic solvents may have alkoxy group or halogen.

The examples also include halogenated hydrocarbon solvents such as dichloromethane, dichloroethane, chloroform, carbon tetrachloride, tetrachloroethane and trichloroethane. The examples also include ether solvent such as dibuthyl ether, tetrahydrofuran, and dioxane.

Examples of the viscosity control liquid include linear or branched alcohol solvents such as methanol, ethanol, propanol, butanol, pentanol, hexanol, octanol, nonanol, cyclohexanol, methyl Cellosolve®, ethyl Cellosolve®, ethylene glycol, and benzyl alcohol.

The examples also include alkyl substituted aromatic solvents having at least 4 carbon atoms, which may have linear or branched alkyl group, such as butylbenzene, cyclohexylbenzene, tetralin, and dodecylbenzene.

When the alcohol solvents are used as the viscosity control liquid, the viscosity control liquid may be stored carefully, because it absorbs water easily. Meanwhile, when the alkyl substituted aromatic solvents are used, it is easy to store the viscosity control liquid. In addition, the viscosity may be controlled by changing structure of the alkyl group, when the alkyl substituted aromatic solvents has at least 4 carbon atoms.

However, the alcohol solvents have high viscosity, therefore they are suitable for the viscosity control liquid which is used for film formation process that requires high viscosity such as inkjet method.

Each of the solvent and the viscosity control liquid may be used solely or in combination thereof.

The type or the amount of the viscosity control liquid is suitably selected depending on the viscosity which the film formation process requires.

The alkyl substituted aromatic solvent having at least 4 carbon atoms means the aromatic solvent which has alkyl substituent having at least 4 carbon atoms. The upper limit of the carbon number is not limited but, for example, may be 50.

When the solvent is selected from the aromatic solvents, halogen solvents, and ether solvents, a necessary quantity, for example 1% by mass, of an organic EL element can be dissolved.

When the viscosity control liquid is selected from the alcohol solvents, the ketone solvents, the paraffin solvents, and the alkyl substituted aromatic solvents having at least 4 carbon atoms, a viscosity of a solution comprising the organic EL element is increased and then the viscosity is adjusted depending on a variety of coating methods such as inkjet, nozzle print, and spin coat.

The solvent may be selected from the aromatic solvents, halogen solvents, and ether solvents solely or in combination.

The viscosity control liquid may be selected from the alcohol solvents, the ketone solvents, the paraffin solvents, and the alkyl substituted aromatic solvents having at least 4 carbon atoms solely or in combination.

(Organic EL Element)

The above arylamine compounds are suitable for an organic EL material. The organic EL element which is one example of EL material will be explained below.

The structure of the organic EL element is not particularly limited. FIGS. 1A to 1E are schematic views of preferable embodiments of layer structures which the organic EL elements.

An organic EL element (8) illustrated in FIG. 1A includes a substrate (1); and an anode (2), a luminescent layer (4) and a cathode (7) which are laminated on the substrate (1). Each of the anode (2) and the cathode (7) is connected to one end of a conductive wire, the other end of which is connected to a power source.

Figure 1B:
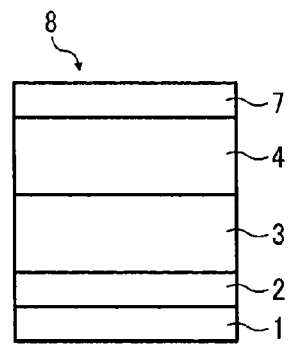

An organic EL element (8) illustrated in FIG. 1B is the same as that of FIG. 1A except that a hole transport layer (3) is provided between an anode (2) and a luminescent layer (4).

Figure 1C:
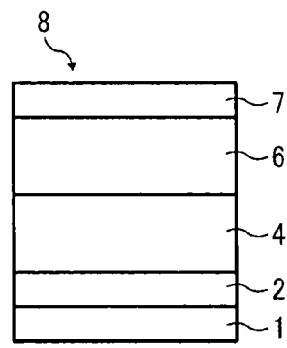

An organic EL element (8) illustrated in FIG. 1C is the same as that of FIG. 1A except that an electron transport layer (6) is provided between a luminescent layer (4) and a cathode (7).

Figure 1D:
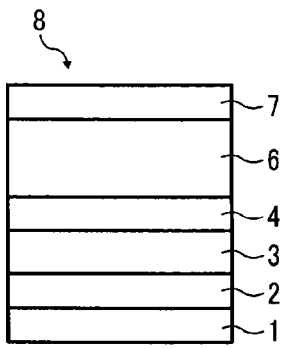

An organic EL element (8) illustrated in FIG. 1D includes a substrate (1); and an anode (2), a hole transport layer (3), a luminescent layer (4), an electron transport layer (6) and a cathode (7) which are laminated on the substrate (1).

Figure 1E:
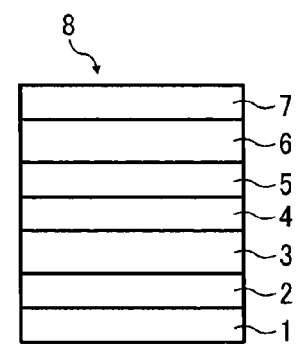

An organic EL element (8) illustrated in FIG. 1E includes a substrate (1); and an anode (2), a hole transport layer (3), a luminescent layer (4), an exciton barrier layer (5), an electron transport layer (6) and a cathode (7) which are laminated on the substrate (1).

The substrate of the organic EL elements illustrated in FIGS. 1A to 1E may be one generally used for organic EL elements. Preferred examples thereof include, but not limited to, glass substrates, silicon substrates and plastic substrates excellent in, for example, surface smoothness and water proofness.

The anode (2) is not particularly limited and may be appropriately selected depending on the intended purpose. The anode has a role of injecting holes to an organic layer such as a hole transport layer and preferably has a high work function. Examples of materials usable for the anode include: metals, alloys and compounds having high work functions such as nickel, gold, platinum, palladium, alloys thereof, tin oxide ($SnO_2$), zinc oxide ($ZnO_2$) containing acceptor impurities, and copper iodide; and electroconductive polymers such as poly(3-methylthiophene) and polypyrroles. The anode (2) may also be formed of a transparent electroconductive material. For example, a transparent electrode formed of indium tin oxide (ITO) is suitably used in consideration of, for example, electroconductivity, light transparency and etching processability. Indium-zinc oxide (IZO: $In_2O_3$-$ZnO$) may also be used. Furthermore, the anode (2) may have a structure where the above transparent electroconductive material deposited on a reflective electrode such as a silver electrode. The film thickness of the anode (2) depends on a type of the material used but is generally 10 nm to 1 µm, preferably 50 nm to 200 nm.

The cathode (7) is not particularly limited and may be appropriately selected depending on the intended purpose. The cathode (7) has a role of injecting electrons to an organic layer and preferably has a low work function. As the cathode (7) is suitably used a magnesium-silver alloy electrode, a magnesium-indium alloy electrode, an aluminum electrode, or a combination of a thin interface layer and an aluminum layer. The film thickness of the cathode (7) depends on a type of the material used but is generally 10 nm to 1 µm, preferably 50 nm to 200 nm.

The organic EL element of one embodiment contains a luminescent organic film, as at least one of the layers between the anode (2) and the cathode (7), which contains the above arylamine compound. It is not limited but the hole transport layer or a hole-injecting layer preferably contains the arylamine compound. The other layer may include the arylamine compound.

A luminescent dyes used as the guest material is not particularly limited and may be appropriately selected depending on the intended purpose. Examples thereof include fluorescent materials and phosphorescent materials.

Examples of the fluorescent materials include perylene derivatives, rubrene derivatives, coumarin derivatives, stilbene derivatives, tristyrylarylene derivatives and distyrylarylene derivatives. Among them, preferred are distyrylarylene derivatives, examples of which include diphenylaminovinylarylene.

As the phosphorescent materials are suitably used iridium complexes, examples of which include $Ir(ppy)_3$ able to emit green light; Btp2Ir(acac) able to emit red light; and Flrpic able to emit blue light.

The hole transport material is not particularly limited and may be appropriately selected depending on the intended purpose from those generally used for organic EL elements. Suitable examples thereof include aromatic amines such as triarylamine derivatives. Specific examples include N,N'-di(1-naphthyl)-N,N'-diphenylbenzidine (α-NPD), 4,4',4"-tris[3-methylphenyl(phenyl)-amino]triphenylamine (m-MTDATA), 4,4',4"-tris[2-naphthyl(phenyl)amino]triphenylamine (2-TNATA), 4,4',4"-tris(carbazol-9-yl)-triphenylamine (TCTA), 2,2',7,7'-tetrakis(N,N-diphenylamino)-9,9'-spirobifluorene (spiro-TAD), and N,N'-diphenyl-p-phenylenediamine (DPPD). These hole transport materials may be used alone or in combination. The above arylamine compounds are also preferably used.

The electron transport material is not particularly limited and may be appropriately selected depending on the intended purpose from those generally used for organic EL elements. Examples thereof include tris(8-hydroxyquinolinato)aluminum(III) (Alq3), oxadiazole derivative (2-(4'-t-butylphenyl)-5-(4"-biphenylyl)-1,3,4-oxadiazole (tBu-PBD) and dimerized or starburst oxadiazole derivatives. These compounds may be used alone or in combination.

In addition to the luminescent layer, the carrier transport layers and the carrier injection layers may be doped with the luminescent dyes. For example, when the hole transport layer is doped with rubrene which is one example of the luminescent dyes, light emission derived from rubrene is observed, so that the resultant element is improved in luminescent efficiency. Also, doping the carrier transport layers and the carrier injection layers with the luminescent dyes can provide advantageous effects such as extension of the service life of the element and improvement in durability of the element.

The organic EL elements schematically illustrated in FIGS. 1A to 1E can be produced by a known production method which is not particularly limited. Examples of the production method suitably usable include a vacuum vapor deposition method (heat vapor deposition method), coating by a spin cast method (spin coating method) and a solvent cast method.

EXAMPLES

Hereinafter, the present invention will be further described with the following Examples, which should not be construed as limiting the scope of the present invention thereto. Example 5, 10, 15, 18, 19, and 20, and Comparative Example 2, 4, and 5, are prophetic.

First, synthetic method of soluble substituents and anthracene intermediates are explained below.

Synthetic Example 1

Synthesis of Intermediate 1

(Synthesis of Compound 1)

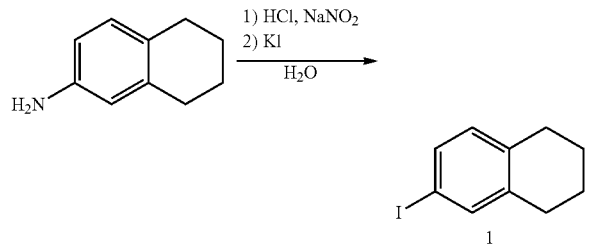

A 500 mL beaker was charged with 1,2,3,4-tetrahydro-6-aminonaphthalene (Product of SIGMA Aldrich Co., g, 65.3 mmol) and 15% HCl (60 mL). While the resultant mixture was being maintained at 5° C. or lower with ice cooling, aqueous sodium nitrite solution (5.41 g, 78.36 mmol water (23 mL)) was added dropwise thereto. After completion of dropwise addition, the mixture was stirred at the same temperature for 1 hour. Then, aqueous potassium iodide solution (13.0 g, 78.36 mmol water (50 mL)) was added to the mixture at one time. The beaker was taken out from the ice bath and the mixture was stirred for 3 hours. Thereafter, the mixture was heated at 60° C. for 1 hour until generation of nitrogen was terminated. After cooled to room temperature, the reaction solution was extracted three times with diethyl ether. The organic layer was washed with 5% aqueous sodium thiosulfate solution (100 mL×3) and further washed with saturated brine (100 mL×2). Moreover, the organic layer was dried with sodium sulfate, followed by filtration. The filtrate was concentrated to obtain red oil.

The obtained red oil was purified through silica gel chromatography (solvent: hexane) to obtain a clear solid as the compound 1 (yield amount: 12.0 g, yield rate: 71.2%).

The analysis results of Compound 1 are shown below.

$^1$H NMR (500 MHz, CDCl$_3$, TMS, δ): 1.73-1.81 (m, 4H), 2.70 (quint, 4H, J=4.85 Hz), 6.80 (d, 1H, J=8.0 Hz), 7.38 (dd, 1H, J$_1$=8.0 Hz J$_2$=1.75 Hz), 7.41 (s, 1H)

Mass spectrometry: GC-MS m/z=258 (M+) (actual measured value); 258.099 (theoretical value of molecular weight)

(Synthesis of Compound 2)

Compound 2 was synthesized applying the method described in J. Org. Chem. 1999, 64, 9365-9373.

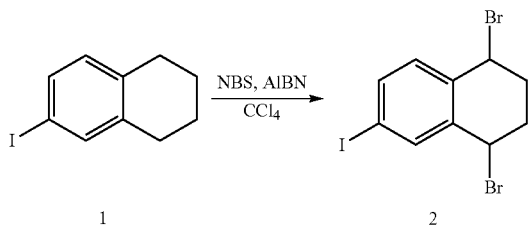

A 100 mL round-bottom flask was charged with compound 1 (3.1 g, 12 mmol), azobisisobutylonitrile (59 mg, 0.36 mmol), carbon tetrachloride (50 mL) and N-bromosuccinimide (4.7 g, 26.4 mmol). After the flask had been purged with argon gas, the mixture was gently heated to 80° C., stirred for 1 hour at the same temperature and then cooled to room temperature.

The precipitates were removed through filtration. The filtrate was concentrated under reduce pressure to obtain a pale yellow solid as compound 2 (yield amount: 4.99 g, yield rate: 100%).

The compound was used for a next reaction without additional purification.

The analysis results of Compound 2 are shown below.

$^1$H NMR (500 MHz, CDCl$_3$, TMS, δ): 2.31-2.41 (m, 2H), 2.70-2.79 (m, 2H), 5.65 (t, 2H, J=2.0 Hz), 7.24-7.28 (m, 2H), 7.31-7.34 (m, 2H)

Mass spectrometry: GC-MS m/z=416 (100.0%), 414 (51.4%), 418 (48.6%) (actual measured value); 415.891 (theoretical value of molecular weight)

(Synthesis of Compound 3)

1,2,3,4-tetrahydro-5-iodonaphthalene was obtained in the similar manner as in preparation of compound 1, provided that 1,2,3,4-tetrahydro-5-aminonaphthalene was used instead of 1,2,3,4-tetrahydro-6-aminonaphthalene.

Compound 3 was obtained in the similar manner as in preparation of compound 2, provided that 1,2,3,4-tetrahydro-5-iodonaphthalene was used instead of compound 1.

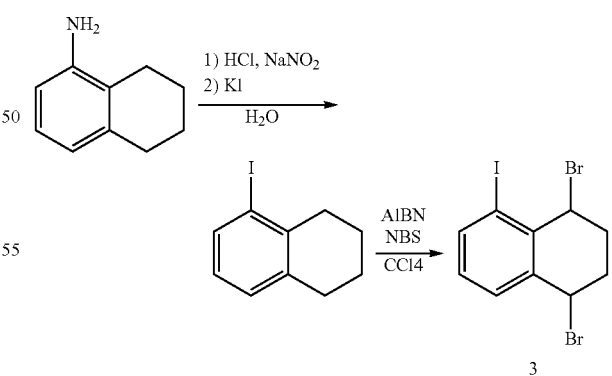

$^1$H NMR (500 MHz, CDCl$_3$, TMS, δ): 2.72-2.76 (m, 2H), 2.81-2.85 (m, 2H), 5.53-5.54 (m, H), 5.60-5.62 (m, H), 6.95-6.99 (m, H), 7.35 (d, H, J=7.8 Hz), 7.83 (d, H, J=7.8 Hz)

Mass spectrometry: GC-MS m/z=416 (100.0%), 414 (51.4%), 418 (48.6%) (actual measured value); 415.891 (theoretical value of molecular weight)

It was confirmed that the synthesized compound is corresponding to compound 3 from the results of the analysis.

(Synthesis of Compound 4)

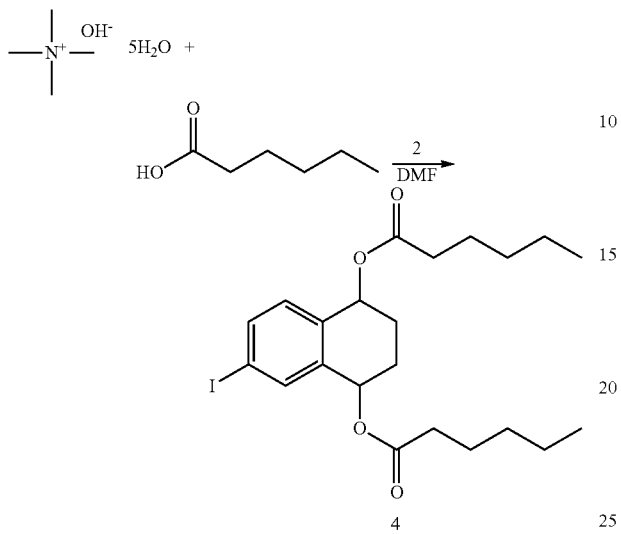

A 100 mL round-bottom flask was charged with tetramethylammonium hydroxide pentahydrate (3.62 g, 20 mmol), hexanoic acid (2.51 mL, 20 mmol), N,N-dimethylformamide (hereinafter referred to as "DMF", 30 mL). After the flask had been purged with argon gas, the mixture was stirred for 2.5 hours at ambient temperature. Then, compound 2 (4.16 g, 10 mmol) was added thereto. Then, the mixture was stirred for 16 hours at ambient temperature. Then the reaction solution was diluted with ethyl acetate (100 mL), and added purified water (200 mL), to isolate an organic phase. A water phase was extracted four times with ethyl acetate (30 mL). Then, the extract was mixed with the organic phase. The mixture was washed with saturated sodium hydrogen carbonate solution and further washed with saturated brine and then dried with magnesium sulfate. The filtrate was concentrated to obtain an orange-colored oil. The obtained oil was purified through silica gel chromatography (solvent: toluene to ethylene acetate/toluene (5/95, v/v)) to obtain compound 4 as a clear oil (yield amount: 2.44 g, yield rate: 50.2%).

The analysis results of Compound 4 are shown below.

$^1$H NMR (500 MHz, CDCl$_3$, TMS, δ): 0.87-0.90 (m, 6H), 1.24-1.34 (m, 8H), 1.60-1.67 (m, 4H), 1.90-1.94 (m, 2H), 2.23-2.34 (m, 6H), 5.98 (d, 2H, J=3.5 Hz), 7.06 (d, 2H, J=8.0 Hz), 7.63-7.66 (m, 2H)

Mass spectrometry: GC-MS m/z=486 (M+) (actual measured value); 486.384 (theoretical value of molecular weight)

It was confirmed that the synthesized compound is corresponding to compound 4 from the results of the analysis.

(Synthesis of Compound 5)

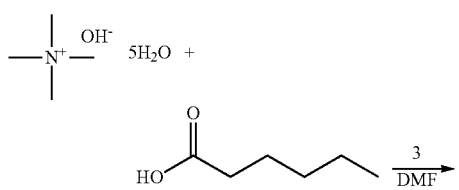

A 100 mL round-bottom flask was charged with tetramethylammonium hydroxide pentahydrate (6.8 g, 37.5 mmol), hexanoic acid (4.7 mL, 37.5 mmol), N,N-dimethylformamide (hereinafter referred to as "DMF", 60 mL). After the flask had been purged with argon gas, the mixture was stirred for 2.5 hours at ambient temperature. Then, compound 3 (6.24 g, 15 mmol) was added thereto. Then, the mixture was stirred for 16 hours at ambient temperature. Then the reaction solution was diluted with ethyl acetate (100 mL), and added purified water (200 mL), to isolate an organic phase. A water phase was extracted four times with ethyl acetate (30 mL). Then, the extract was mixed with the organic phase. The mixture was washed with saturated sodium hydrogen carbonate solution and further washed with saturated brine and then dried with magnesium sulfate. The filtrate was concentrated to obtain an orange-colored oil. The obtained oil was purified through silica gel chromatography (solvent: toluene to ethylene acetate/toluene (5/95, v/v)) to obtain compound 5 as a clear oil (yield amount: 2.00 g, yield rate: 27.0%).

The analysis results of Compound 5 are shown below.

$^1$H NMR (500 MHz, CDCl$_3$, TMS, δ): 0.86-0.89 (m, 6H), 1.25-1.35 (m, 8H), 1.58-1.62 (m, 4H), 1.63-1.69 (m, 2H), 1.94-1.96 (m, 2H), 2.24-2.38 (m, 4H), 5.89 (t, H, J=2.9 Hz), 6.00 (t, H, J=2.9 Hz), 7.04-7.07 (m, H), 7.36 (d, H, J=8.0 Hz), 7.89 (d, H, J=8.0 Hz)

Mass spectrometry: GC-MS m/z=486 (M+) (actual measured value); 486.384 (theoretical value of molecular weight)

It was confirmed that the synthesized compound is corresponding to compound 5 from the results of the analysis.

Synthetic Example 2

Synthesis of Intermediate 2

(Synthesis of Compound 6)

According to the following reaction formula (scheme), Compound 6 was synthesized.

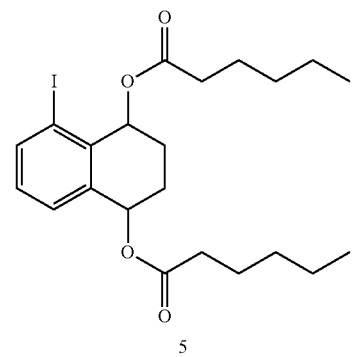

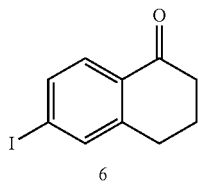

The above 6-amino-3,4-dihydro-1(2H)—naphthalenone as a raw material was purchased from SIGMA Aldrich Co. and subjected to no treatments before use.

A 500 mL beaker was charged with 6-amino-3,4-dihydro-1(2H)-naphthalenone (20 g, 119.0 mmol) and 15% HCl (96 mL). While the resultant mixture was being maintained at 5° C. or lower with ice cooling, aqueous sodium nitrite solution (9.9 g, 143.0 mmol water (42 mL)) was added dropwise thereto. After completion of dropwise addition, the mixture was stirred at the same temperature for 30 min. Then, aqueous potassium iodide solution (23.7 g, 143.0 mmol water (77 mL)) was added to the mixture at one time. The beaker was taken out from the ice bath and the mixture was stirred for 2.5 hours. Thereafter, the mixture was heated at 60° C. for 0.5 hours until generation of nitrogen was terminated. After cooled to room temperature, the reaction solution was extracted three times with diethyl ether. The organic layer was washed with 5% aqueous sodium thiosulfate solution (100 mL×3) and further washed with saturated brine (100 mL×2). Moreover, the organic layer was dried with sodium sulfate, followed by filtration. The filtrate was concentrated to obtain red oil.

The obtained red oil was purified through silica gel chromatography (solvent: ethyl acetate/hexane=9/1) to obtain a pale orange solid. Further, the obtained solid was recrystallized from 2-propanol to obtain Compound 6 as pale orange crystals (yield amount: 11.4 g, yield rate: 35.2%).

The analysis results of Compound 6 are shown below.

$^1$H NMR (500 MHz, CDCl$_3$, TMS, δ): 2.13 (quint, 2H, J=5.7 Hz), 2.64 (t, 2H, J=6.3 Hz), 2.92 (t, 2H, J=6.0 Hz), 7.66 (d, 1H, J=8.0 Hz), 7.67 (s, 1H), 7.72 (d, 1H, J=8.0 Hz)

Melting point: 74.0° C.-75.0° C.

Mass spectrometry: GC-MS m/z=272 (M) (actual measured value); 272.082 (theoretical value of molecular weight)

It was confirmed that the synthesized compound is corresponding to compound 6 from the results of the analysis.

(Synthesis of Compound 7)

According to the following reaction formula (scheme), Compound 7 was synthesized.

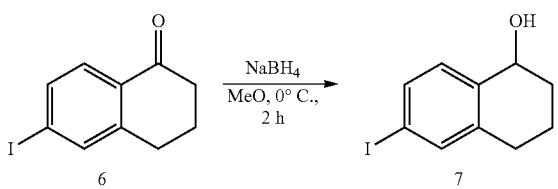 [SMILES: O=C1CCCc2cc(I)ccc21 ; "MeO, 0° C.,2 h" ; "NaBH4" ; OC1CCCc2cc(I)ccc21]

A 200 mL round-bottom flask was charged with Compound 6 (4.1 g, 15 mmol) and methanol (100 mL). Sodium borohydride (850 mg, 22.5 mmol) was gradually added to the resultant mixture at 0° C. with ice cooling, followed by stirring for 3 hours at 0° C. Subsequently, excessive sodium borohydride was neutralized with dilute hydrochloric acid, and saturated brine was added to the mixture, which was then extracted with ethyl acetate (50 mL) 5 times. The extraction liquid was washed with ammonium chloride (100 mL) once and with brine (100 mL) twice. Thereafter, sodium sulfate was added thereto, followed by filtration. The filtrate was concentrated to obtain Compound 7 as a pale red solid (yield amount: 3.93 g, yield rate: 95.5%), which was directly used in the next step without any further purification.

The analysis results of Compound 7 are shown below.

$^1$H NMR (500 MHz, CDCl$_3$, TMS, δ): 1.71 (d, 1H, J=5.8 Hz), 1.84-2.02 (m, 4H), 2.65-2.71 (m, 1H), 2.75-2.81 (m, 1H), 4.72 (d, 1H, J=4.6 Hz), 7.17 (d, 1H, J=8.0 Hz), 7.47 (s, 1H), 7.52 (d, t 1H, J$_1$=8.0 Hz, J$_2$=1.2 Hz)

Mass spectrometry: GC-MS m/z=274 (M) (actual measured value); 274.098 (theoretical value of molecular weight)

Melting point: 82.0° C.-84.0° C.

It was confirmed that the synthesized compound is corresponding to compound 7 from the results of the analysis.

(Synthesis of Compound 8)

According to the following reaction formula (scheme), Compound 8 was synthesized.

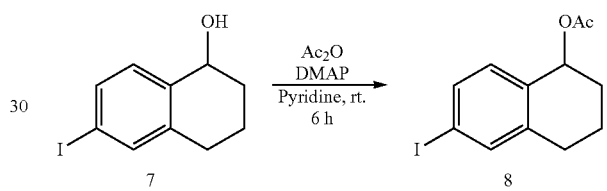

A 50 mL round-bottom flask was charged with Compound 7 (3.70 g, 13.5 mmol) and N,N-dimethylaminopyridine (hereinafter referred to as "DMAP", 10 mg). After the flask had been purged with argon gas, anhydrous pyridine (8.1 mL) and acetic anhydride (6.2 mL) were added thereto, followed by stirring at room temperature for 6 hours. Water (50 mL) was added to the reaction solution, which was then extracted with ethyl acetate (20 mL) five times. The combined organic layer was washed with dilute hydrochloric acid (100 mL) three times, then with sodium hydrogen carbonate solution (100 mL) twice and finally with saturated brine (100 mL) twice. The mixture was dried with magnesium sulfate, followed by filtration. The filtrate was concentrated to obtain Compound 8 as a brown liquid (yield amount: 4.28 g, yield rate: 100%), which was directly used in the next step without any further purification.

The analysis results of Compound 8 are shown below.

$^1$H NMR (500 MHz, CDCl$_3$, TMS, δ): 1.76-1.83 (m, 1H), 1.89-2.10 (m, 1H), 2.07 (s, 3H), 2.67-2.73 (m, 1H), 2.79-2.84 (m, 1H), 5.93 (t, 1H, J=5.2 Hz), 7.01 (d, 1H, J=8.6 Hz), 7.49 (d, 1H, J=2.3 Hz), 7.52 (s, 1H)

Mass spectrometry: GC-MS m/z=316 (M) (actual measured value); 316.135 (theoretical value of molecular weight)

It was confirmed that the synthesized compound is corresponding to compound 8 from the results of the analysis.

(Synthesis of Compound 9)

According to the following reaction formula (scheme), Compound 9 was synthesized.

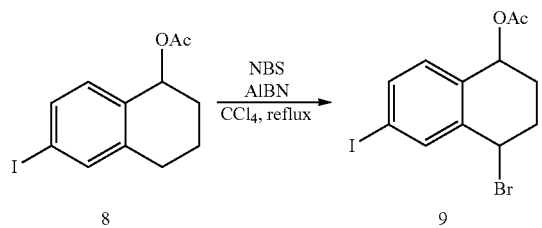

A 100 mL round-bottom flask was charged with Compound 8 (4.27 g, 13.5 mmol), azobisisobutylonitrile (hereinafter referred to as "AIBN", mg), carbon tetrachloride (100 mL) and N-bromosuccinimide (hereinafter referred to as "NBS", 2.64 g, 14.8 mmol). After the flask had been purged with argon gas, the mixture was gently heated to 80° C., stirred for 1 hour at the same temperature and then cooled to room temperature.

The precipitates were removed through filtration. The filtrate was concentrated under reduce pressure to obtain a pale yellow solid, which was purified through silica gel chromatography (solvent: ethyl acetate/hexane=8/2) to obtain Compound 9 as pale red oil (yield amount: 4.9 g, yield rate: 92.0%). Compound 9 was obtained as a 10:7 mixture of cis form and trans form.

The analysis results of Compound 9 are shown below.

Precise mass spectrometry: LC-MS m/z=393.9028 (100.0%), 395.9082 (actual measured value); 393.9065 (100.0%), 395.9045 (97.3%) (theoretical value of molecular weight)

It was confirmed that the synthesized compound is corresponding to compound 9 from the results of the analysis.

(Synthesis of Compound 10)

According to the following reaction formula (scheme), Compound was synthesized.

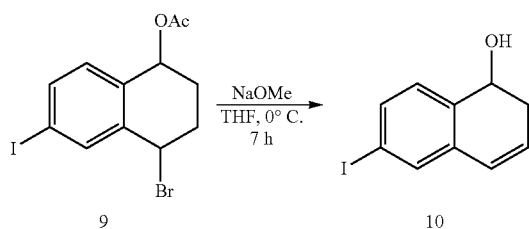 [SMILES: CC(=O)OC1CCC(Br)c2cc(I)ccc21 ; "THF, 0° C.7 h" ; OC1CC=Cc2cc(I)ccc21 ; "NaOMe"]

A 500 mL round-bottom flask was charged with Compound 9 (4.2 g, 10.6 mmol) and then purged with argon gas, followed by addition of THF (300 mL). Subsequently, sodium methoxide-methanol solution (25% by mass, 24 mL) was added to the resultant mixture at 0° C. with ice cooling, followed by stirring at the same temperature for 6 hours. Water (300 mL) was added to the mixture, which was extracted with ethyl acetate (100 mL) four times. The extraction liquid was washed with saturated brine (100 mL) twice and dried with sodium sulfate, followed by filtration. The filtrate was concentrated to obtain a brown liquid. The obtained brown liquid was purified using a column to obtain Compound 10 as colorless crystals (yield amount: 1.2 g, yield rate: 41.0%).

The analysis results of Compound 10 are shown below.

$^1$H NMR (500 MHz, CDCl$_3$, TMS, δ): 1.70 (d, 1H, J=3.4 Hz), 2.58-2.61 (m, 2H), 4.76 (q, 1H, J=6.3 Hz), 6.04 (q, 1H, J=5.2 Hz), 6.47 (d, 1H, J=9.8 Hz), 7.13 (d, 1H, J=8.1 Hz), 7.47 (d, 1H, J=1.7 Hz), 7.57 (J$_1$=8.1 Hz J$_2$=1.7 Hz)

Mass spectrometry: GC-MS m/z=272 (M+), 254 (M+−H$_2$O) (actual measured value); 272.082 (theoretical value of molecular weight)

It was confirmed that the synthesized compound is corresponding to compound 10 from the results of the analysis.

(Synthesis of Compound 11-1)

According to the following reaction formula (scheme), Compound 11 was synthesized.

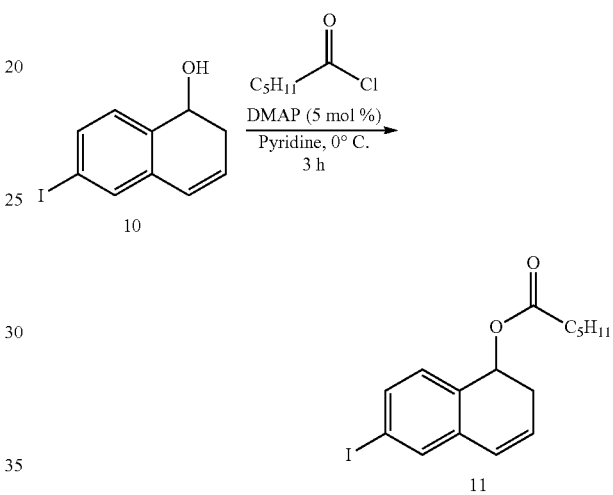

A 50 mL round-bottom flask was charged with Compound 10 (680 mg, 2.5 mmol) and DMAP (15.3 mg, 0.125 mmol), and purged with argon gas, followed by addition of pyridine (15 mL). Subsequently, hexanoylchloride (370 mg, 2.75 mmol) was added dropwise to the resultant mixture at 0° C. with ice cooling, and stirred at the same temperature for 3 hours. Water was added to the reaction solution, which was extracted with ethyl acetate (50 mL) three times. The organic layer was washed sequentially with saturated sodium hydrogen carbonate solution, and then washed with saturated brine, and dried with magnesium sulfate, followed by filtration. The filtrate was concentrated to obtain a brown liquid. The obtained liquid was dissolved in ethyl acetate/hexane (95/5), and the resultant solution was caused to pass through a silica gel pad having a thickness of 3 cm. The filtrate was concentrated to obtain Compound 11 as a colorless liquid (yield amount: 560 g, yield rate: 60.5%).

The analysis results of Compound 11 are shown below.

$^1$H NMR (500 MHz, CDCl$_3$, TMS, δ): 0.86 (t, 3H, J=7.2 Hz), 1.21-1.30 (m, 4H), 1.54-1.60 (m, 2H), 2.23 (td, 2H, J$_1$□7.5 Hz J$_2$=2.3 Hz), 2.58-2.62 (m, 2H), 5.95 (t, 1H, J=5.2 Hz), 6.03 (quint, 1H, J=4.6 Hz), 6.48 (d, 1H, J=9.8 Hz), 7.10 (d, 1H, J=8.0 Hz), 7.48 (d, 1H, J=1.7 Hz), 7.54 (dd, 1H, J$_1$=8.0 Hz, J$_2$=1.8 Hz)

Mass spectrometry: GC-MS m/z=370 (M), 254 (M+−C$_5$H$_{11}$COOH) (thermally decomposed product) 370.225 (theoretical value of molecular weight)

It was confirmed that the synthesized compound is corresponding to compound 11 from the results of the analysis.
(Synthesis of Compound 12)

According to the following reaction formula (scheme), Compound 12 was synthesized.

1-cyclohexenyl trifluoromethanesulfonate as a raw material was purchased from SIGMA Aldrich Co. and subjected to dibromination similarly to synthesis of compound 2. The obtained 3,6-dibromo-1-cyclohexenyl trifluoromethanesulfonate was used for next reaction without purification.

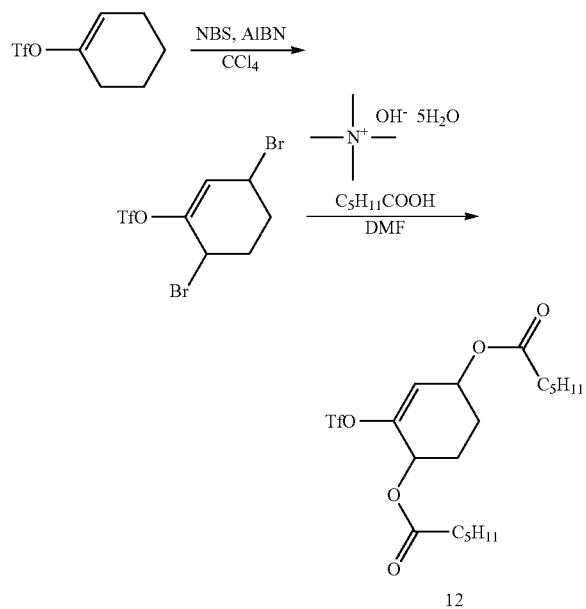

A 100 mL round-bottom flask was charged with tetramethylammonium hydroxide pentahydrate (1.81 g, 10 mmol), hexanoic acid (1.25 mg, 10 mmol), N,N-dimethylformamide (hereinafter referred to as "DMF", 30 mL). After the flask had been purged with argon gas, the mixture was stirred for 2.5 hours at ambient temperature. Then, 3,6-dibromo-1-cyclohexenyl trifluoromethanesulfonate (1.8 g, 4.5 mmol) was added thereto. Then, the mixture was stirred for 16 hours at ambient temperature. Then the reaction solution was diluted with ethyl acetate (100 mL), and added purified water (200 mL), to isolate an organic phase. A water phase was extracted four times with ethyl acetate (30 mL). Then, the extract was mixed with the organic phase. The mixture was washed with saturated sodium hydrogen carbonate solution and further washed with saturated brine and then dried with magnesium sulfate. The filtrate was concentrated to obtain an orange-colored oil. The obtained oil was purified through silica gel chromatography (solvent: hexane to ethylene acetate/toluene (5/95, v/v)) to obtain compound 12 as a clear oil (yield amount: 900 mg, yield rate: 43.2%).

The analysis results of Compound 12 are shown below.

$^1$H NMR (500 MHz, CDCl$_3$, TMS, δ): 0.90 (t, J=7.5 Hz, 6H), 1.26-1.37 (m, 8H), 1.60-1.67 (m, 4H), 1.76-1.92 (m, 2H), 1.96-2.08 (m, 2H), 2.29-2.36 (m, 4H), 5.48 (q, 1H, J=4.6 Hz), 5.51 (t, 1H, J=4.6 Hz), 6.12 (d, J=5.2 Hz, 1H)

Precise mass spectrometry: LC-TofMS m/z=458.1507 (actual measured value); 225.9980 (M+–2C$_5$H$_{11}$COOH); 458.1586, 225.9910 (theoretical value of molecular weight)

It was confirmed that the synthesized compound is corresponding to compound 12 from the results of the analysis.

(Synthesis of Compound 13)

According to the following reaction formula (scheme), Compound 13 was synthesized.

Known 1,5-cyclohexadienyl trifluoromethanesulfonate was subjected to dibromination similarly to synthesis of compound 12 to obtain 4-bromo-1,5-cyclohexadienyl trifluoromethanesulfonate.

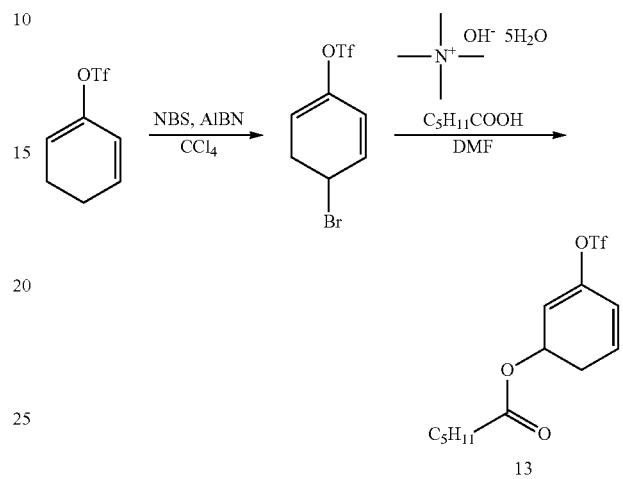

The bromine atom of 4-bromo-1,5-cyclohexadienyl trifluoromethanesulfonate was esterified similarly to compound 12, to obtain compound 13 as a clear oil. (yield amount: 800 mg, yield rate: 30%).

The analysis results of Compound 13 are shown below.

Precise mass spectrometry: Tof-MS m/z=342.0766 (M+), 225.9982 (M+–C$_5$H$_{11}$COOH) (actual measured value); 342.0749 (M+), 225.9911 (M+–C$_5$H$_{11}$COOH) (theoretical value of molecular weight)

It was confirmed that the synthesized compound is corresponding to compound 13 from the results of the analysis.

(Synthesis of Compound 14)

According to the following reaction formula (scheme), Compound 14 was synthesized.

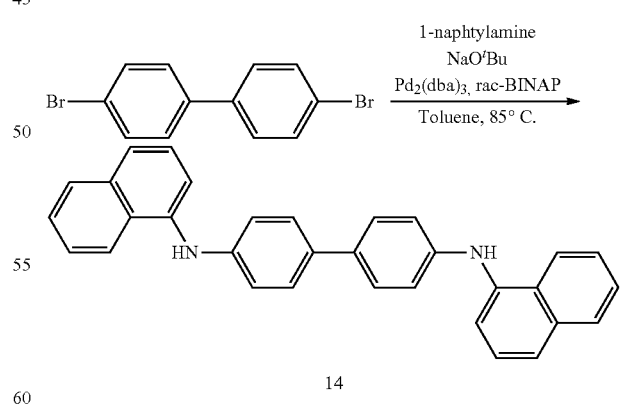

A round-bottom flask was charged with 4,4'-dibromo biphenyl (7.8 g, 25 mmol), 1-naphthyl amine (8.59 g, 60 mmol), sodium tert-butoxide (5.77 g, 60 mmol). After the flask had been purged with argon gas, toluene was (150 mL) added. Also, racemic-BINAP (1.4 g, 2.25 mmol), palladium acetate (334 mg, 1.5 mmol) was added thereto. Then, the mixture was stirred for 16 hours at 85° C. The reaction was terminated by adding water, and then the precipitated solid was filtrated. The solid was washed with water and further methanol and then dried under vacuum. The solid was purified through silica gel chromatography (solvent: toluene) to obtain compound 14 as a pale blistered crystal (yield amount: 3.6 g, yield rate: 33%).

The analysis results of NMR and mass spectrometry of Compound 14 corresponded to data described in a given literature.

(Synthesis of Compound 15)

According to known method described in following reaction formula (scheme), compound 15 was synthesized from 4,4'-Bis(carbazol-9-yl)biphenyl as raw material, which was purchased from Wako Pure Chemical Industries, Ltd. N-bromosuccinimide was added into DMF solution for bromination, then bromine was induced to boronic acid ester in accordance with the method of Ishiyama and Miyaura, et al witch is described in J. Org. Chem. 1995, 60, 7508-7510.

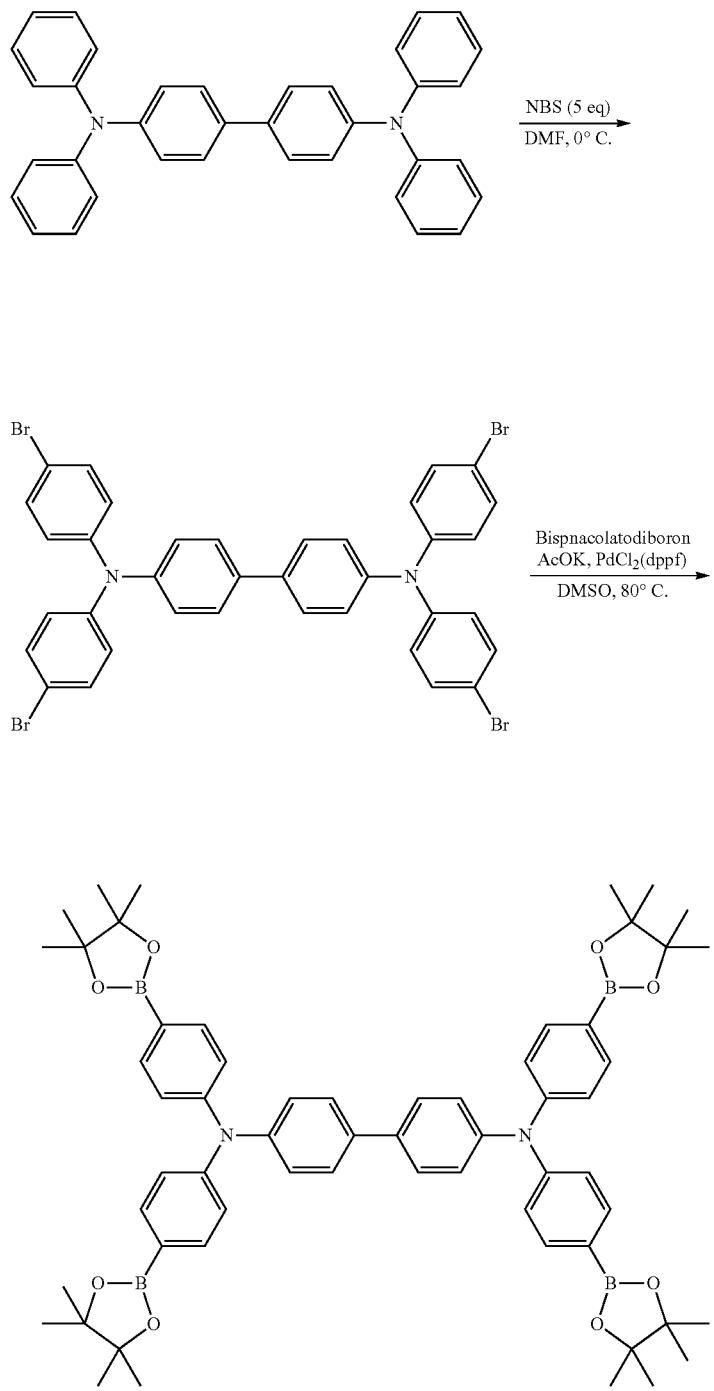

81
(Synthesis of Compound 16)
According to the method similarly to compound 14, compound 16 was synthesized (yield amount: 4.0 g, yield rate: 70%).
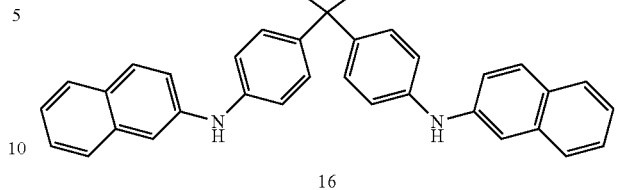
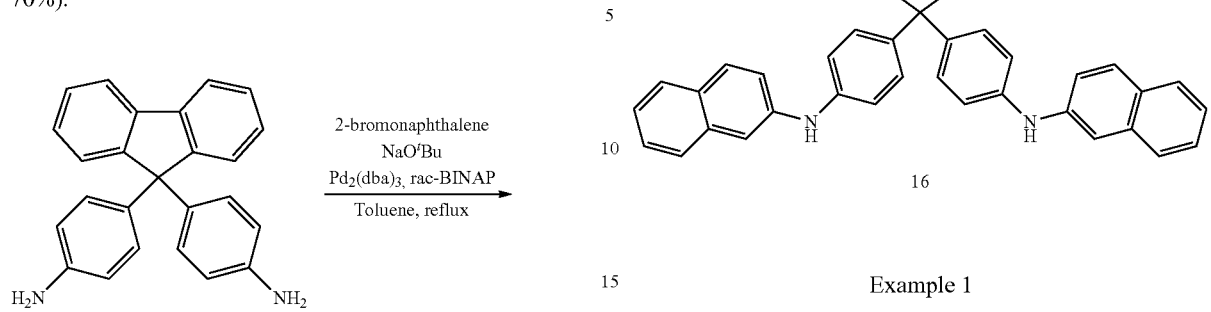
Example 1
Synthesis of Arylamine Compound HTL17
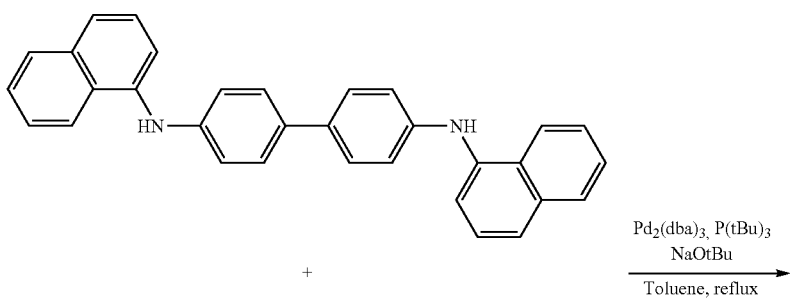
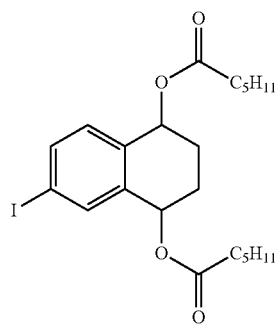
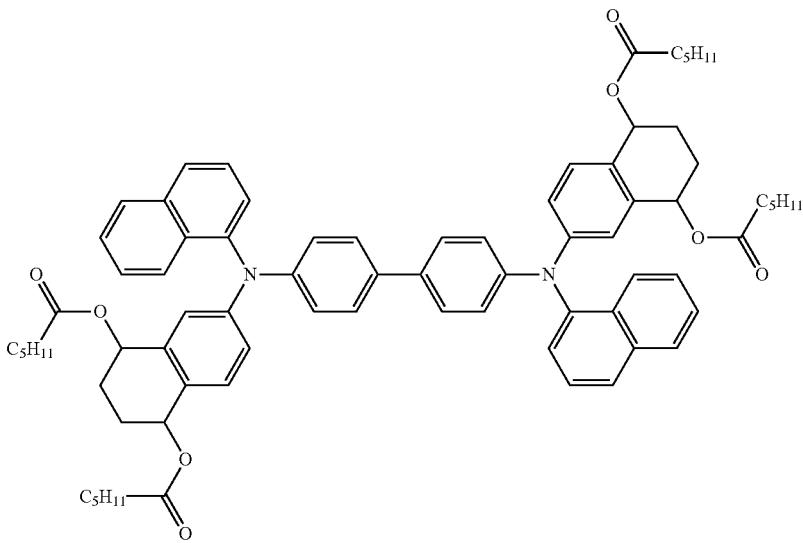
HTL17

A round-bottom flask was charged with N,N'-di(1-naphthyl)-4,4'-benzidine (compound 14) (2.4 g, 5.5 mmol), compound 4 (6.4 g, 13.2 mmol), sodium tert-butoxide (1.37 g, 14.3 mmol), tris(dibenzylideneacetone)dipalladium (50.3 mg, 0.055 mmol), tri-tert-butylphosphine (22.2 mg, 0.11 mmol). After the flask had been purged with argon gas, toluene (100 mL) was added. Then, the mixture was stirred for 16 hours at 110° C. After the flask was cooled to ambient temperature, the reaction was terminated by adding water. Ethyl acetate and water were added to the reaction solution to isolate an organic phase. A water phase was extracted three times with ethyl acetate. Then, the extract was mixed with the organic phase. The mixture was washed with water and further washed with brine, followed by dried with magnesium sulfate. After removing the drying agent by filtration, the filtrate was concentrated and purified through silica gel chromatography (solvent: toluene), followed by washing with methanol to obtain HTL17 as pale yellow solid (yield amount: 1.7 g, yield rate: 26.8%).

$^1$H NMR (500 MHz, CDCl$_3$, TMS, δ): 0.802-0.904 (m, 12H), 1.15-1.32 (m, 12H), 1.42-1.48 (m, 4H), 1.58-1.65 (m, 8H), 1.87-1.91 (m, 4H), 2.03-2.35 (m, 12H), 6.21-6.27 (m, 2H), 6.63 (t, 2H, J=9.2 Hz), 7.24-7.25 (m, 2H), 7.29-7.36 (m, 4H), 7.44 (td, 1H, J$_1$=5.3 Hz, J$_2$=2.3 Hz), 7.57-7.75 (m, 6H)

Precise mass spectrometry (MALDI-TOFMS): m/z=1153.4882 (M+), 689.8550 (M+−4C$_5$H$_{11}$COOH) (actual measured value); 1153.4888 (M+), 688.8556 (M+−4 C$_5$H$_{11}$COOH) (theoretical value of molecular weight)

It was confirmed that the synthesized compound is corresponding to HTL17 from the results of the analysis.

Example 2

Synthesis of Arylamine Compound HTL18

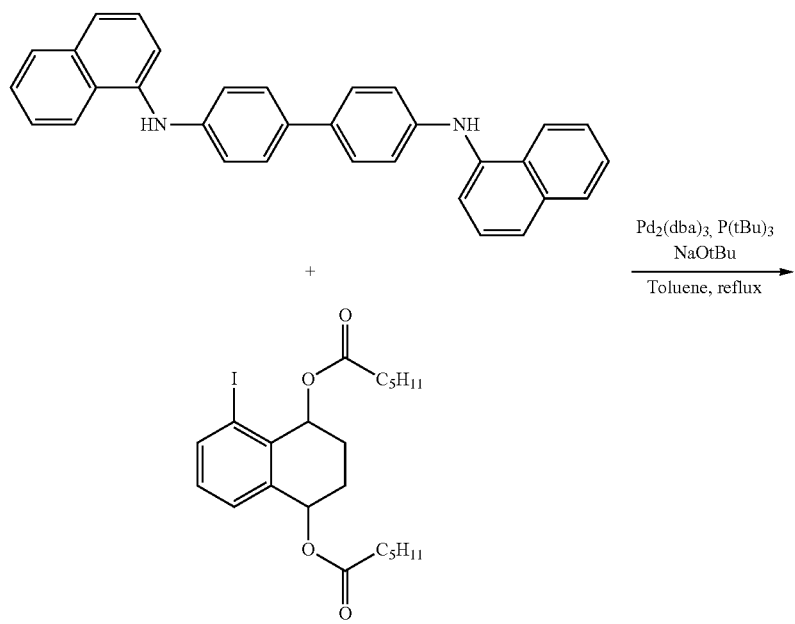

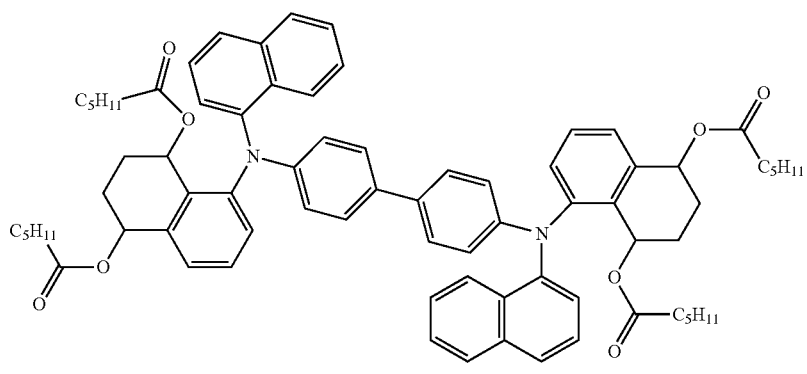

HTL18

HTL18 as pale yellow solid was obtained in a similar manner as example 1, provided that compound 5 was used instead of compound 4 (yield amount: 1.0 g, yield rate: 15.8%).

Precise mass spectrometry (MALDI-TOFMS): m/z=1153.4880 (M+), 689.8559 (M+−4C$_5$H$_{11}$COOH) (actual measured value); 1153.4888 (M+), 688.8556 (M+−4C$_5$H$_{11}$COOH) (theoretical value of molecular weight)

It was confirmed that the synthesized compound is corresponding to HTL18 from the results of the analysis.

Example 3

Synthesis of Arylamine Compound HTL20

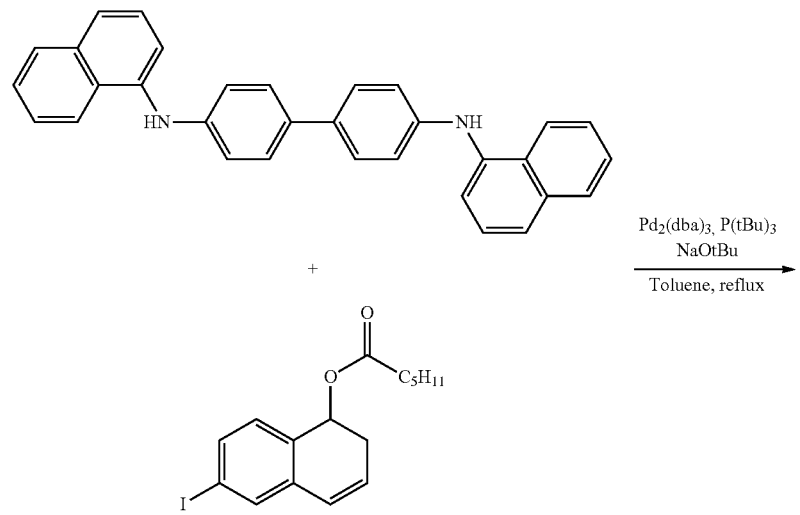

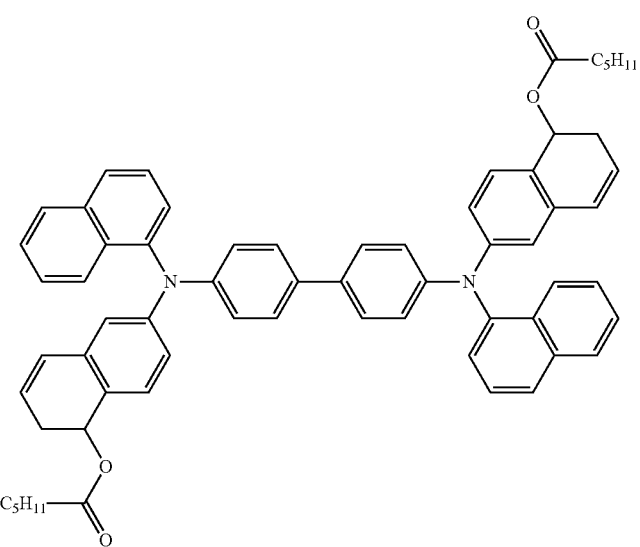

HTL20

HTL20 as pale yellow solid was obtained in a similar manner as example 1, provided that compound 11 was used instead of compound 4 (yield amount: 0.7 g, yield rate: 11.0%).

Precise mass spectrometry (MALDI-TOFMS): m/z=1153.4880 (M+), 689.8549 (M+−4C$_5$H$_{11}$COOH) (actual measured value); 1153.4888 (M+), 688.8556 (M+−4C$_5$H$_{11}$COOH) (theoretical value of molecular weight)

It was confirmed that the synthesized compound is corresponding to HTL20 from the results of the analysis.

Example 4

Synthesis of Arylamine Compound HTL33

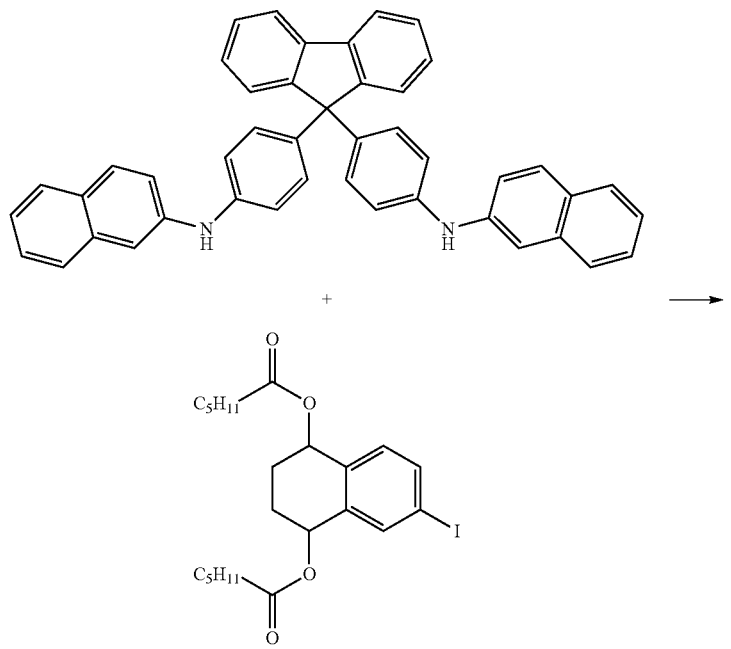

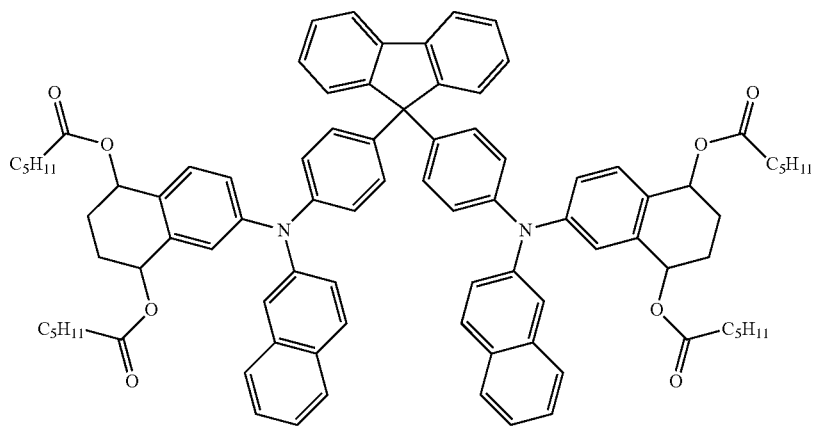

HTL33

HTL33 as pale yellow solid was obtained in a similar manner as example 1, provided that compound 16 was used instead of compound 14 (yield amount: 1.08 g, yield rate: 56.8%).

Precise mass spectrometry (MALDI-TOFMS): m/z=1317.6911 (M+), 853.0589 (M+−4C$_5$H$_{11}$COOH) (actual measured value); 1317.6914 (M+), 853.0583 (M+−4C$_5$H$_{11}$COOH) (theoretical value of molecular weight)

It was confirmed that the synthesized compound is corresponding to HTL33 from the results of the analysis.

Example 5

Synthesis of Arylamine Compound HTL34

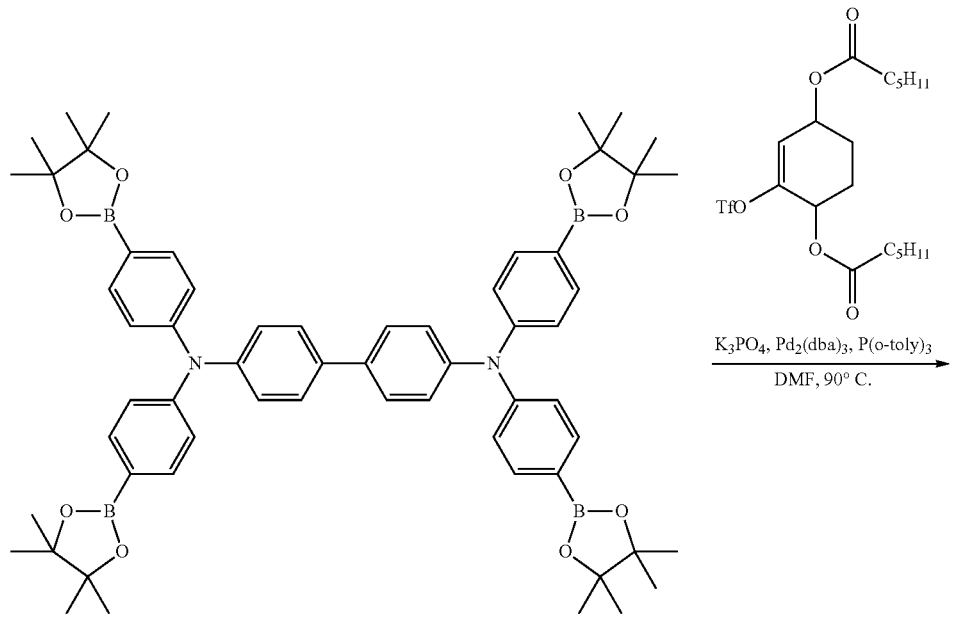

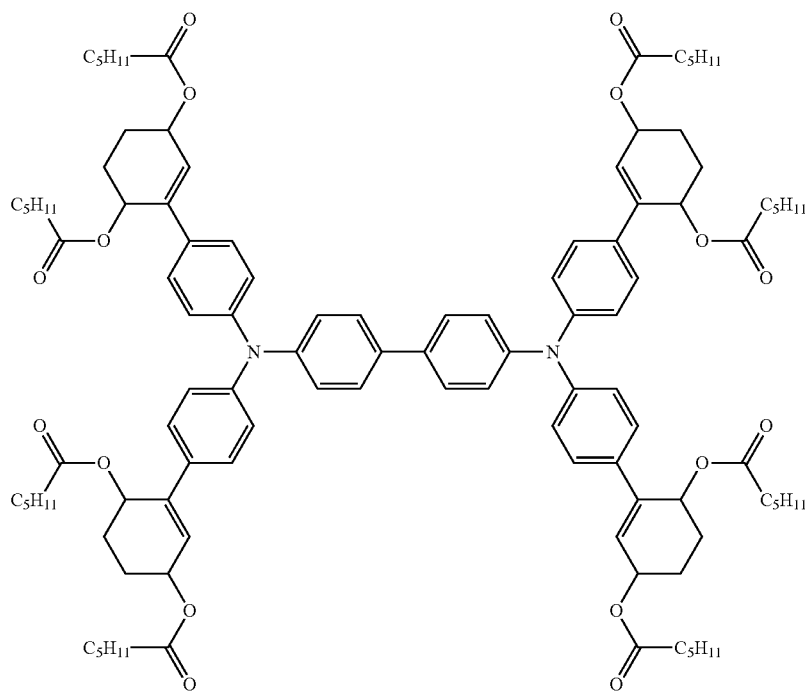

HTL34

A round-bottom flask is charged with compound 15 (2.98 g, 3.0 mmol), compound 12 (6.05 g, 13.2 mmol), potassium phosphate (8.41 g, 39.6 mmol), tris(dibenzylideneacetone) dipalladium (362.0 mg, 0.396 mmol), tri-o-tolylphosphine (481 mg, 1.58 mmol). After the flask is purged with argon gas, DMF (100 mL) was added. Then, the mixture is stirred for 16 hours at 85° C. After the flask is cooled to ambient temperature, the reaction was terminated by adding water. Ethyl acetate and water are added to the reaction solution to isolate an organic phase. A water phase is extracted three times with ethyl acetate. Then, the extract is mixed with the organic phase. The mixture is washed with water and further washed with brine, followed by dried with magnesium sulfate. After removing the drying agent by filtration, the filtrate is concentrated and purified through silica gel chromatography (solvent: toluene/ethyl acetate), followed by washing with methanol to obtain HTL34 as pale yellow solid (yield amount: 3.1 g, yield rate: 60%).

Precise mass spectrometry (MALDI-TOFMS): m/z=1721.0200 (M+), 792.3509 (M+−8C$_5$H$_{11}$COOH) (actual measured value); 1721.0203 (M+), 792.3504 (M+−8C$_5$H$_{11}$COOH) (theoretical value of molecular weight)

It is confirmed that the synthesized compound is corresponding to HTL34 from the results of the analysis.

Example 6

Observation of Aryl Amine Compound, HTL17

HTL17 synthesized in Example 1 was heated at a range of 25° C. to 450° C. at a temperature increasing rate of 5° C./min and the pyrolysis behavior thereof was observed by TG-DTA [reference: Al$_2$O$_3$, under nitrogen flow (200 mL/min), EXSTAR6000 (product name), product of Seiko Instruments Inc.].

Figure 2:
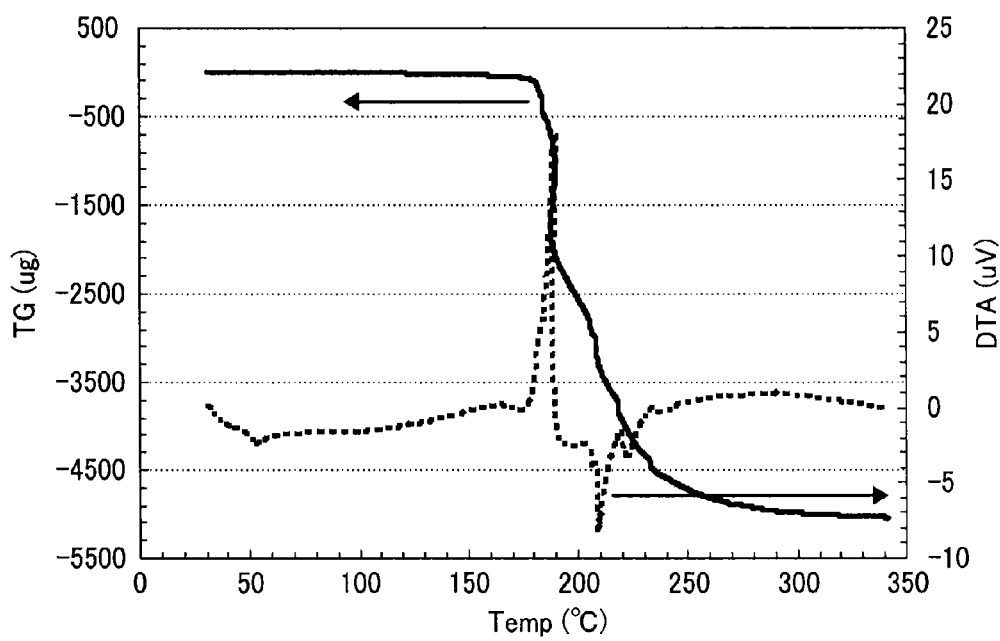
FIG. 2 is data of TG-DTA of an arylamine compound (HTL17).

The results are shown in FIG. 2, where the horizontal axis indicates temperature [° C.], the left-hand vertical axis indicates change in mass [mg] and the right-hand vertical axis indicates DTA signal [μV].

In FIG. 2, 40.0% of mass reduction was observed from ambient temperature to 250° C. The mass reduced coincided substantially with the mass of 4 molecules of hexanoic acid (theoretical value: 40.28%), which are eliminated from HTL17 with converting 4,4'-bis[N-(1-naphthyl)-N-(2-naphthyl)amino]biphenyl (α,β-TNB).

Also, precise mass spectrometry was subjected using the sample, which was taken out when temperature was 200° C. The actual measured value of m/z at 200° C. was 688.2899, which corresponds to theoretical value of molecular weight of α,β-TNB, 688.2899, to 3 decimal places.

From the above results, HTL17 was found to eliminate 4 molecules of hexanoic acid with converting to α,β-TNB by heating in a quantitative way.

From this example, the arylamine compound of above embodiments was found to be able to eliminate the soluble substituent with converting to the eliminated structure thereof in a quantitative way.

Example 7

Observation of Aryl Amine Compound, HTL20

The pyrolysis behavior was observed in a similar manner as Example 6, provided that HTL17 was replaced to HTL20 which was synthesized in Example 3. Then, the amount of mass reduced and the precise mass spectrometry using the sample after heating was measured.

25.1% of mass reduction was observed from ambient temperature to 180° C. The mass reduced coincided substantially with the mass of 2 molecules of hexanoic acid (theoretical value: 25.22%), which are eliminated from HTL20 with converting to 4,4'-bis[N-(1-naphthyl)-N-(2-naphthyl)amino]biphenyl (α,β-TNB).

Also, precise mass spectrometry was subjected using the sample, which was taken out when temperature was 150° C. The actual measured value of m/z at 150° C. was 688.2854, which corresponds to theoretical value of molecular weight of α,β-TNB, 688.2858, to 3 decimal places.

From the above results, HTL20 was found to eliminate 2 molecules of hexanoic acid with converting to α,β-TNB by heating in a quantitative way. Temperature for elimination reaction was found to be lower than that of HTL17.

Example 8

Observation of Aryl Amine Compound, HTL18

The pyrolysis behavior was observed in a similar manner as Example 6, provided that HTL17 was replaced to HTL18 which was synthesized in Example 2. Then, the amount of mass reduced and the precise mass spectrometry using the sample after heating was measured.

The difference of mass reduced between theoretical value and actural measured, calculated in a similar manner as Examples 6 and 7, value was −0.12%.

From the precise mass spectrometry measurement, the actual measured value of m/z corresponds to theoretical value of molecular weight to 3 decimal places.

From the above results, HTL18 was found to be able to convert its structure similar to HTL17 by heating.

Example 9

Observation of Aryl Amine Compound, HTL33

The pyrolysis behavior was observed in a similar manner as Example 6, provided that HTL17 was replaced to HTL33 which was synthesized in Example 4. Then, the amount of mass reduced and the precise mass spectrometry using the sample after heating was measured.

The difference of mass reduced between theoretical value and actural measured value, calculated in a similar manner as Examples 6 and 7, was −0.16%.

From the precise mass spectrometry measurement, the actual measured value of m/z corresponds to theoretical value of molecular weight to 3 decimal places.

From the above results, HTL33 was found to be able to convert its structure similar to HTL17 by heating.

Example 10

Observation of aryl amine compound, HTL34

The pyrolysis behavior is observed in a similar manner as Example 6, provided that HTL17 is replaced to HTL34 which is synthesized in Example 5. Then, the amount of mass reduced and the precise mass spectrometry using the sample after heating is measured.

The difference of mass reduces between theoretical value and actural measured value, calculated in a similar manner as Examples 6 and 7, is −0.18%.

From the precise mass spectrometry measurement, the actual measured value of m/z corresponds to theoretical value of molecular weight to 3 decimal places.

From the above results, HTL34 is found to be able to convert its structure similar to HTL17 by heating.

Example 11

Preparation of Ink (Evaluation of Solubility)

HTL17 was added to each of toluene, chloroform, 2-propanol, 1,2,3,4-tetrahydronaphthalene (Tetralin®), ethyl benzoate (100 mL respectively), until undissolved compound was observed. The mixture was stirred for 10 minute with refluxing the solvent. Then, mixture was cooled to ambient temperature, and stirred for 1 hour, followed by still standing for 16 hours. The supernatant was filtrated by PTFE filter having thickness of 0.2 μm to obtain saturated solution. The saturated solution was dried under reduced pressure to calculate degree of solubility for each solvent.

Example 12

Preparation of Ink (Evaluation of Solubility)

The degree of solubility was calculated in a similar manner as Example 11, provided that HTL17 was replaced by HTD18.

Example 13

Preparation of Ink (Evaluation of Solubility)

The degree of solubility was calculated in a similar manner as Example 11, provided that HTL17 was replaced by HTD20.

Example 14

Preparation of Ink (Evaluation of Solubility)

The degree of solubility was calculated in a similar manner as Example 11, provided that HTL17 was replaced by HTD33.

Example 15

Preparation of Ink (Evaluation of Solubility)

The degree of solubility is calculated in a similar manner as Example 11, provided that HTL17 is replaced by HTD34.

Comparative Example 1

The degree of solubility was calculated in a similar manner as Example 11, provided that HTL17 was replaced by 4,4'-bis[N-(1-naphthyl)-N-(2-naphthyl)amino]biphenyl (α,β-TNB).

Comparative Example 2

The degree of solubility is calculated in a similar manner as Example 11, provided that HTL17 is replaced by 4,4'-tetrakis[N-(1-naphthyl)-N-(2-naphthyl)amino]biphenyl (α-TNB).

Comparative Example 3

The degree of solubility was calculated in a similar manner as Example 11, provided that HTL17 was replaced by 9,9-bis[4-(N,N-bis-naphthalene-2-yl-amino)phenyl]-9H-florene (NPAPF).

Comparative Example 4

The degree of solubility is calculated in a similar manner as Example 11, provided that HTL17 is replaced by N,N,N',N'-tetra-biphenyl-4-yl-benzidine (TBPB).

Evaluation criteria in Table 4 was described below.

A: The degree of solubility is not less than 5% by mass

B: The degree of solubility is not less than 1% by mass but less than 5% by mass.

C: The degree of solubility is less than 1% by mass

TABLE 4

| | | Solvent | | | | |
|---|---|---|---|---|---|---|
| | Compound | Toluene | Chloroform | 2-Propanol | 1,2,3,4-Tetrahydro-naphthalene | ethyl benzoate |
| Ex. 11 | HTL17 | A | A | A | A | A |
| Ex. 12 | HTL18 | A | A | A | A | A |
| Ex. 13 | HTL20 | A | A | A | A | A |
| Ex. 14 | HTL33 | A | A | B | A | A |
| Ex. 15 | HTL34 | A | A | B | A | A |
| Co. EX. 1 | α,β-TNB | A | A | C | A | B |
| Co. EX. 2 | α-TNB | A | A | C | B | B |
| Co. EX. 3 | NPAPF | B | A | C | B | C |
| Co. EX. 4 | TBPB | A | A | C | B | B |

According to table 4, all the arylamine compounds of the examples have high solubility, not less than 1% by mass in all examples and not less than 5% by mass in several examples, to toluene, chloroform, 2-propanol, tetrahydronaphthalene (Tetralin®), and ethyl benzoate.

This shows that the soluble substituent included in a skeleton contributes for the solubility. The arylamine compounds are applicable for inks used in various solution process having an appropriate density and viscosity due to their solubility.

In this case, low polarity solvent such as toluene and tetrahydronaphthalene (Tetralin®), halogen solvent such as chloroform, and high polarity solvent such as 2-propanol and ethyl benzoate can be selected.

In addition, the solvent having boiling point of 60° C. to 200° C. can be selected.

Depending on filming process, for example, the above solvent may be added for obtaining intended property such as polarity and boiling point.

The arylamine compounds are applicable for inks used in various solution process having an appropriate density and viscosity due to their solubility, even if molecular weight thereof are more than 1,000, and therefore it is difficult to make film using general evaporation method other than the method of the present invention.

Example 16

Preparation of Thin Film and Evaluation

HTL17 which was synthesized in Example 1 was dissolved in chloroform to obtain solution (1.0% by mass), followed by filtrated using filter having thickness of 0.2 μm. A n-type silicon substrate comprising thermally-oxidized film having thickness of 300 nm was washed by soaking it into concentrated sulfuric acid for 24 hours. The solution was added dropwise on the substrate. Then petri dish was put until solvent was dried to produce thin film. The thin film was observed using polarization microscope and scanning probe microscope (contact mode, Nanopics (product name), produced by Seiko Instruments Inc.). From the observation, it was found that smooth and continuous amorphous film was formed.

Next, the thin film was subjected to annealing treatment at 180° C. for 60 minutes under argon atmosphere, and then the film was observed similarly. From the result of observation using polarization microscope, the smooth and continuous amorphous film was maintained and crystallization was not observed.

The thin film, which was subjected to annealing treatment, was dissolved into chloroform for precise mass spectrometry measurement. The actual measured value of m/z, 688.2812, corresponds to theoretical value of molecular weight of $\alpha,\beta$-TNB, 688.2878, to 2 decimal places.

From the above results, the thin film made of HTL17 eliminates its leaving substituent to form double bond and converts to $\alpha,\beta$-TNB film by heating in a quantitative way.

Example 17

Preparation of Thin Film and Evaluation

A thin film was prepared, observed, and analyzed in a similar method as Example 16, provided that, HTL17 was replaced to HTL20 and temperature of annealing treatment was replaced to 135° C.

From the result of observation of the thin film, which was subjected to the annealing treatment, using polarization microscope, the smooth and continuous amorphous film was maintained and crystallization was not observed.

The thin film, which was subjected to annealing treatment, was dissolved into chloroform for precise mass spectrometry measurement. The actual measured value of m/z, 688.2855, corresponds to theoretical value of molecular weight of $\alpha,\beta$-TNB, 688.2878, to 2 decimal places.

From the above results, the thin film made of HTL20 eliminates its leaving substituent to form double bond and converts to $\alpha,\beta$-TNB film by heating in a quantitative way.

Comparative Example 5

Preparation of Thin Film and Evaluation

A thin film is prepared, observed, and analyzed in a similar method as Example 16, provided that, HTL17 is replaced to $\alpha,\beta$-TNB.

From the observation of the thin film using polarization microscope, it is found that crystal was partly formed. In addition, discontinuous film is observed due to crystallization by the scanning probe microscope.

From the result of observation of the thin film, which is heated to 180° C., using polarization microscope, it is found that the crystallization proceeded.

As a result of Example 16 and 17, and Comparative example 5, it is found that an amorphous film having low crystallinity, which is suitable for an organic EL material, can be obtained from the arylamine compound of the examples. When a thin film is formed using solution comprising the compound such as $\alpha,\beta$-TNB, which corresponds to the compound of examples except that it does not have the leaving group, crystalline and discontinuous film is obtained. On the other hand, when a thin film is formed using the arylamine compound of the examples and then subjected to annealing treatment, amorphous and continuous film is obtained.

Hereinafter, examples of the arylamine compound and heat transformation film, which are applicable to the organic EL device, will be further described with the following Examples, which should not be construed as limiting the scope of the present invention thereto.

Example 18

EL Device

A clear glass substrate having dimensions of 40×40 is washed by known washing step. A film of ITO is formed in a stripe pattern on the one aspect the substrate to make electrode using known film forming method. Then, the one aspect which the ITO was formed is cleaned by plasma treatment.

Next, the THF solution having 1.0% by mass of the arylamine compound, HTL17 produced in Example 1, is prepared, and then the solution is coated to the substrate using spin-coating process to form a film having thickness of 60 nm. Then, the film is dried.

Next, the substrate is placed in a chamber of vacuum apparatus, and an electron transport layer (60 nm), which is composed of Alq3, was formed using vacuum deposition. Then, an anode is formed in stripe pattern using metal mask by laminating LiF (thickness of 0.25 nm) and MgAg (thickness of 200 nm) in this order using vacuum deposition.

(Evaluation)

The obtained organic EL element is subjected to measurements of voltage dependency of current density, voltage dependency of brightness, and luminescence spectrum. Also, Absolute fluorescence quantum efficiency is calculated.

Example 19

An organic EL element is produced and evaluated in a similar method as Example 18, provided that HTL17 is replaced to HTL18.

Example 20

An organic EL element is produced and evaluated in a similar method as Example 18, provided that HTL17 is replaced to HTL20.

Evaluation results of external efficiency are shown in Table 5.

TABLE 5

| Example | Host material | External efficiency |
|---|---|---|
| Example 18 | HTL17 | 0.25% |
| Example 19 | HTL18 | 0.30% |
| Example 20 | HTL20 | 0.35% |

From Table 5, the arylamine compounds are suitable for the organic EL material having excellent property using solution method.

What is claimed is:

1. An arylamine compound selected from the group consisting of compounds of the formulas HTL1-HTL28:

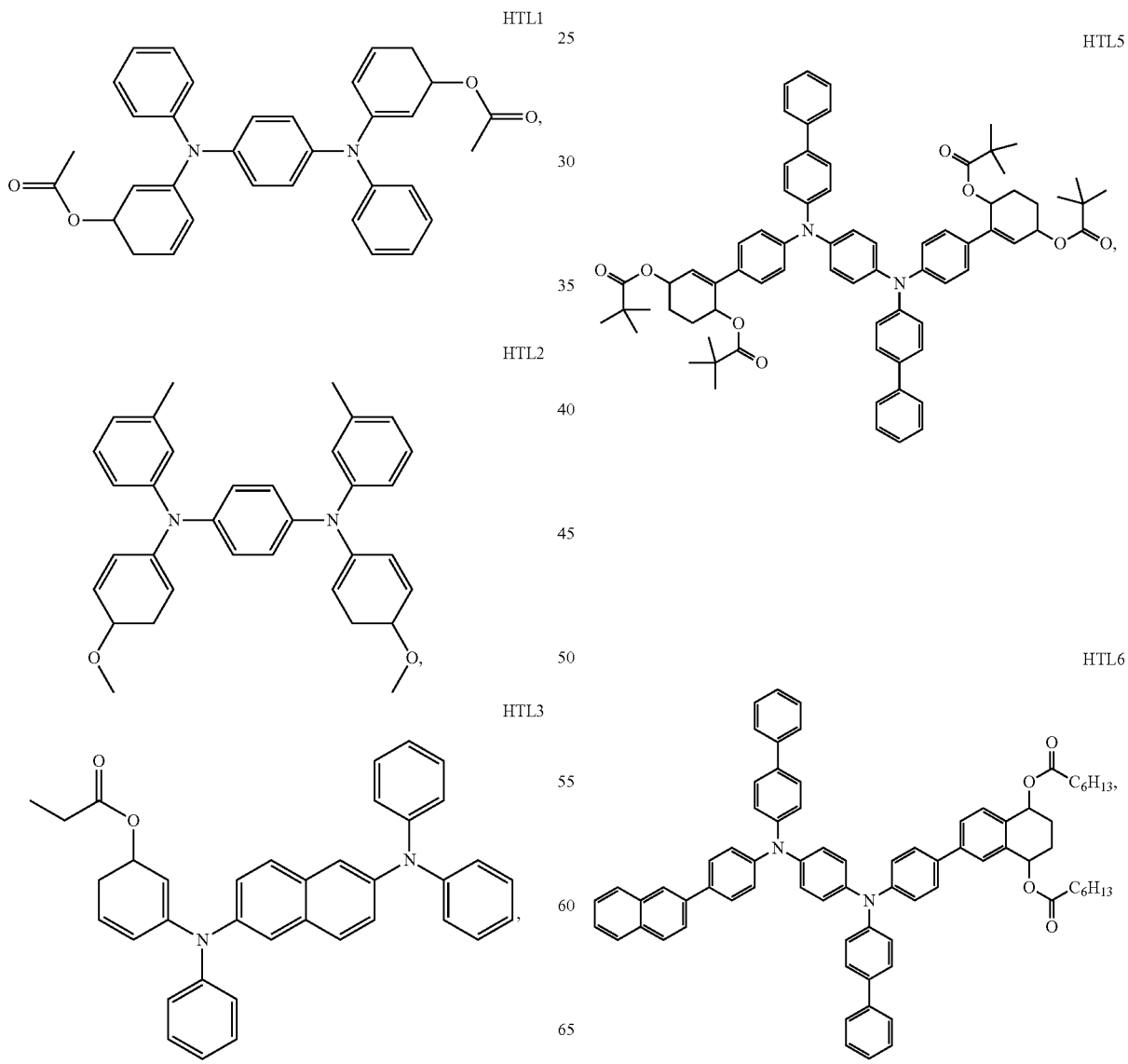

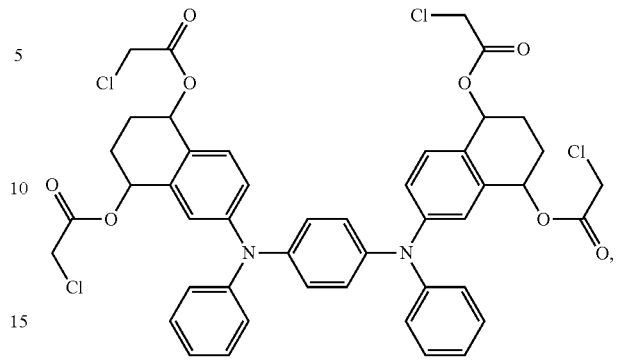

-continued
HTL7
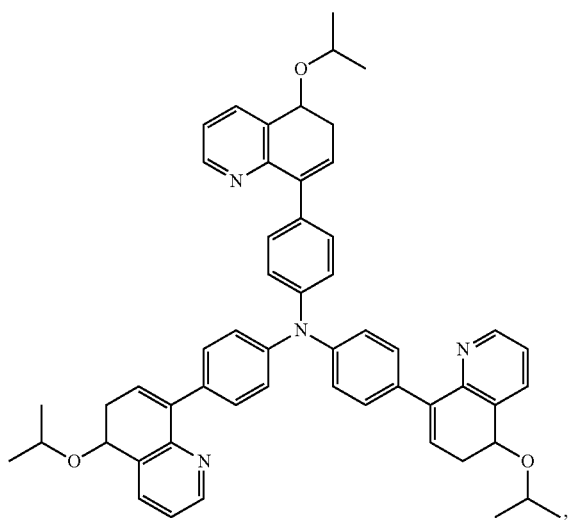
HTL8
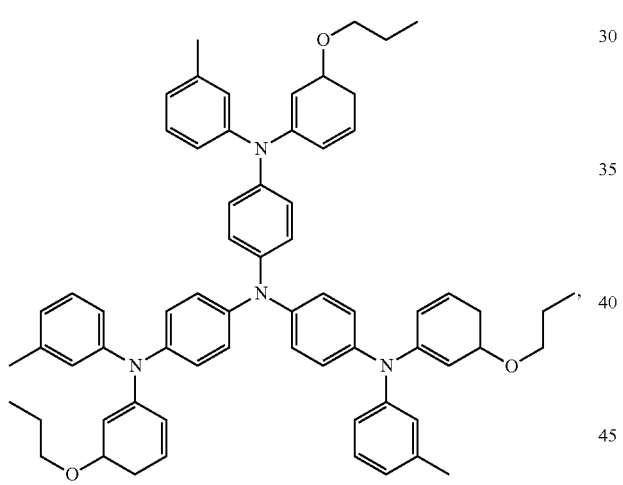
HTL9
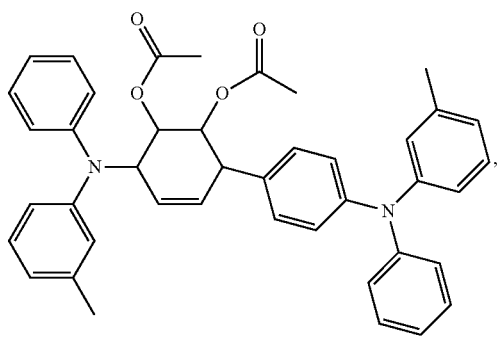
-continued
HTL10
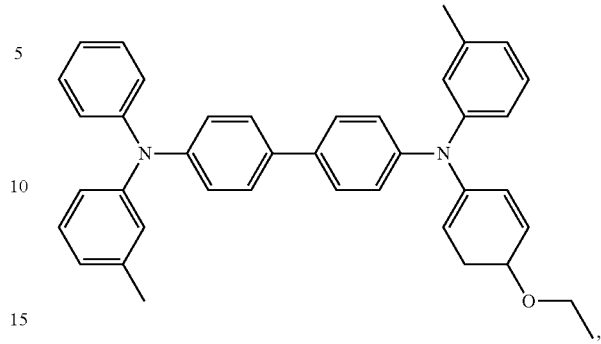
HTL11
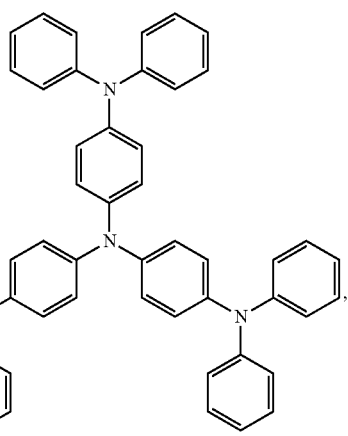
HTL12
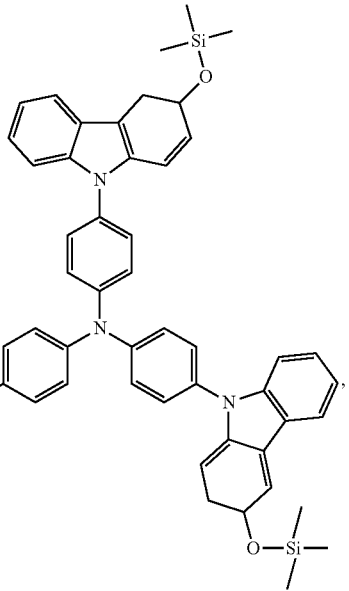

-continued
HTL13
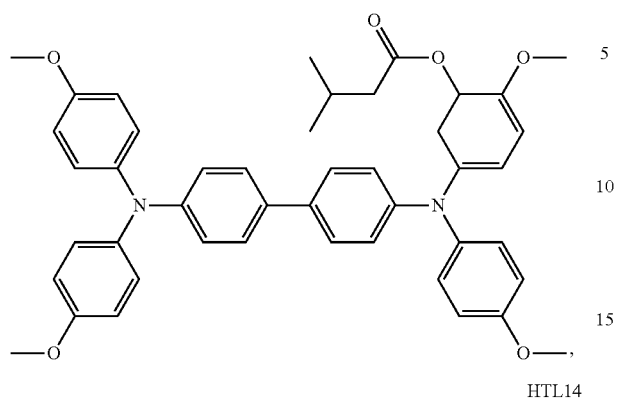
HTL14
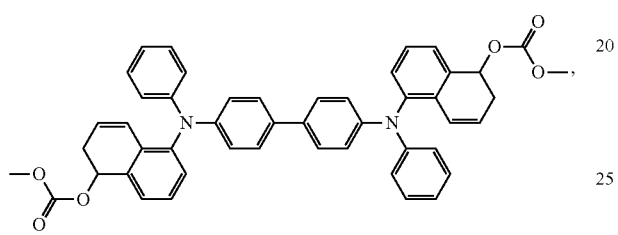
HTL15
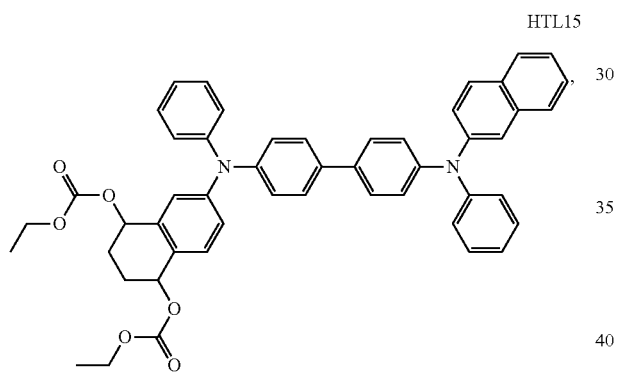
HTL16
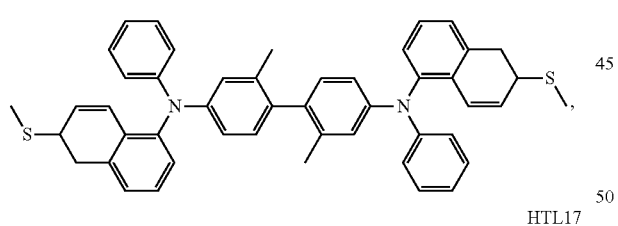
HTL17
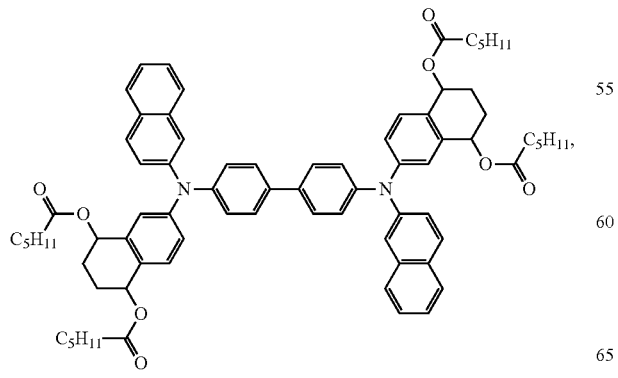
-continued
HTL18
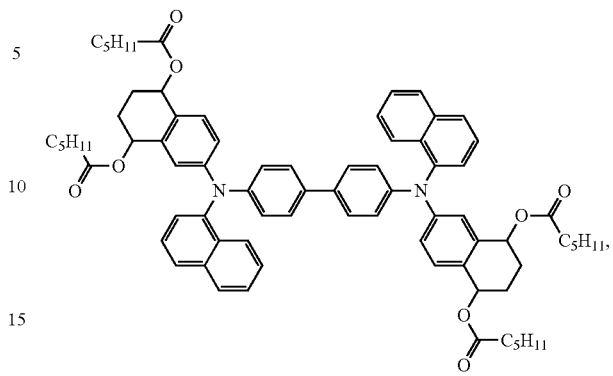
HTL19
HTL20

103
-continued
HTL21
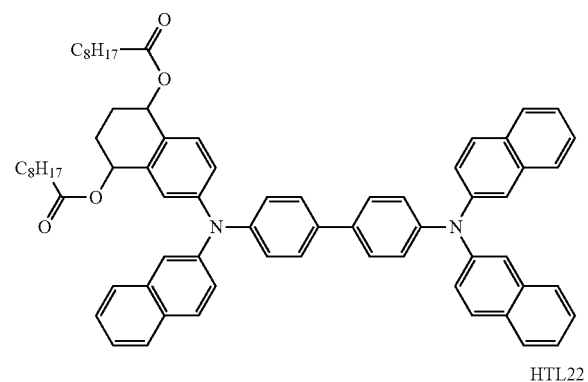
HTL22
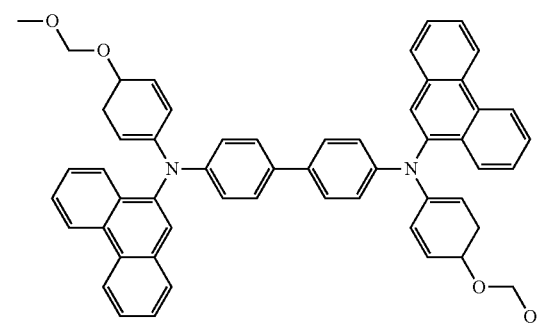
HTL23
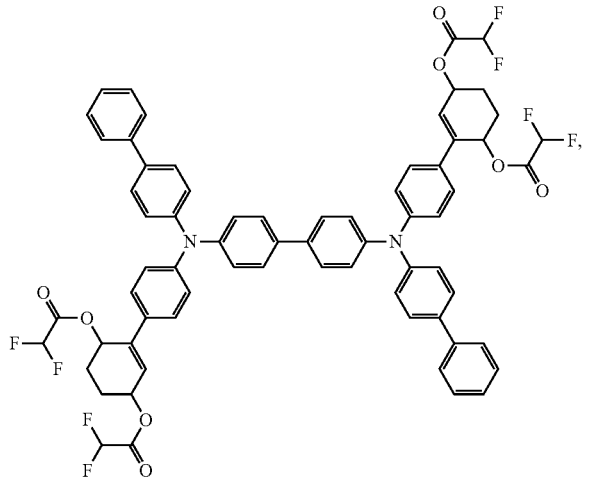
HTL24
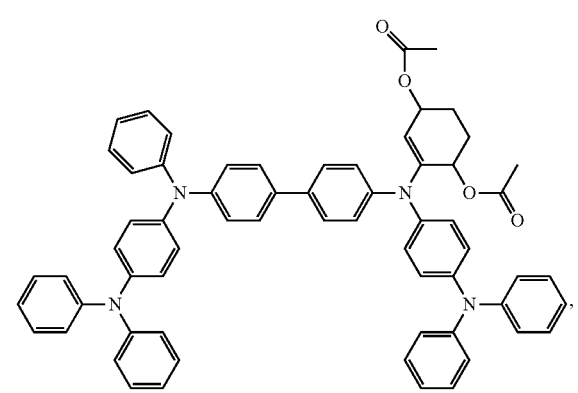
104
-continued
HTL25
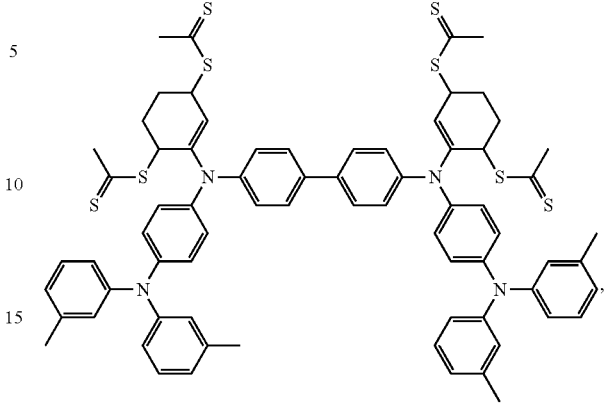
HTL26
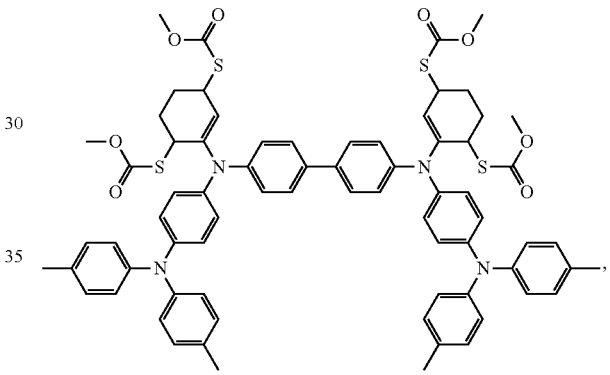
HTL27
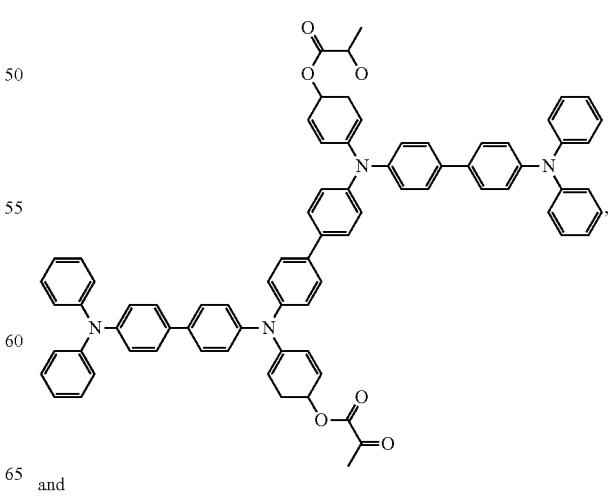
and

HTL28

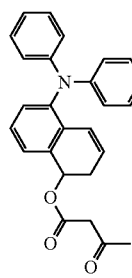

2. The arylamine compound as claimed in claim 1, wherein the arylamine compound is the compound of formula HTL17.

3. The arylamine compound as claimed in claim 1, wherein the arylamine compound is the compound of formula HTL1.

4. The arylamine compound as claimed in claim 1, wherein the arylamine compound is the compound of formula HTL2.

5. The arylamine compound as claimed in claim 1, wherein the arylamine compound is the compound of formula HTL3.

6. The arylamine compound as claimed in claim 1, wherein the arylamine compound is the compound of formula HTL4.

7. The arylamine compound as claimed in claim 1, wherein the arylamine compound is the compound of formula HTL5.

8. The arylamine compound as claimed in claim 1, wherein the arylamine compound is the compound of formula HTL6.

9. The arylamine compound as claimed in claim 1, wherein the arylamine compound is the compound of formula HTL7.

10. The arylamine compound as claimed in claim 1, wherein the arylamine compound is the compound of formula HTL8.

11. The arylamine compound as claimed in claim 1, wherein the arylamine compound is the compound of formula HTL9.

12. The arylamine compound as claimed in claim 1, wherein the arylamine compound is the compound of formula HTL10.

13. The arylamine compound as claimed in claim 1, wherein the arylamine compound is the compound of formula HTL11.

14. The arylamine compound as claimed in claim 1, wherein the arylamine compound is the compound of formula HTL12.

15. The arylamine compound as claimed in claim 1, wherein the arylamine compound is the compound of formula HTL13.

16. The arylamine compound as claimed in claim 1, wherein the arylamine compound is the compound of formula HTL14.

17. The arylamine compound as claimed in claim 1, wherein the arylamine compound is the compound of formula HTL15.

18. The arylamine compound as claimed in claim 1, wherein the arylamine compound is the compound of formula HTL16.

19. The arylamine compound as claimed in claim 1, wherein the arylamine compound is the compound of formula HTL18.

20. The arylamine compound as claimed in claim 1, wherein the arylamine compound is the compound of formula HTL19.

* * * * *